US010626136B2

(12) United States Patent
Prakash et al.

(10) Patent No.: US 10,626,136 B2
(45) Date of Patent: Apr. 21, 2020

(54) COMPOSITIONS AND METHODS FOR IMPROVING REBAUDIOSIDE X SOLUBILITY

(71) Applicants: The Coca-Cola Company, Atlanta, GA (US); PureCircle Sdn Bhd, Negri Semblian (MY)

(72) Inventors: Indra Prakash, Alpharetta, GA (US); Avetik Markosyan, Kuala Lumpur (MY); Venkata Sai Prakash Chaturvedula, Mission Viejo, CA (US); Gil Ma, Atlanta, GA (US)

(73) Assignees: The Coca-Cola Company, Atlanta, GA (US); PureCircle Sdn Bhd (MY)

( * ) Notice: Subject to any disclaimer, the term of this patent is extended or adjusted under 35 U.S.C. 154(b) by 0 days.

(21) Appl. No.: 15/171,400

(22) Filed: Jun. 2, 2016

(65) Prior Publication Data
US 2017/0002034 A1 Jan. 5, 2017

Related U.S. Application Data

(63) Continuation of application No. 14/044,158, filed on Oct. 2, 2013, now abandoned, which is a continuation of application No. PCT/US2012/070564, filed on Dec. 19, 2012.

(51) Int. Cl.
| | | |
|---|---|---|
| *A23L 27/30* | (2016.01) | |
| *C07H 15/256* | (2006.01) | |
| *C07H 15/24* | (2006.01) | |
| *A61K 8/60* | (2006.01) | |
| *A61K 47/26* | (2006.01) | |
| *A61Q 11/00* | (2006.01) | |
| *C07C 31/24* | (2006.01) | |
| *C08B 37/00* | (2006.01) | |
| *C08B 37/16* | (2006.01) | |

(52) U.S. Cl.
CPC ............ *C07H 15/256* (2013.01); *A23L 27/33* (2016.08); *A23L 27/36* (2016.08); *A61K 8/602* (2013.01); *A61K 47/26* (2013.01); *A61Q 11/00* (2013.01); *C07C 31/24* (2013.01); *C07H 15/24* (2013.01); *C08B 37/0009* (2013.01); *C08B 37/0015* (2013.01); *A23V 2002/00* (2013.01)

(58) Field of Classification Search
CPC ... A23L 2/60; A23L 1/22; A23L 1/236; A23L 1/2366; A23L 27/36; C07H 15/24; C13K 1/00
USPC .......................................................... 426/548
See application file for complete search history.

(56) References Cited

U.S. PATENT DOCUMENTS

| | | | |
|---|---|---|---|
| 9,169,285 B2 | 10/2015 | Prakash et al. | |
| 2006/0083838 A1 † | 4/2006 | Jackson | |
| 2007/0082106 A1 | 4/2007 | Lee et al. | |
| 2007/0116800 A1 | 5/2007 | Prakash et al. | |
| 2007/0116823 A1 | 5/2007 | Prakash et al. | |
| 2007/0116828 A1 | 5/2007 | Prakash et al. | |
| 2007/0292582 A1 | 12/2007 | Prakash et al. | |
| 2008/0292764 A1 † | 11/2008 | Prakash | |
| 2008/0292765 A1 | 11/2008 | Prakash et al. | |
| 2008/0292775 A1 | 11/2008 | Prakash et al. | |
| 2010/0099857 A1 † | 4/2010 | Evans | |
| 2011/0160311 A1 | 6/2011 | Prakash et al. | |
| 2011/0183056 A1 * | 7/2011 | Morita ............ | C07H 15/256 426/442 |
| 2011/0195161 A1 | 8/2011 | Upreti et al. | |
| 2011/0195170 A1 | 8/2011 | Shigemura et al. | |
| 2012/0058236 A1 * | 3/2012 | Fosdick ............ | A23L 27/36 426/548 |
| 2015/0017284 A1 | 1/2015 | Prakash et al. | |
| 2015/0216218 A1 | 8/2015 | Prakash et al. | |

FOREIGN PATENT DOCUMENTS

| | | |
|---|---|---|
| WO | WO 2010038911 | 4/2010 |
| WO | WO 2011/094423 | 8/2011 |
| WO | WO 2011/097620 | 8/2011 |
| WO | 2012109506 A1 † | 8/2012 |
| WO | WO 2013/096420 | 6/2013 |

OTHER PUBLICATIONS

International Preliminary Report on Patentability for PCT/US2012/070564, dated Jul. 2, 2015.
Ohta, Masaya et al., "Characterization of Novel Steviol Glycosides from Leaves of Stevia rebaudiana Morita," J. Appl. Glycosci., 57, 199-209 (2010).
Third Party Submission in EP 12890326.7, dated Nov. 30, 2018.
Kren, V., et al., "Glycosides in Medicine: The Role of Glycosidic Residue in Biological Activity", *Current Medicinal Chemistry* 2001, 8, 1313-1338.

\* cited by examiner
† cited by third party

*Primary Examiner* — Jeffrey P Mornhinweg
(74) *Attorney, Agent, or Firm* — King & Spalding

(57) ABSTRACT

Polymorphic and amorphous forms of Rebaudioside X and methods for preparing the same are provided herein. Also provided herein are Rebaudioside X complexes and methods for preparing the same. Sweetener compositions and sweetened compositions comprising Rebaudioside X forms and Rebaudioside X complexes are described, as well as and methods of their preparation. Methods of improving the flavor and/or temporal profile of sweetenable compositions, such as beverages, are also provided herein.

17 Claims, 18 Drawing Sheets

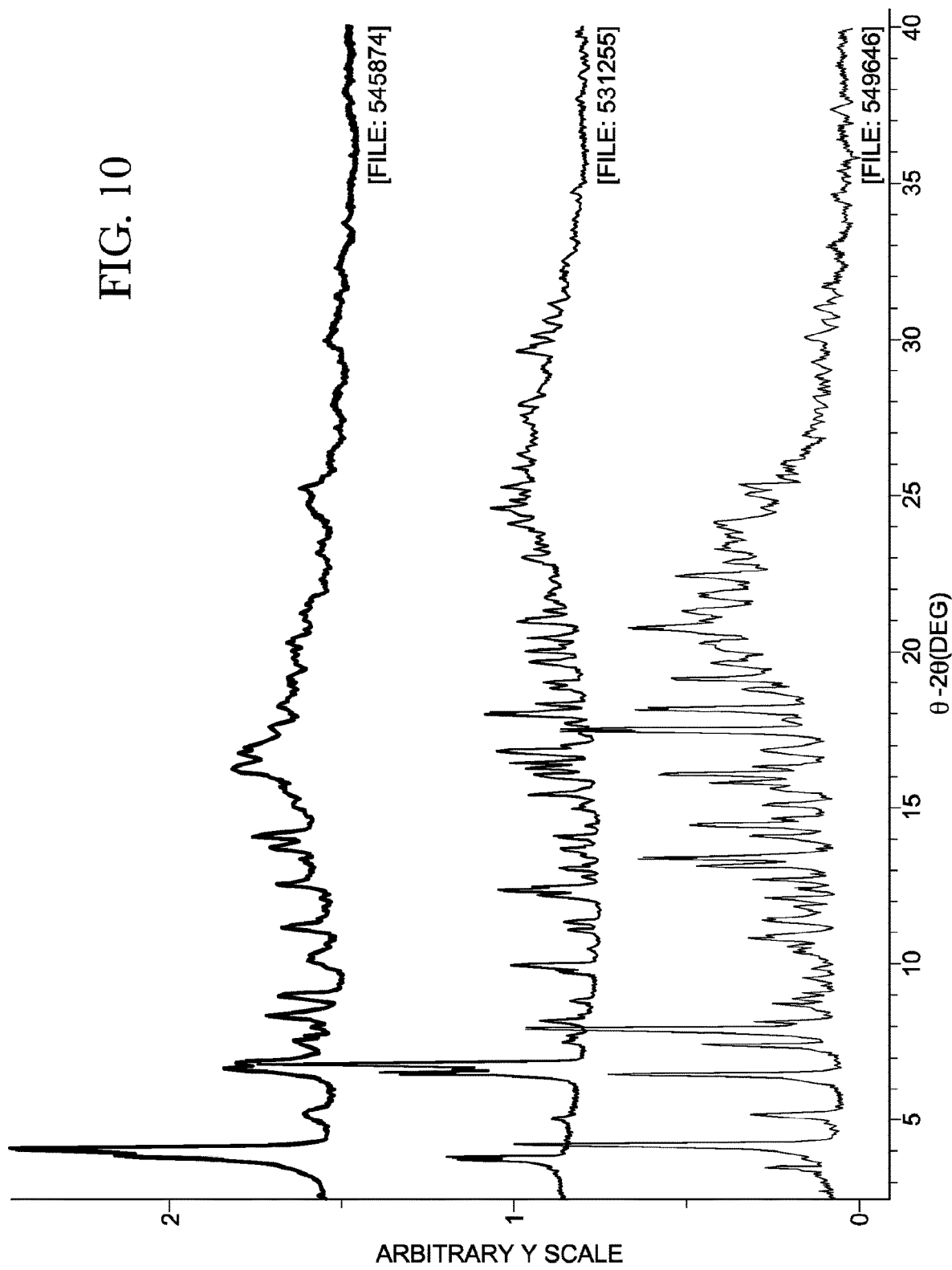

| No. | (ppm) | Height | No. | (ppm) | Height | No. | (ppm) | Height | No. | (ppm) | Height | No. | (ppm) | Height | No. | (ppm) | Height |
|---|---|---|---|---|---|---|---|---|---|---|---|---|---|---|---|---|---|
| 1 | 17.03 | 0.0551 | 12 | 44.54 | 0.0484 | 23 | 71.59 | 0.0327 | 34 | 78.25 | 0.0544 | 45 | 104.21 | 0.0351 | 56 | 135.88 | 0.6172 |
| 2 | 19.91 | 0.0168 | 13 | 46.78 | 0.0208 | 24 | 73.50 | 0.0297 | 35 | 78.36 | 0.0377 | 46 | 104.40 | 0.0384 | 57 | 138.18 | 0.5808 |
| 3 | 20.48 | 0.0187 | 14 | 54.58 | 0.0298 | 25 | 73.85 | 0.0307 | 36 | 78.72 | 0.0398 | 47 | 104.47 | 0.0330 | 58 | 149.90 | 0.9379 |
| 4 | 23.74 | 0.0204 | 15 | 57.66 | 0.0326 | 26 | 75.76 | 0.0355 | 37 | 78.77 | 0.0378 | 48 | 105.02 | 0.0323 | 59 | 150.17 | 0.9441 |
| 5 | 28.52 | 0.0541 | 16 | 62.06 | 0.0278 | 27 | 75.88 | 0.0350 | 38 | 78.92 | 0.0354 | 49 | 105.17 | 0.0191 | 60 | 150.44 | 0.9084 |
| 6 | 38.70 | 0.0270 | 17 | 62.34 | 0.0627 | 28 | 76.02 | 0.0304 | 39 | 81.65 | 0.0303 | 50 | 123.31 | 0.0117 | 61 | 153.60 | 0.0316 |
| 7 | 40.03 | 0.0477 | 18 | 62.85 | 0.0280 | 29 | 77.15 | 0.0291 | 40 | 87.85 | 0.0435 | 51 | 123.60 | 0.9896 | 62 | 177.15 | 0.0314 |
| 8 | 40.59 | 0.0180 | 19 | 64.25 | 0.0757 | 30 | 77.89 | 0.0372 | 41 | 87.85 | 0.0306 | 52 | 123.84 | 1.0000 | | | |
| 9 | 41.47 | 0.0471 | 20 | 70.35 | 0.0309 | 31 | 77.99 | 0.0428 | 42 | 88.90 | 0.0305 | 53 | 124.09 | 0.9870 | | | |
| 10 | 42.85 | 0.0185 | 21 | 70.65 | 0.0312 | 32 | 78.06 | 0.0438 | 43 | 95.18 | 0.0294 | 54 | 124.34 | 0.0143 | | | |
| 11 | 43.60 | 0.0204 | 22 | 71.39 | 0.0331 | 33 | 78.10 | 0.0428 | 44 | 96.50 | 0.0293 | 55 | 135.64 | 0.5908 | | | |

| No. | (ppm) | Height | No. | (ppm) | Height | No. | (ppm) | Height | No. | (ppm) | Height | No. | (ppm) | Height | No. | (ppm) | Height |
|---|---|---|---|---|---|---|---|---|---|---|---|---|---|---|---|---|---|
| 1 | 0.75 | 0.0111 | 15 | 1.35 | 0.2170 | 29 | 1.88 | 0.0375 | 43 | 3.74 | 0.0137 | 57 | 3.91 | 0.0210 | 71 | 4.08 | 0.0888 |
| 2 | 0.78 | 0.0182 | 16 | 1.41 | 0.0142 | 30 | 1.90 | 0.0343 | 44 | 3.75 | 0.0189 | 58 | 3.92 | 0.0239 | 72 | 4.10 | 0.0730 |
| 3 | 0.80 | 0.0101 | 17 | 1.43 | 0.0407 | 31 | 2.04 | 0.0308 | 45 | 3.76 | 0.0194 | 59 | 3.93 | 0.0229 | 73 | 4.14 | 0.1293 |
| 4 | 0.93 | 0.0331 | 18 | 1.45 | 0.0165 | 32 | 2.07 | 0.0277 | 46 | 3.77 | 0.0282 | 60 | 3.93 | 0.0267 | 74 | 4.18 | 0.1484 |
| 5 | 0.96 | 0.0346 | 19 | 1.48 | 0.0076 | 33 | 2.08 | 0.0221 | 47 | 3.77 | 0.0219 | 61 | 3.94 | 0.0280 | 75 | 4.18 | 0.1308 |
| 6 | 1.00 | 0.0361 | 20 | 1.55 | 0.0132 | 34 | 2.25 | 0.0298 | 48 | 3.78 | 0.0164 | 62 | 3.95 | 0.0249 | 76 | 4.19 | 0.0433 |
| 7 | 1.01 | 0.0128 | 21 | 1.67 | 0.0182 | 35 | 2.29 | 0.0345 | 49 | 3.85 | 0.0178 | 63 | 3.96 | 0.0343 | 77 | 4.20 | 0.0432 |
| 8 | 1.03 | 0.0204 | 22 | 1.68 | 0.0160 | 36 | 2.31 | 0.0280 | 50 | 3.85 | 0.0155 | 64 | 3.97 | 0.0378 | 78 | 4.20 | 0.0841 |
| 9 | 1.05 | 0.0217 | 23 | 1.70 | 0.0135 | 37 | 2.34 | 0.0202 | 51 | 3.86 | 0.0182 | 65 | 3.99 | 0.0794 | 79 | 4.21 | 0.0898 |
| 10 | 1.07 | 0.0269 | 24 | 1.72 | 0.0091 | 38 | 2.40 | 0.0078 | 52 | 3.87 | 0.0200 | 66 | 4.00 | 0.0799 | 80 | 4.22 | 0.0900 |
| 11 | 1.10 | 0.0297 | 25 | 1.78 | 0.0307 | 39 | 2.43 | 0.0166 | 53 | 3.88 | 0.0247 | 67 | 4.01 | 0.0878 | 81 | 4.23 | 0.1110 |
| 12 | 1.17 | 0.0360 | 26 | 1.81 | 0.0378 | 40 | 2.46 | 0.0141 | 54 | 3.89 | 0.0248 | 68 | 4.02 | 0.0747 | 82 | 4.24 | 0.1128 |
| 13 | 1.25 | 0.0374 | 27 | 1.82 | 0.0394 | 41 | 2.75 | 0.0379 | 55 | 3.89 | 0.0253 | 69 | 4.03 | 0.0547 | 83 | 4.28 | 0.0290 |
| 14 | 1.30 | 0.0349 | 28 | 1.88 | 0.0233 | 42 | 2.79 | 0.0329 | 56 | 3.90 | 0.0195 | 70 | 4.04 | 0.0551 | 84 | 4.34 | 0.1120 |

COMPOSITIONS AND METHODS FOR IMPROVING REBAUDIOSIDE X SOLUBILITY

CROSS REFERENCE TO RELATED APPLICATIONS

This application is a continuation of U.S. patent application Ser. No. 14/044,158, filed Oct. 2, 2013, which is a continuation of International Application No. PCT/US2012/070564, filed Dec. 19, 2012. The complete disclosures of each are herein incorporated by reference.

FIELD OF THE INVENTION

The present invention relates generally to crystalline forms and amorphous Rebaudioside X and methods of preparing the same. The present invention also relates to Rebaudioside X complexes and methods of preparing the same. Certain forms of Rebaudioside X and the Rebaudioside X complexes are advantageous compared to other forms of Rebaudioside X because of improved aqueous solubility. The present invention also encompasses sweetener compositions and sweetened compositions comprising amorphous Rebaudioside X and Rebaudioside X complexes in addition to methods for preparing the same.

BACKGROUND OF THE INVENTION

*Stevia* is the common name for *Stevia rebuadiana* (Bertoni), a perennial shrub of the Asteracae (Compositae) family native to Brazil and Paraguay. The plant's leaves, the aqueous extract of the leaves, and purified stevioglycosides have been developed as sweeteners desirable as both non-caloric and natural in origin. Specific steviol glycosides that can be isolated from *Stevia rebuadiana* include Stevioside, Rebaudioside A, Rebaudioside C, Dulcoside A, Rubusoside, steviolbioside, Rebaudioside B, Rebaudioside D and Rebaudioside F.

More recently, Rebaudioside X, 13-[2-O-β-D-glucopyranosyl-3-O-β-D-glucopyranosyl-β-D-glucopyranosyl)oxy] ent kaur-16-en-19-oic acid-[(2-O-β-D-glucopyranosyl-3-O-β-D-glucopyranosyl-β-D-glucopyranosyl) ester] was isolated from *Stevia rebuadiana* and characterized:

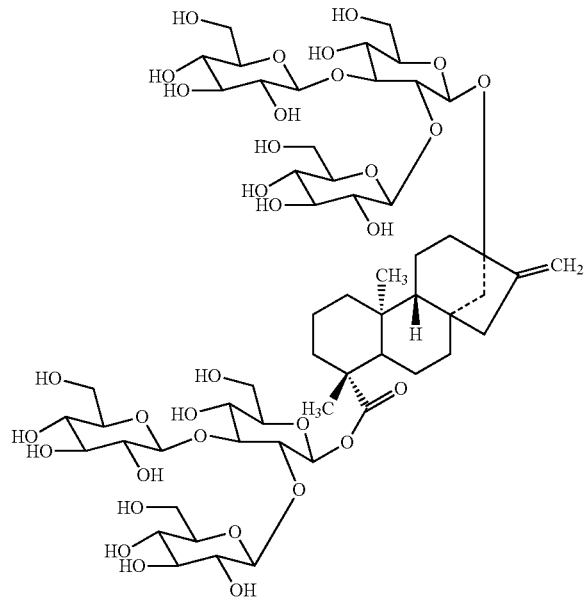

Rebaudioside X can be obtained from *Stevia rebaudiana*, and is present in minute quantities, about 1%-2% by weight. Rebaudioside X obtained from *Stevia rebuadiana* has poor aqueous solubility and dissolution qualities in beverage formulations. Accordingly, there remains a need to develop Rebaudioside X and Rebaudioside X compositions with improved aqueous solubility.

SUMMARY OF THE INVENTION

In one embodiment, the present invention provides Form A Rebaudioside X, a variable hydrate/solvate. In a particular embodiment, Form A Rebaudioside X can be characterized by the X-ray diffraction pattern of FIG. 1 when prepared by ambient temperature slurrying of x-ray amorphous Rebaudioside X in a 1:1 mixture of methanol and water.

The present invention also provides a method for preparing Form A Rebaudioside X. In one embodiment, a method for preparing Form A Rebaudioside X comprises (i) combining Rebaudioside X and an aqueous alcoholic solvent to provide a mixture; and (ii) stirring the mixture at approximately room temperature to provide Form A Rebaudioside X. In some embodiments, the aqueous alcoholic solvent is water and methanol.

The present invention provides a method for preparing amorphous Rebaudioside X from comprising (i) heating a mixture comprising solvent and Rebaudioside X, (ii) cooling the mixture and (iii) removing the solvent from the mixture to provide amorphous Rebaudioside X. The Rebaudioside X can be Form A or Material E Rebaudioside X. The solvent can be any suitable solvent, such as, for example, water, methanol and/or ethanol. In a particular embodiment, the solvent is water. In another embodiment, the solvent is ethanol. In another particular embodiment, the mixture is heated to reflux. In another particular embodiment, the solvent is removed by evaporation or spray-drying.

Amorphous Rebaudioside X is characterized by a X-ray diffraction pattern of FIG. 4. In a particular embodiment, amorphous Rebaudioside X is substantially pure, i.e. about 90% pure relative to other forms of Rebaudioside X. In other embodiments, amorphous Rebaudioside X is greater than about 95% or 98% pure relative to other forms of Rebaudioside X. In yet other embodiments, amorphous Rebaudioside X is provided in the absence of other forms of Rebaudioside X.

Amorphous Rebaudioside X has improved solubility properties compared to other forms of Rebaudioside X, including Form A Rebaudioside X. In one embodiment, amorphous Rebaudioside X has an aqueous solubility greater than about 0.3%.

In a still further embodiment, the present invention is a sweetener composition comprising amorphous Rebaudioside X. In one embodiment, amorphous Rebaudioside X can be the sole sweetener in a sweetener composition. In other embodiments, a sweetener composition comprises amorphous Rebaudioside X, wherein the amorphous Rebaudioside X is provided as part of partially purified *Stevia* extract or part of a mixture of steviol glycosides (i.e. a composition comprising amorphous Rebaudioside X).

The present invention also provides for methods of preparing Form B Rebaudioside X. In one embodiment, a method for preparing Form B Rebaudioside X comprises (i) heating a mixture of amorphous Rebaudioside X and a solvent, (ii) cooling the mixture and (iii) removing the solvent from the mixture to provide Form B Rebaudioside X. In one embodiment, the solvent is ethanol. In another embodiment, the mixture is heated to a temperature between about 30° C. and 100° C. Form B Rebaudioside X can be characterized by the X-ray diffraction pattern shown in FIGS. 7A and 7B when generated by slurrying in ethanol at 40° C.

In another aspect of the invention, Rebaudioside X complexes are provided. The Rebaudioside complexes have improved aqueous solubility over Form A Rebaudioside X. The complexes are prepared by certain methods that provide compositions with increased aqueous solubility.

In one embodiment, Rebaudioside X complexes comprising Rebaudioside X and at least one polyol are provided. Such compositions can be prepared by (i) heating a mixture comprising solvent, Rebaudioside X and at least one polyol; (ii) cooling the mixture; and (iii) removing the solvent from the mixture to provide a Rebaudioside X complex. In a particular embodiment, the at least one polyol is erythritol. In another embodiment, the weight ratio of Rebaudioside X to erythritol is from about 1:1 to about 1:20.

In another embodiment, Rebaudioside X complexes comprising Rebaudioside X and at maltodextrin are provided. Such compositions can be prepared by (i) heating a mixture comprising solvent, Rebaudioside X and maltodextrin; (ii) cooling the mixture; and (iii) removing the solvent from the mixture to provide a Rebaudioside X complex. In a particular embodiment, the weight ratio of Rebaudioside X to maltodextrin is from about 1:1 to about 1:20.

In still another embodiment, Rebaudioside X complexes comprising Rebaudioside X and at least one cyclodextrin are provided. Such compositions can be prepared by (i) heating a mixture comprising solvent, Rebaudioside X and at least one cyclodextrin; (ii) cooling the mixture and (iii) removing the solvent from the mixture to provide a Rebaudioside X complex. In a particular embodiment, the at least one cyclodextrin is selected from the group consisting of α-cyclodextrin, β-cyclodextrin, γ-cyclodextrin, or a derivative thereof. In a more particular embodiment, the at least one cyclodextrin is γ-cyclodextrin. In still another embodiment, the weight ratio of Rebaudioside X to the at least one cyclodextrin is from about 1:1 to about 1:20.

Amorphous Rebaudioside X, Rebaudioside X complexes or compositions comprising the same can be used in a sweetener composition. In one embodiment, the sweetener compositions of the present invention can also contain one or more additional sweeteners, including, for example, natural sweeteners, high potency sweeteners, carbohydrate sweeteners, synthetic sweeteners and combinations thereof.

The present invention also provides methods for preparing sweetener compositing comprising combining amorphous Rebaudioside X or a composition comprising amorphous Rebaudioside X with at least one sweetener and/or additive and/or functional ingredient.

The present invention also provides methods for preparing sweetener compositing comprising combining Rebaudioside X complexes or a composition comprising a Rebaudioside X complex with at least one sweetener and/or additive and/or functional ingredient The sweetener compositions of the present invention can also contain one or more additives including, for example, carbohydrates, polyols, amino acids and their corresponding salts, poly-amino acids and their corresponding salts, sugar acids and their corresponding salts, nucleotides, organic acids, inorganic acids, organic salts including organic acid salts and organic base salts, inorganic salts, bitter compounds, flavorants and flavoring ingredients, astringent compounds, proteins or protein hydrolysates, surfactants, emulsifiers, flavonoids, alcohols, polymers and combinations thereof.

The sweetener compositions of the present invention can also contain one or more functional ingredients, such as, for example, saponins, antioxidants, dietary fiber sources, fatty acids, vitamins, glucosamine, minerals, preservatives, hydration agents, probiotics, prebiotics, weight management agents, osteoporosis management agents, phytoestrogens, long chain primary aliphatic saturated alcohols, phytosterols and combinations thereof.

In yet another embodiment, the present invention is a tabletop sweetener composition comprising amorphous Rebaudioside X or a sweetener composition comprising amorphous Rebaudioside X. In another embodiment, the present invention is a tabletop sweetener composition comprising a Rebaudioside X complex or a sweetener composition comprising a Rebaudioside X complex. The tabletop composition can further include at least one bulking agent, additive, anti-caking agent, functional ingredient and combinations thereof.

In another embodiment, the present invention includes sweetened compositions comprising a sweetenable composition and amorphous Rebaudioside X or a sweetener composition comprising Rebaudioside X. In one embodiment, the sweetened composition comprises a sweetenable composition and amorphous Rebaudioside X. In another embodiment, the sweetened composition comprises a sweetenable composition and a sweetener composition comprising amorphous Rebaudioside X. The sweetened compositions of the present invention can optionally include additives, sweeteners, functional ingredients and combinations thereof.

The present invention also includes sweetened compositions comprising a sweetenable composition and a Rebaudioside X complex or a sweetener composition comprising a Rebaudioside X complex. In one embodiment, a sweetened composition comprises a sweetenable composition and a Rebaudioside X complex. In another embodiment, a sweetened composition comprises a sweetenable composition and a sweetener composition comprising a Rebaudioside X complex. The sweetened compositions of the present invention can optionally include additives, sweeteners, functional ingredients and combinations thereof.

The sweetenable composition may be unsweetened or sweetened. Sweetenable compositions are substances that are desirable to sweeten, including ingested substances and substances that are contacted with the mouth but not eaten or swallowed such as, for example, pharmaceutical compositions, edible gel mixes and compositions, dental compositions, foodstuffs, beverages and beverage products.

In one embodiment, the present invention provides a method for preparing a sweetened composition comprising combining a sweetenable composition with amorphous Rebaudioside X or a sweetener composition comprising amorphous Rebaudioside X.

In another embodiment, the present invention provides a method for preparing a sweetened composition comprising combining a sweetenable composition with a Rebaudioside X complex or a sweetener composition comprising a Rebaudioside X complex.

In a particular embodiment, the sweetenable composition or sweetened composition is a beverage. In one embodiment, the sweetenable composition is a beverage comprising a liquid matrix. The liquid matrix may be, for example, deionized water, distilled water, degassed water, reverse osmosis water, carbon-treated water, purified water, demineralized water, phosphoric acid, phosphate buffer, citric acid, citrate buffer or carbon-treated water.

In one embodiment, the present invention provides a method for preparing a beverage comprising combining an unsweetened or sweetened beverage with amorphous Rebaudioside X or a sweetener composition comprising amorphous Rebaudioside X. In another embodiment, the present invention provides a method for preparing a beverage product comprising combining an unsweetened or sweetened beverage product with amorphous Rebaudioside X or a sweetener composition comprising amorphous Rebaudioside X.

In another embodiment, the present invention is a method for preparing a beverage by combining an unsweetened or sweetened beverage with a Rebaudioside X complex or a sweetener composition comprising a Rebaudioside X complex. In another embodiment, the present invention is a method for preparing a beverage product by combining an unsweetened or sweetened beverage product with a Rebaudioside X complex or a sweetener composition comprising a Rebaudioside X complex.

Sweetened compositions retain the identity of the sweetenable composition upon addition of amorphous Rebaudioside X, a Rebaudioside X complex or the sweetener compositions of the present invention, such that the sweetened composition may also be, for example, pharmaceutical compositions, edible gel mixes and compositions, dental compositions, foodstuffs, beverages and beverage products. In one embodiment, the sweetened composition is a beverage comprising amorphous Rebaudioside X. In another embodiment, the sweetened composition is a beverage comprising a sweetener composition of the present invention. Full-calorie, mid-calorie, low-calorie and zero-calorie beverages containing amorphous Rebaudioside X, a Rebaudioside X complex or the sweetener compositions of the present invention are encompassed by the present invention.

In a still further embodiment, the present invention is a method for imparting a more sugar-like temporal profile, flavor profile, or both to a sweetenable composition by combining a sweetenable composition with amorphous Rebaudioside X or the sweetener compositions of the present invention. The method can further include the addition of other sweeteners, additives, functional ingredients and combinations thereof.

BRIEF DESCRIPTION OF THE FIGURES

FIG. 10: illustrates the X-ray diffraction pattern of Material E (top trace), Form A Rebaudioside X (middle trace, prepared via 1:1 methanol:water (v/v) slurry held at ambient temperature overnight) and Form B Rebaudioside X (bottom trace, prepared via ethanol slurry at 40° C.). Collected with Cu-Kα radiation Cu-Kα radiation (the wavelength used to calculate d-spacings was 1.541874 Å, a weighted average of the Cu-$K_{\alpha 1}$ and Cu-$K_{\alpha 2}$ wavelengths).

FIG. 11B: provides the peaks (ppm) and heights associated with the $^{13}$C NMR spectrum of Reb X in FIG. 11A.

FIG. 12C: provides the peaks (ppm) and heights associated with the $^1$H NMR spectrum of Reb X in FIGS. 12A and 12B.

DETAILED DESCRIPTION OF THE INVENTION

The present invention is directed to novel crystalline polymorphic and amorphous forms of Rebaudioside X, including an amorphous form of Rebaudioside X with increased aqueous solubility. Compositions comprising amorphous Rebaudioside X, as well as methods for preparing amorphous Rebaudioside X and other forms of Rebaudioside X are also provided. Finally, compositions comprising amorphous Rebaudioside X are also provided. Forms of Rebaudioside X, and their respective conversions are as follows:

Material E ⇌ Form A ⇌ amorphous→Form B

As used herein, "amorphous" is defined as a non-crystalline solid material.

The amorphous form of Rebaudioside X and a polymorphic form of Rebaudioside X (e.g. Forms A and B) can be distinguished from other forms of Rebaudioside X by X-ray diffraction patterns, differential scanning calorimetry thermograms, the methods by which they are made and solubility characteristics. The amorphous form of Rebaudioside X, Form A Rebaudioside X and other polymorphic forms of Rebaudioside X (e.g. Form B Rebaudioside X) are referred to herein in the collective as "forms of Rebaudioside X".

As used herein, the term "substantially pure", when used in reference to Rebaudioside X, refers to forms of Rebaudioside X which are greater than about 90% pure by weight on a dry basis. This means that the crystalline or amorphous form of Rebaudioside X does not contain more than about 10% of another form. For example, substantially pure Form A Rebaudioside X does not contain more than about 10% of non-Form A Rebaudioside X. In another example, substantially pure amorphous Rebaudioside X does not contain more than about 10% of non-amorphous Rebaudioside X.

Form A Rebaudioside X

Figure 1:
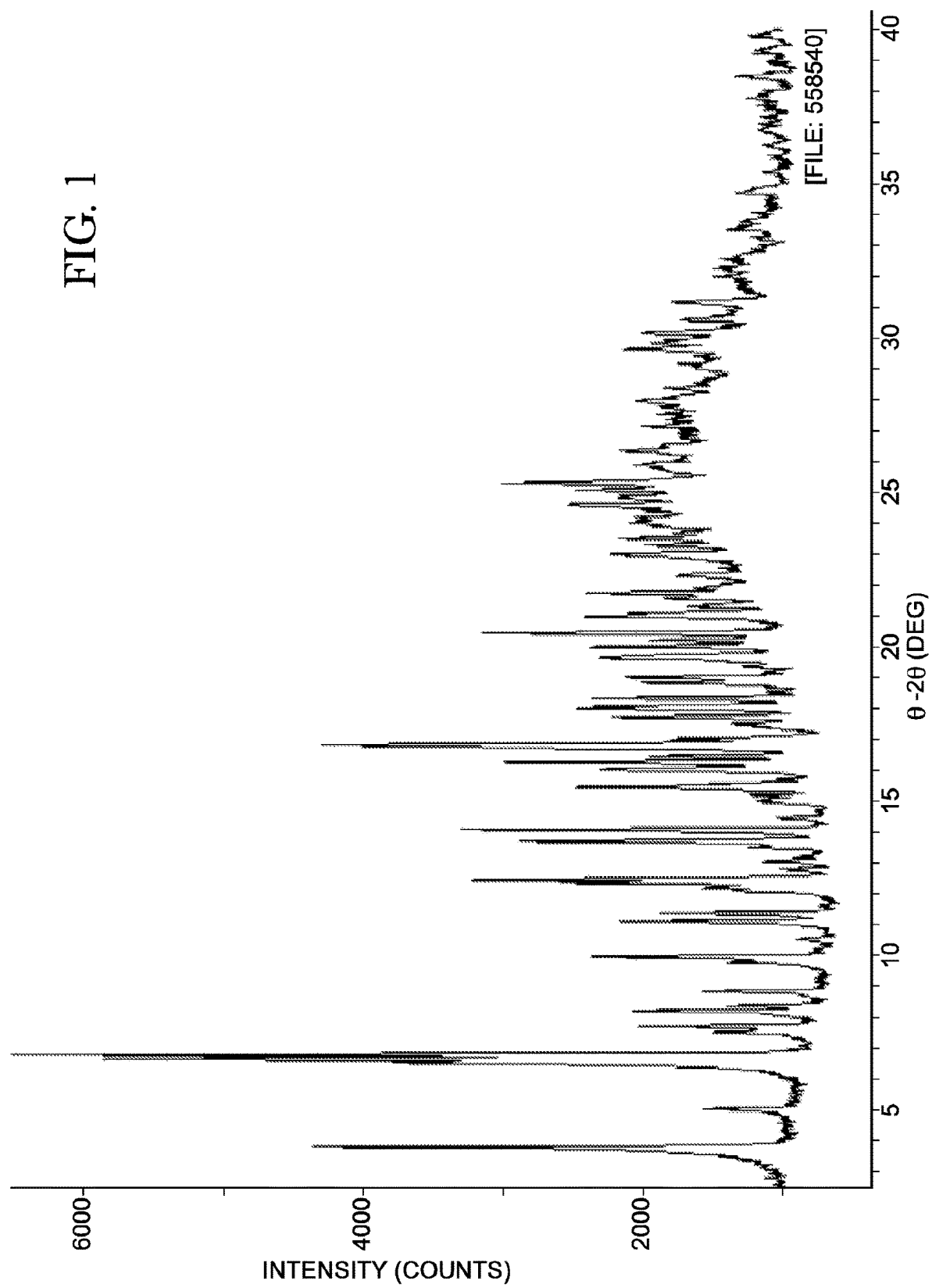
FIG. 1: illustrates the X-ray diffraction pattern of Form A Rebaudioside X collected with Cu-Kα radiation (the wavelength used to calculate d-spacings was 1.541874 Å, a weighted average of the Cu-$K_{\alpha 1}$ and Cu-$K_{\alpha 2}$ wavelengths). Material for this trace was prepared via 1:1 methanol:water (v/v) slurry held at ambient temperature overnight.

The Form A Rebaudioside X polymorph, a variable hydrate/solvate, can be characterized, for example, by the X-ray diffraction pattern shown in FIG. 1, when generated by ambient temperature slurrying of x-ray amorphous Rebaudioside X in a 1:1 mixture of methanol and water. The angular positions (two theta) of the prominent X-ray diffraction peaks are as follows (Table 1) when generated by ambient temperature slurrying of x-ray amorphous Rebaudioside X in a 1:1 mixture of methanol and water:

TABLE 1

Form A Rebaudioside X Prominent XPRD

| °2Θ | d space (Å) | Intensity (%) |
|---|---|---|
| 3.76 ± 0.20 | 23.489 ± 1.319 | 67 |
| 6.50 ± 0.20 | 13.594 ± 0.431 | 58 |
| 6.62 ± 0.20 | 13.354 ± 0.416 | 89 |
| 6.79 ± 0.20 | 13.025 ± 0.395 | 100 |
| 9.93 ± 0.20 | 8.909 ± 0.183 | 36 |
| 12.33 ± 0.20 | 7.176 ± 0.118 | 40 |
| 12.45 ± 0.20 | 7.109 ± 0.116 | 49 |
| 13.69 ± 0.20 | 6.469 ± 0.095 | 44 |
| 14.06 ± 0.20 | 6.301 ± 0.090 | 50 |
| 15.44 ± 0.20 | 5.738 ± 0.075 | 37 |
| 16.25 ± 0.20 | 5.456 ± 0.068 | 46 |
| 16.80 ± 0.20 | 5.278 ± 0.063 | 66 |
| 20.44 ± 0.20 | 4.345 ± 0.042 | 48 |

One of skill in the art will recognize that XRPD patterns of Form A Rebaudioside X produced under different conditions may display peak shifts from those of FIG. 1, consistent with the variable solvent/water content of the material.

Form A exists as a solvate/hydrate, with approximately 9 moles of water and 16 moles of methanol per one mole of Rebaudioside X.

In one embodiment, the invention is Form A Rebaudioside X in substantially pure form. In other embodiments, Form A Rebaudioside X is greater than about 91%, 92%, 93%, 94%, 95%, 96%, 97% or 98% pure with respect to other forms of Rebaudioside X.

In another embodiment, Form A Rebaudioside X is provided in the absence of other forms of Rebaudioside X, i.e. 100% pure Form A Rebaudioside X with respect to other forms of Rebaudioside X.

In one embodiment, a method for preparing Form A Rebaudioside X comprises:
  (i) combining Rebaudioside X and an aqueous alcoholic solvent to provide a mixture; and
  (iii) stirring the mixture at approximately room temperature to provide Form A Rebaudioside X.

In particular embodiment, the form of Rebaudioside X used in (i) is X-ray amorphous Rebaudioside X. In another particular embodiment, the form of Rebaudioside X used in (i) is Material E Rebaudioside X. As used herein, "Material E", when used in reference to Rebaudioside X, refers to composition comprising Rebaudioside X that appears similar to Form A Rebaudioside X by XRPD, but is severely disordered and could not be indexed. The "material" may contain one or more polymorphic and/or amorphous forms of Rebaudioside X.

In one embodiment, Rebaudioside X prepared by the following process can be used in (i): two kg of *Stevia rebaudiana* Bertoni plant leaves were dried at 45° C. to an 8.0% moisture content and ground to 10-20 mm particles. The content of different glycosides in the leaves was as follows: Stevioside—2.55%, Reb A—7.78%, Reb B—0.01%, Reb C—1.04%, Reb D—0.21%, Reb F—0.14%, Reb X—0.10% Dulcoside A—0.05%, and Steviolbioside—0.05%. The dried material was loaded into a continuous extractor and the extraction was carried out with 40.0 L of water at a pH of 6.5 at 40° C. for 160 min. The filtrate was collected and subjected to chemical treatment. Calcium oxide in the amount of 400 g was added to the filtrate to adjust the pH within the range of 8.5-9.0, and the mixture was maintained for 15 min with slow agitation. Then, the pH was adjusted to around 3.0 by adding 600 g of $FeCl_3$ and the mixture was maintained for 15 min with slow agitation. A small amount of calcium oxide was further added to adjust the pH to 8.5-9.0 and the mixture was maintained for 30 min with slow agitation. The precipitate was removed by filtration on a plate-and-frame filter press using cotton cloth as the filtration material. The slightly yellow filtrate was passed through the column, packed with cation-exchange resin Amberlite FCP22 ($H^+$) and then, through the column with anion-exchange resin Amberlite FPA53 ($OH^-$). The flow rate in both columns was maintained at SV=0.8 $hour^{-1}$. After completion both columns were washed with RO water to recover the steviol glycosides left in the columns and the filtrates were combined. The portion of combined solution containing 120 g total steviol glycosides was passed through seven columns, wherein each column was packed with specific macroporous polymeric adsorbent YWD-03 (Cangzhou Yuanwei, China). The first column with the size of ⅓ of the others acted as a "catcher column". The SV was around 1.0 $hour^{-1}$. After all extract was passed through the columns, the resin sequentially was washed with 1 volume of water, 2 volumes of 0.5% NaOH, 1 volume of water, 2 volumes of 0.5% HCl, and finally with water until the pH was 7.0. The "catcher column" was washed separately.

Desorption of the adsorbed steviol glycosides was carried out with 52% ethanol at SV=1.0 $hour^{-1}$. Desorption of the first "catcher column" was carried out separately and the filtrate was not mixed with the main solution obtained from other columns. Desorption of the last column also was carried out separately. The quality of extract from different columns with specific macroporous adsorbent is shown in Table 3.

TABLE 3

| Column | Steviol Glycoside Content |
|---|---|
| | Total steviol glycosides, % |
| 1 (catcher) | 55.3 |
| 2 | 92.7 |
| 3 | 94.3 |
| 4 | 96.1 |
| 5 | 96.3 |

TABLE 3-continued

Steviol Glycoside Content

| Column | Total steviol glycosides, % |
|---|---|
| 6 | 95.8 |
| 7 | 80.2 |

Eluates from second to sixth columns were combined and treated separately. The combined solution of steviol glycosides was mixed with 0.3% of activated carbon from the total volume of solution. The suspension was maintained at 25° C. for 30 min with continuous agitation. Separation of carbon was carried out on a press-filtration system. For additional decolorization the filtrate was passed through the columns packed with cation-exchange resin Amberlite FCP22 (H$^+$) followed with anion-exchange resin Amberlite FPA53 A30B (OH$^-$). The flow rate in both columns was around SV=0.5 hour$^{-1}$. The ethanol was distilled using a vacuum evaporator. The solids content in the final solution was around 15%. The concentrate was passed through the columns packed with cation-exchange resin Amberlite FCP22 (H$^+$) and anion-exchange resin Amberlite FPA53 (OH$^-$) with SV=0.5 hour$^{-1}$. After all the solution was passed through the columns, both resins were washed with RO water to recover the steviol glycosides left in the columns. The resulting refined extract was transferred to the nano-filtration device, concentrated to around 52% of solids content and spray dried to provide a highly purified mixture of steviol glycosides. The yield was 99.7 g. The mixture contained Stevioside—20.5%, Reb A—65.6%, Reb B—0.1%, Reb C—8.4%, Reb D—0.5%, Reb F—1.1%, Reb X—0.1%, Dulcoside A—0.4%, and Steviolbioside—0.4%.

The combined eluate from the last column, contained about 5.3 g of total steviol glycosides including 2.3 g Reb D and around 1.9 g Reb X (35.8% Reb X/TSG ratio). It was deionized and decolorized as discussed above and then concentrated to a 33.5% content of total solids.

The concentrate was mixed with two volumes of anhydrous methanol and maintained at 20-22° C. for 24 hours with intensive agitation.

The resulting precipitate was separated by filtration and washed with about two volumes of absolute methanol. The yield of Rebaudioside X was 1.5 g with around 80% purity.

For the further purification the precipitate was suspended in three volumes of 60% methanol and treated at 55° C. for 30 min, then cooled down to 20-22° C. and agitated for another 2 hours.

The resulting precipitate was separated by filtration and washed with about two volumes of absolute methanol and subjected to similar treatment with a mixture of methanol and water.

The yield of Rebaudioside X was 1.2 g with 97.3% purity.

In one embodiment, the aqueous alcoholic solvent comprises water and an alcohol selected from ethanol, methanol, isopropanol, butanol or combinations thereof. In a particular embodiment, the aqueous alcoholic solvent comprises water and methanol. In a more particular embodiment, the aqueous alcoholic solvent comprises water and methanol in a 1:1 (v/v) ratio.

The duration of stirring in (ii) can vary, but is generally from about 15 minutes to about 2 weeks, such as, for example, about 12 hours, about 24 hours, about 2 days, about 3 days, about 4 days, about 5 days, about 6 days, about 7 days, about 8 days, about 9 days, about 10 days, about 11 days, about 12 days, about 13 days or about 14 days.

When Rebaudioside X is combined with the aqueous alcoholic solvent, a slurry is generally formed.

In a more specific embodiment, a method for preparing Form A Rebaudioside X comprises:
(i) combining amorphous Rebaudioside X and a solvent containing water and methanol in a 1:1 (v/v) ratio to provide a slurry; and
(ii) stirring the slurry at approximately room temperature.

Material E Rebaudioside X can also be converted to Form A Rebaudioside X, which can further be converted to amorphous Rebaudioside X, if desired. In one embodiment, a method for preparing Form A Rebaudioside X comprises:
(i) mixing material E Rebaudioside X with water to provide a slurry;
(ii) heating the slurry to a temperature between about 40° C. and about 90° C.; and
(iii) removing the water from the slurry to provide Form A Rebaudioside X.

In one embodiment, the slurry can be maintained at temperatures between about 40° C. and about 60° C. for a duration from about 1 day to about 15 days, such as, for example, about 12 days.

Removal of the water in step (iii) can be accomplished by any suitable method including, for example, decantation, centrifugation, filtration, evaporation, vacuum or spray drier.

In one embodiment, Form A Rebaudioside X is in substantially pure form. In other embodiments, Form A Rebaudioside X is greater than about than about 91%, 92%, 93%, 94%, 95%, 96%, 97% or 98% pure with respect to other forms of Rebaudioside X. In one embodiment, a composition comprises Form A Rebaudioside X.

In another embodiment, Form A Rebaudioside X is provided in the absence of other forms of Rebaudioside X, i.e. 100% pure Form A Rebaudioside X with respect to other forms of Rebaudioside X.

Amorphous Rebaudioside X

In one embodiment, a method for preparing amorphous Rebaudioside X comprises (i) heating a mixture comprising solvent and Rebaudioside X, (ii) cooling the mixture and (iii) removing solvent from the mixture to provide amorphous Rebaudioside X.

Both Form A and Material E can be converted to amorphous Rebaudioside X by this process. In one embodiment, a method for preparing amorphous Rebaudioside X comprises (i) heating a mixture comprising Form A Rebaudioside X, (ii) cooling the mixture and (iii) removing solvent from the mixture to provide amorphous Rebaudioside X. In another embodiment, a method for preparing amorphous Rebaudioside X comprises (i) heating a mixture comprising Material E Rebaudioside X, (ii) cooling the mixture and (iii) removing the solvent from the mixture to provide amorphous Rebaudioside X.

The solvent can be any suitable solvent, such as, for example, water, ethanol, methanol, toluene, ethyl acetate, hexane, acetone, dioxane, tetrahydrofuran, acetonitrile, isopropanol, diethyl ether, dichloromethane, 2-butanone, 2,2,2-trifluoroethanol and combinations thereof. In a particular embodiment, the solvent comprises water. In a more particular embodiment, the solvent is water. In another embodiment, the solvent comprises ethanol. In a more particular embodiment, the solvent is ethanol.

The temperature and duration of heating in (i) will vary based on the quantity of Rebaudioside X and the identity of the solvent. In embodiments where the solvent comprises, or is water, the mixture can be heated to reflux. Suitable temperatures for refluxing will vary based on the solvent(s) used, but may be greater than about 100° C., such as, for example, about 105° C., about 110° C., about 115° C., about 120° C., about 125° C., about 130° C., about 140° C., or about 150° C. In a particular embodiment, the temperature is maintained between about 100° C. and about 130° C., such as, for example, between about 120° C. and 125° C. In certain embodiments, the temperature is raised at 1° C. per minute until the desired temperature is reached. The mixture can be maintained at the desired temperature for any duration suitable, such as, for example, between 5 minutes and 5 hours, between about 1 hour and about 5 hours, between about 1 hour and about 4 hours, between about 1 hour and about 3 hours or between about 1 hour and about 2 hours.

In embodiments where the solvent comprises, or is ethanol, the mixture can be heated to and maintained at about reflux temperatures. Suitable temperatures for reflux will vary based on the solvent(s), if any, are combined with ethanol and can be greater than or equal to about 75° C., such as for example, about 80° C., about 85° C., about 90° C., about 95° C., about 100° C., about 105° C., about 110° C., about 115° C. or about 120° C. In a particular embodiment, the temperature is maintained between about 70° C. and about 120° C., such as, for example, between about 80° C. and about 85° C. In certain embodiments, the temperature is raised at 1° C. per minute until the desired temperature is reached. The mixture can be maintained at the desired temperature for any duration suitable, such as, for example, between 5 minutes and 5 hours, between about 1 hour and about 5 hours, between about 1 hour and about 4 hours, between about 1 hour and about 3 hours or between about 1 hour and about 2 hours.

The resultant mixture of (i) can be cooled to room temperature (~25° C.) at any rate, provided that crash precipitation does not occur. In a particular embodiment, the mixture is cooled at a rate of about 1° C. per minute.

Removal of the solvent in (iii) can be accomplished by any suitable method including, for example, decantation, centrifugation, filtration, evaporation, vacuum or spray drier. The final amorphous product should be dry, i.e. substantially free of all solvent.

In a particular embodiment, a method for preparing amorphous Rebaudioside X comprises:
(i) heating a mixture comprising Form A Rebaudioside X and water;
(ii) cooling the mixture to room temperature; and
(iii) removing solvent from the mixture using a spray drier to provide amorphous Rebaudioside X.

In another particular embodiment, a method for preparing amorphous Rebaudioside X comprises:
(i) heating a mixture comprising Material E Rebaudioside X and water;
(ii) cooling the mixture to room temperature; and
(iii) removing solvent from the mixture using a spray drier to provide amorphous Rebaudioside X.

In a more particular embodiment, the temperature is maintained at about 121° C.

In another embodiment, a method for preparing amorphous Rebaudioside X comprises:
(i) heating a mixture comprising Form A Rebaudioside X and ethanol to reflux;
(ii) cooling the mixture to room temperature; and
(iii) removing the solvent from the mixture via evaporation to provide amorphous Rebaudioside X.

In another embodiment, a method for preparing amorphous Rebaudioside X comprises:
(i) heating a mixture comprising Material E Rebaudioside X and ethanol to reflux;
(ii) cooling the mixture to room temperature; and
(iii) removing the solvent from the mixture via evaporation to provide amorphous Rebaudioside X.

Figure 4:
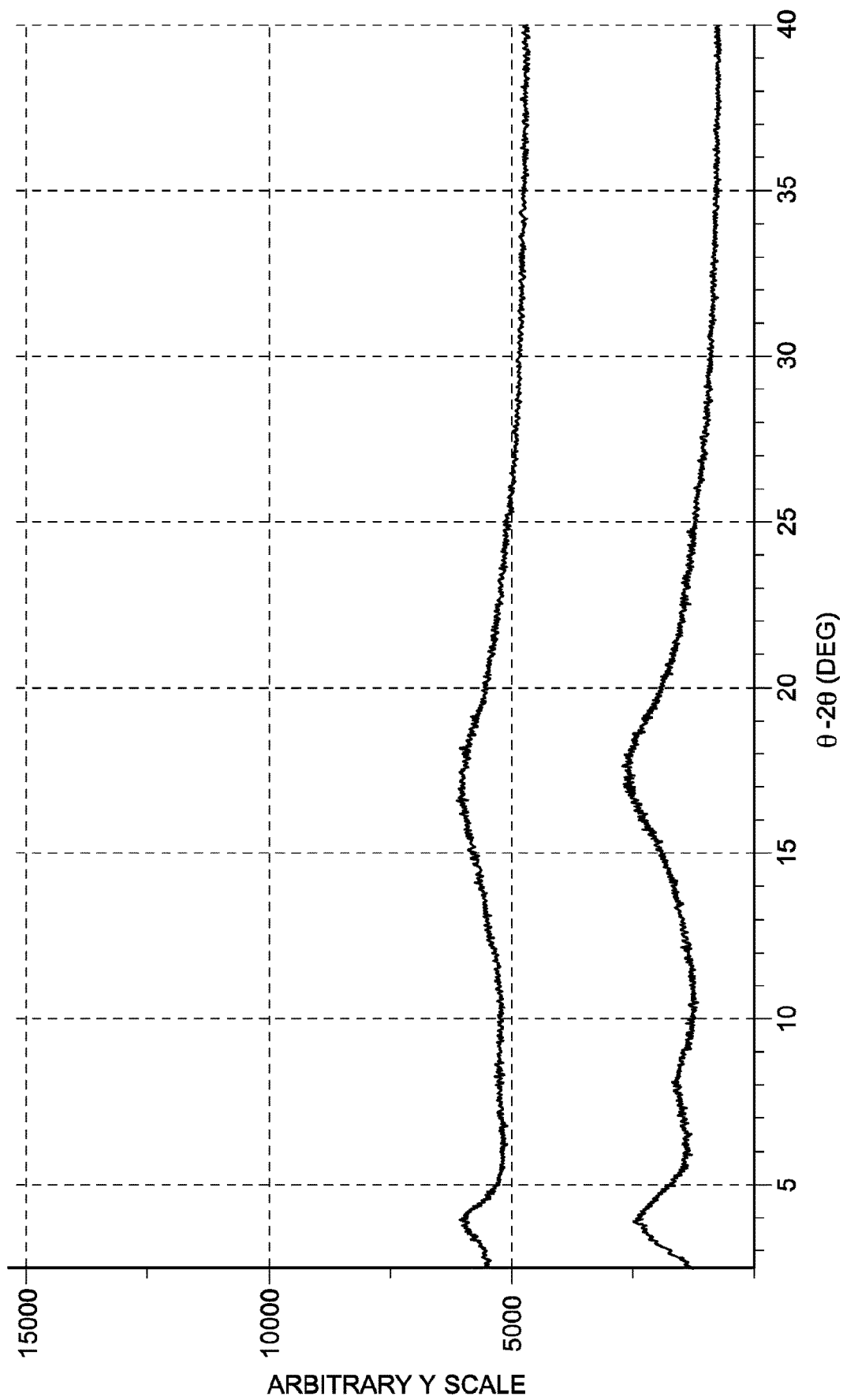
FIG. 4: illustrates the X-ray diffraction pattern of amorphous Rebaudioside X collected with Cu-Kα radiation (the wavelength used to calculate d-spacings was 1.541874 Å, a weighted average of the Cu-$K_{\alpha 1}$ and Cu-$K_{\alpha 2}$ wavelengths). Material for the top trace was prepared via the process described herein wherein the solvent was water. Material for the bottom trace was prepared via the process described herein wherein the solvent is ethanol.

The amorphous Rebaudioside X obtained by the present methods is characterized by the X-ray diffraction patterns illustrated in FIG. 4.

In exemplary embodiments, amorphous Rebaudioside X has increased aqueous solubility compared to other forms of Rebaudioside X, e.g. Form A Rebaudioside X, Form B Rebaudioside X or Material E Rebaudioside X. The approximate solubility of Form A Rebaudioside X is from about 0.1 to about 0.14%. In contrast, amorphous Rebaudioside X prepared the processes described herein exhibit approximate aqueous solubilities greater than 0.3%, such as, for example, 0.4%, 0.5%, 0.6%, about 0.7%, about 0.8%, about 0.9%, about 1.0%, about 2.0%, about 3.0%, about 4.0%, or about 5.0%.

Approximate solubility (%) is calculated as grams of Rebaudioside X per 100 mL water, e.g. 31 mg of amorphous Rebaudioside X dissolved in 1 mL water provides a solubility of 3.1%.

The approximate aqueous solubility can be determined by a solvent addition method in which a weighed sample is treated with aliquots of water. The mixture is generally vortexed and/or sonicated between additions to facilitate dissolution. Complete dissolution of the test material is determined by visual inspection. Solubility is estimated based on the total solvent used to provide complete dissolution.

In other embodiments, the method provides amorphous Rebaudioside X having a greater than about 10%, about 20%, about 30%, about 40%, about 50%, about 60%, about 70%, about 80% about 90%, about 100%, about 150%, about 200%, about 250%, about 300%, about 350%, about 400%, about 450%, about 500%, about 550% or about 600% increase in water solubility compared to Form A Rebaudioside X water solubility.

In one embodiment, the amorphous Rebaudioside X is in substantially pure form. In other embodiments, amorphous Rebaudioside X is greater than about than about 91%, 92%, 93%, 94%, 95%, 96%, 97% or 98% pure with respect to other forms of Rebaudioside X. In one embodiment, a composition comprises amorphous Rebaudioside X.

In another embodiment, amorphous Rebaudioside X is provided in the absence of other forms of Rebaudioside X, i.e. 100% pure amorphous Rebaudioside X with respect to other forms of Rebaudioside X.

Form B Rebaudioside X

A method for preparing Form B Rebaudioside A comprises:
(i) heating a mixture comprising amorphous Rebaudioside X and a solvent;
(ii) cooling the mixture; and
(iii) removing the solvent from the mixture to provide Form B Rebaudioside X.

The solvent can be water, organic solvents (e.g. alcohols), or a mixture thereof. Suitable solvents include, but are not limited to, water, ethanol, methanol, toluene, ethyl acetate, hexane, acetone, dioxane, tetrahydrofuran, acetonitrile, isopropanol, diethyl ether, dichloromethane, 2-butanone, 2,2,2-trifluoroethanol and combinations thereof. In a particular embodiment, the solvent is ethanol.

The mixture of (i), which can be a slurry, can be heated to a temperature form about 30° C. to about 100° C., such as, for example, about 40° C., about 50° C., about 60° C., about 70° C., about 80° C., about ° C. or about 100° C. In a particular embodiment, the mixture is heated to about 40°

C. In a more particular embodiment, the solvent is ethanol and the mixture is heated to about 40° C.

The duration of heating can also vary. In one embodiment, the mixture can be heated from 5 hours to about 1 week, such as, for example, about 10 hours, about 24 hours, about 2 days, about 3 days, about 4 days, about 5 days, about 6 days or about 7 days. In a particular embodiment, the solvent is ethanol and the mixture is heated to about 40° C. for about 5 days.

Removal of the solvent in (iii) can be accomplished by any suitable method including, for example, decantation, centrifugation, filtration, evaporation, vacuum or spray drier. The angular positions (two theta) of the prominent X-ray diffraction peaks are as follows (Table 2) when generated by slurrying in ethanol at 40° C.:

TABLE 2

Form B Rebaudioside X Prominent XPRD

| °2Θ | d space (Å) | Intensity (%) |
| --- | --- | --- |
| 4.20 ± 0.20 | 21.058 ± 1.053 | 100 |
| 5.17 ± 0.20 | 17.108 ± 0.689 | 41 |
| 6.47 ± 0.20 | 13.664 ± 0.435 | 78 |
| 7.40 ± 0.20 | 11.939 ± 0.331 | 54 |
| 7.92 ± 0.20 | 11.159 ± 0.289 | 99 |
| 13.40 ± 0.20 | 6.606 ± 0.100 | 70 |
| 14.46 ± 0.20 | 6.127 ± 0.085 | 57 |
| 16.08 ± 0.20 | 5.513 ± 0.069 | 65 |
| 17.48 ± 0.20 | 5.073 ± 0.058 | 91 |
| 18.15 ± 0.20 | 4.888 ± 0.054 | 71 |

Figure 7A:
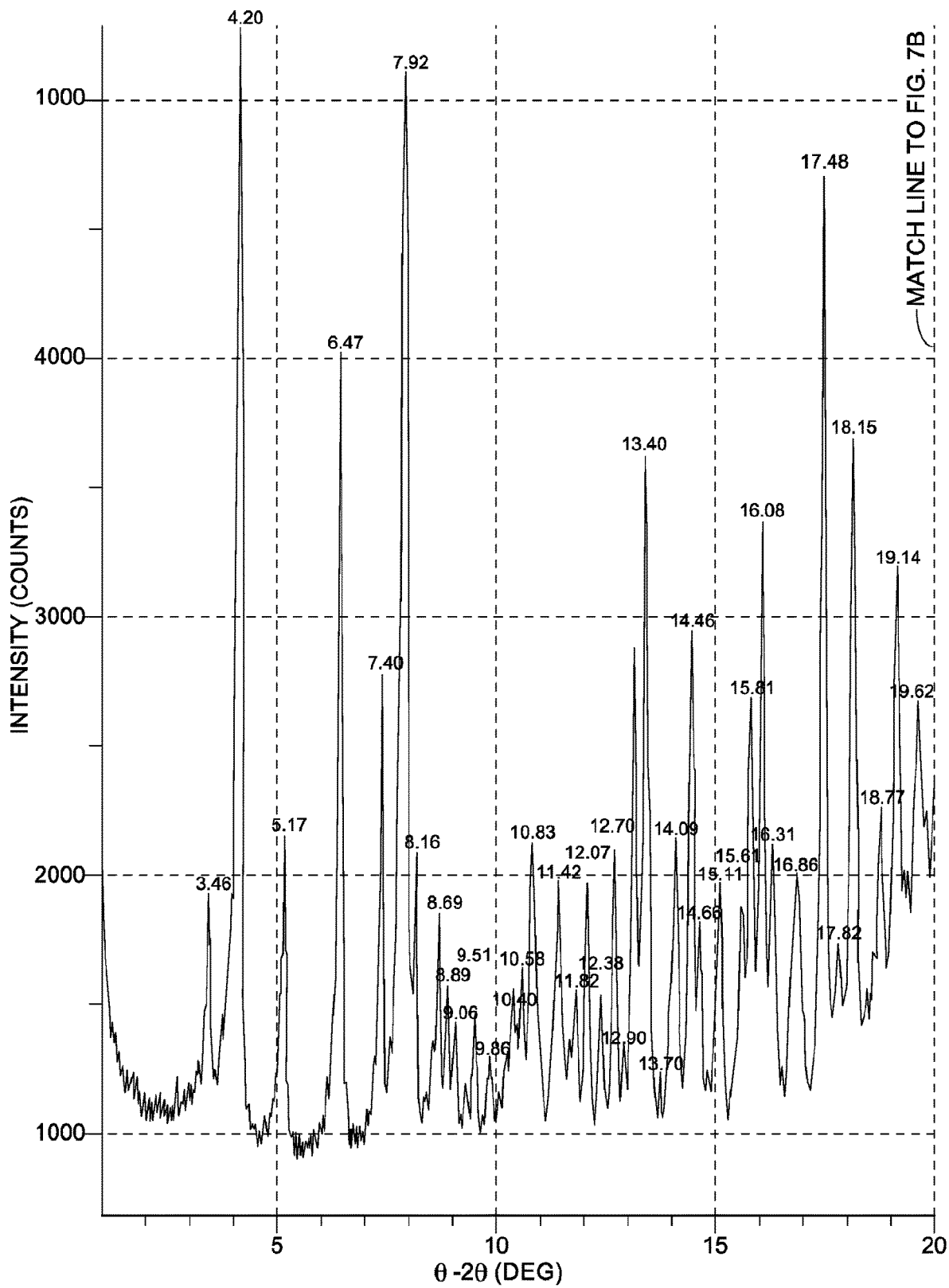
FIGS. 7A and 7B: illustrate the X-ray diffraction pattern of Form B Rebaudioside X collected with Cu-Kα radiation Cu-Kα radiation (the wavelength used to calculate d-spacings was 1.541874 Å, a weighted average of the Cu-$K_{\alpha 1}$ and Cu-$K_{\alpha 2}$ wavelengths) when generated by slurrying in ethanol at 40° C.
Figure 7B:
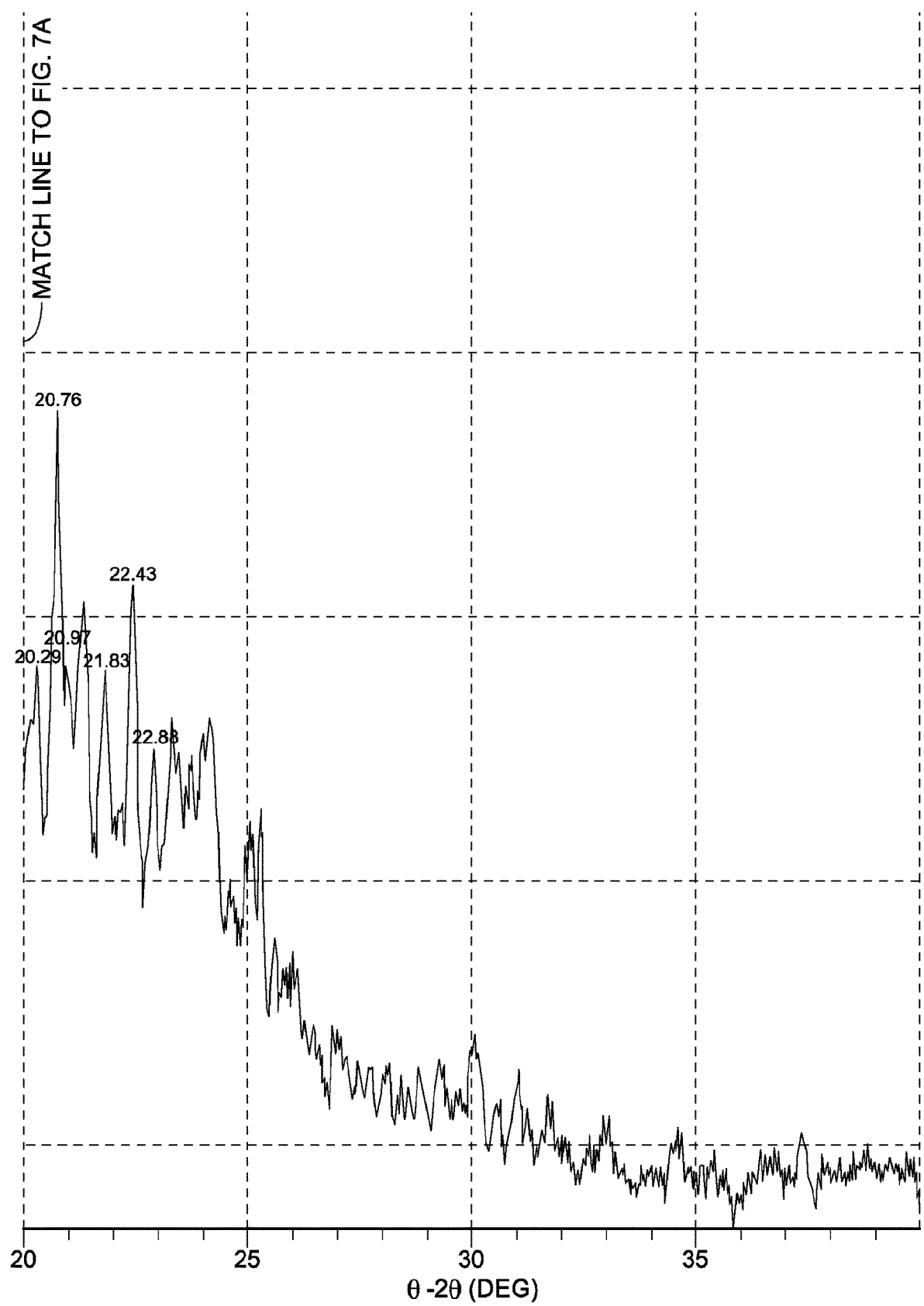

One of skill in the art will recognize that XRPD patterns of Form B Rebaudioside X produced under different conditions may display peak shifts from those of FIGS. 7A and 7B, consistent with the variable solvent/water content of the material. Form B exists as a variable solvate/hydrate.

In one embodiment, the invention is Form B Rebaudioside X in substantially pure form. In other embodiments, Form B Rebaudioside X is greater than about 91%, 92%, 93%, 94%, 95%, 96%, 97% or 98% pure with respect to other forms of Rebaudioside X.

In another embodiment, Form B Rebaudioside X is provided in the absence of other forms of Rebaudioside X, i.e. 100% pure Form B Rebaudioside X with respect to other forms of Rebaudioside X.

In one embodiment, Form B Rebaudioside X is in substantially pure form. In other embodiments, Form B Rebaudioside X is greater than about than about 91%, 92%, 93%, 94%, 95%, 96%, 97% or 98% pure with respect to other forms of Rebaudioside X. In one embodiment, a composition comprises Form B Rebaudioside X.

In another embodiment, Form B Rebaudioside X is provided in the absence of other forms of Rebaudioside X, i.e. 100% pure Form B Rebaudioside X with respect to other forms of Rebaudioside X.

Rebaudioside X Complexes

The present invention also provides certain complexes comprises Rebaudioside X and at least one other compound that, when prepared under appropriate conditions, provide greater aqueous solubility than the aqueous solubility over other forms of Rebaudioside X, including Form A Rebaudioside X. As used herein, the term "complex" means that the Rebaudioside X and the other compound(s) are in intimate contact with each other, such that the complex displays different properties, e.g. increased aqueous solubility, compared to a physical mixture (e.g. a grind) of Form A Rebaudioside X and the other compound(s).

In one embodiment, a complex comprises Rebaudioside X and at least one polyol prepared by (i) heating a mixture comprising solvent, Rebaudioside X and at least one polyol, (ii) cooling the mixture and (iii) removing the solvent from the mixture to provide a Rebaudioside X complex. In one embodiment, the Rebaudioside X complex has greater aqueous solubility than Form A Rebaudioside X.

The term "polyol", as used herein, refers to a molecule that contains more than one hydroxyl group. A polyol may be a diol, triol, or a tetraol which contains 2, 3, and 4 hydroxyl groups respectively. A polyol also may contain more than 4 hydroxyl groups, such as a pentaol, hexaol, heptaol, or the like, which contain 5, 6, or 7 hydroxyl groups, respectively. Additionally, a polyol also may be a sugar alcohol, polyhydric alcohol, or polyalcohol which is a reduced form of carbohydrate, wherein the carbonyl group (aldehyde or ketone, reducing sugar) has been reduced to a primary or secondary hydroxyl group.

Non-limiting examples of polyols in some embodiments include erythritol, maltitol, mannitol, sorbitol, lactitol, xylitol, isomalt, propylene glycol, glycerol (glycerin), threitol, galactitol, palatinose, reduced isomalto-oligosaccharides, reduced xylo-oligosaccharides, reduced gentio-oligosaccharides, reduced maltose syrup, reduced glucose syrup, and sugar alcohols or any other carbohydrates capable of being reduced.

In certain embodiments, the mixture of Rebaudioside and at least one polyol is heated until the mixture is visibly clear by inspection, i.e. a solution with no visible solid particulates. In a particular embodiment, the mixture is heated to a temperature between about 100° C. and 120° C. The solvent can vary but is preferably water. In one embodiment, Rebaudioside X and the at least one polyol may be in a weight of about 1:1 to about 1:20. In a particular embodiment, the Rebaudioside X and at least one polyol are present in a weight ratio of about 1:1. In a particular embodiment, freeze-drying or spray drying is used in (iii) to remove the solvent from the mixture. The final product should be dry, i.e. substantially free of solvent.

In a specific embodiment, a complex comprises Rebaudioside X and erythritol, wherein the complex has greater aqueous solubility than Form A Rebaudioside X. In certain cases, the complex also has greater aqueous solubility compared to a physical mixture of Rebaudioside X and erythritol.

In another specific embodiment, a method for preparing a Rebaudioside X complex comprises:

(i) heating a mixture comprising water, Rebaudioside X and erythritol;

(ii) cooling the mixture to approximately room temperature; and (iii) freeze-drying the mixture to provide a Rebaudioside X complex.

In a particular embodiment, the weight ratio of Rebaudioside X to erythritol is about 1:1, and the mixture in (i) is heated until it is visibly clear. Not wishing to be bound by theory, it is believed that the complex provides superior aqueous solubility properties over the physical mixture of Form A Rebaudioside X and erythritol because the erythritol present during the heating/cooling steps may act to disrupt formation of crystalline polymorphs of Rebaudioside X (e.g. Form A).

In one embodiment, a complex comprises Rebaudioside X and maltodextrin prepared by (i) heating a mixture comprising solvent, Rebaudioside X and maltodextrin, (ii) cooling the mixture and (iii) removing the solvent from the mixture to provide a Rebaudioside X complex. In a particular embodiment, the Rebaudioside X complex has greater aqueous solubility than the Form A Rebaudioside X.

In certain embodiments, the mixture of Rebaudioside and maltodextrin is heated until the mixture is visibly clear by inspection, i.e. a solution with no visible solid particulates. In a particular embodiment, the mixture is heated to reflux. In another embodiment, the mixture is heated to a temperature from about 100° C. and about 120° C. The solvent can vary but is preferably water. Rebaudioside X and maltodextrin may be in a weight ratio of about 1:1 to about 1:20. In a particular embodiment, the weight ratio of Rebaudioside X and maltodextrin is about 1:1. In a particular embodiment, freeze-drying or spray drying is used in (iii) to remove the solvent from the mixture. The final product should be dry, i.e. substantially free of solvent.

In another specific embodiment, a complex comprises Rebaudioside X and maltodextrin, wherein the complex has greater aqueous solubility than Form A Rebaudioside X. In certain cases, the complex also has greater aqueous solubility compared to a physical mixture of Rebaudioside X and maltodextrin.

In another specific embodiment, a method for preparing a Rebaudioside X complex comprises:

(i) heating a mixture comprising water, Rebaudioside X and maltodextrin;

(ii) cooling the mixture to approximately room temperature; and (iii) freeze-drying the mixture to provide a Rebaudioside X complex.

In a particular embodiment, the weight ratio of Rebaudioside X to maltodextrin is about 1:1, and the mixture in (i) is heated until it is visibly clear. Not wishing to be bound by theory, it is believed that the complex provides superior aqueous solubility properties over the physical mixture of Form A Rebaudioside X and maltodextrin because the maltodextrin present during the heating/cooling steps may act to disrupt formation of crystalline polymorphs of Rebaudioside X (e.g. Form A).

In one embodiment, a complex comprises Rebaudioside X and at least one cyclodextrin prepared by (i) heating a mixture comprising solvent, Rebaudioside X and at least one cyclodextrin, (ii) cooling the mixture and (iii) removing the solvent from the mixture to provide a Rebaudioside X complex with greater aqueous solubility than Form A Rebaudioside X alone.

Cyclodextrins are cyclic oligosaccharides having at least six glucopyranose units. They generally form a toroid shape with an interior cavity that is less hydrophilic than the cyclodextrin exterior. They may form inclusion complexes and, as such, host other molecules. Cyclodextrins may change the physico-chemical properties of such other molecules, such as the solubility. As used herein, "cyclodextrin" refers to any cyclodextrin that increases the solubility of Rebaudioside X.

Not wishing to be bound by theory, it is believed that the cyclodextrin and Rebaudioside A may form an inclusion complex, which provides superior aqueous solubility compared to Form A Rebaudioside X alone. The term "inclusion complex" is understood to mean that Rebaudioside X and cyclodextrin are in intimate contact with one another, such as a complete or partial association or contact (e.g. hydrophobic interactions) between Rebaudioside X and cyclodextrin, such that Rebaudioside X resides in a cyclodextrin cavity.

In one embodiment, a complex comprises Rebaudioside X and at least one cyclodextrin, wherein the aqueous solubility of the complex is greater than the solubility of Form A Rebaudioside X alone.

The at least one cyclodextrin can be, but is not limited to, α-cyclodextrin, β-cyclodextrin, γ-cyclodextrin, or a derivative thereof. In a particular embodiment, the at least one cyclodextrin is γ-cyclodextrin.

Commercially available cyclodextrin may be used, for example, those sold by the companies Cyclolab Ltd., those sold under the trade name TRAPPSOL® by CDT, Inc., those sold under the trade name CAVAMAX® by Wacker, those sold under the tradenames KLEPTOSE® and CRYSMEB® by Roquette, and those sold under the tradename CAPTISOL® by CYDEX Pharmaceuticals.

Cyclodextrin derivatives may have modified or substituted hydroxyl groups located on the exterior or interior cavity of the cyclodextrin. Non-limiting examples of such cyclodextrin derivatives include alkylated cyclodextrins; hydroxyalkylated cyclodextrins; ethylcarboxymethyl cyclodextrins; sulfonated and sulfoalkylether cyclodextrins; cyclodextrins substituted with ammonium groups, phosphate groups, and hydroxyl groups, and salts thereof; fluorinated cyclodextrins; and cyclodextrins substituted with saccharides. Derivatives are generally prepared by modifying or substituting the hydroxyl groups located on the exterior or interior of the cyclodextrin. The modifications may be made to increase the aqueous solubility and stability of the inclusion complex. Modifications may also be made to alter the physical characteristics of the complex. Modifications of those types and others are well known in the art.

In one embodiment, a complex comprises Rebaudioside X and γ-cyclodextrin. In some embodiments, the ratio of Rebaudioside X to cyclodextrin ranges from about 1:1 to about 1:20. For example, the ratio may range from about 1:1 to about 1:19, or from about 1:1 to about 1:15 or from about 1:1 to about 1:9, or from about 1:1 to about 1:8, or from about 1:1 to about 1:7, or from about 1:1 to about 1:6, or from about 1:1 to about 1:5, or from about 1:1 to about 1:4.

In one embodiment, a method of preparing a Rebaudioside X complex comprises (i) heating a mixture comprising Rebaudioside X, at least one cyclodextrin and water; (ii) cooling the mixture to approximately room temperature and (iii) freeze-drying the mixture to provide a Rebaudioside X complex.

The amount of Rebaudioside X and the at least one cyclodextrin can vary. Generally, Rebaudioside X and the at least one cyclodextrin are provided in a weight ratio from about 1:4 to about 1:20. In a particular embodiment, the weight ratio of Rebaudioside X to the at least one cyclodextrin is from about 1:1 to about 1:4, such as about 1:1, about 1:2, about 1:3 and about 1:4. In a more particular embodiment, the at least one cyclodextrin is γ-cyclodextrin, and the weight ratio of Rebaudioside X to γ-cyclodextrin is from about 1:1 to about 1:4. In an further particular embodiment, the Rebaudioside X is substantially pure Form A Rebaudioside X, the at least one cyclodextrin is γ-cyclodextrin, and the weight ratio of Rebaudioside X to γ-cyclodextrin is from about 1:1 to about 1:4.

The solvent in (ii) can vary. Suitable solvents include, but are not limited to, water, methanol, ethanol or combinations thereof. The mixture should generally be heated until all the contents/materials are dissolved and the mixture is a clear solution. Suitable temperatures will depend on the amount of materials in the mixture and the identity of the solvent. In certain embodiments, the solvent is water and the mixture is heated to reflux. In other embodiments, the mixture is heated to a temperature from 100° C. to about 120° C.

The solvent can be removed from the mixture in (iii) by any suitable method, such as, for example, freeze-drying or spray drying. In a particular embodiment, the solvent is removed by freeze-drying. In an exemplary procedure, Rebaudioside X (1.0 g) and γ-cyclodextrin (4.0 g) are added to water (100 mL). The mixture is heated until all materials are dissolved (visual inspection for clarity). In one embodiment, the mixture is heated to reflux. In another embodiment, the mixture is heated to a temperature from 100° C. to about 120° C. The mixture can then be cooled to room temperature and freeze-dried. The mixture can be freeze-dried for any suitable time frame, such as, for example, from about 1 to about 3 days.

Any form of Rebaudioside X can be used in any of the complexes described herein, including Form A, Form B, Material E, amorphous and mixtures thereof.

The Rebaudioside X complexes can further contain other terpene glycosides in addition to Rebaudioside X. Suitable terpene glycosides include, but are not limited to, rebaudioside A; rebaudioside B; rebaudioside C; rebaudioside D; rebaudioside E; rebaudioside F; stevioside; steviolbioside; dulcoside A; rubusoside; steviol; steviol 13 O-β-D-glycoside; suavioside A; suavioside B; suavioside G; suavioside H; suavioside I; suavioside J; isosteviol; 13-[(2-O-(3-O-α-D-glucopyranosyl)-β-D-glucopyranosyl-3-β-β-D-glucopyranosyl-β-D-glucopyranosyl)oxy]kaur-16-en-18-oic acid β-D-glucopyranosyl ester; 13-[(2-O-β-D-glucopyranosyl-3-O-(4-O-α-D-glucopyranosyl)-β-D-glucopyranosyl-β-D-glucopyranosyl)oxy]kaur-16-en-18-oic acid β-D-glucopyranosyl ester; 13-[(3-O-β-D-glucopyranosyl-β-D-glucopyranosyl)oxy]kaur-16-en-18-oic acid β-D-glucopyranosyl ester; 13-hydroxy-kaur-16-en-18-oic acid β-D-glucopyranosyl ester; 13-methyl-16-oxo-17-norkauran-18-oic acid β-D-glucopyranosyl ester; 13-[(2-O-β-D-glucopyranosyl-3-O-β-D-glucopyranosyl-β-D-glucopyranosyl)oxy]kaur-15-en-18-oic acid β-D-glucopyranosyl ester; 13-[(2-O-β-D-glucopyranosyl-3-O-β-D-glucopyranosyl-β-D-glucopyranosyl)oxy]kaur-15-en-18-oic acid; 13-[(2-O-β-D-glucopyranosyl-3-O-β-D-glucopyranosyl]-β-D-glucopyranosyl)oxy]-17-hydroxy-kaur-15-en-18-oic acid β-D-glucopyranosyl ester; 13-[(2-O-β-D-glucopyranosyl-3-O-β-D-glucopyranosyl-β-D-glucopyranosyl)oxy]-16-hydroxy kauran-18-oic acid β-D-glucopyranosyl ester; 13-[(2-O-β-D-glucopyranosyl-3-O-β-D-glucopyranosyl-β-D-glucopyranosyl)oxy]-16-hydroxy kauran-18-oic acid; 1-[13-hydroxykaur-16-en-18-oate]β-D-glucopyranuronic acid; 13-[(2-O-β-D-glucopyranosyl-β-D-glucopyranosyl)oxy]-17-hydroxy-kaur-15-en-18-oic acid β-D-glucopyranosyl ester; 13-[(2-O-α-L-rhamnopyranosyl-3-O-β-D-glucopyranosyl-β-D-glucopyranosyl)oxy]kaur-16-en-18-oic acid-(2-O-β-D-glucopyranosyl-β-D-glucopyranosyl) ester; 13-[(2-O-β-D-glucopyranosyl-β-D-glucopyranosyl)oxy]-17-oxo-kaur-15-en-18-oic acid β-D-glucopyranosyl ester; 13-[(2-O-β-D-glucopyranosyl-β-D-glucopyranosyl)oxy]-17-oxo-kaur-15-en-18-oic acid β-D-glucopyranosyl ester; 13-[(2-O-(6-O-β-D-glucopyranosyl)-β-D-glucopyranosyl-β-D-glucopyranosyl)oxy]kaur-16-en-18-oic acid β-D-glucopyranosyl ester; 13-[(2-O-β-D-glucopyranosyl-3-O-β-D-fructofuranosyl-β-D-glucopyranosyl)oxy]kaur-16-en-18-oic acid β-D-glucopyranosyl ester; 13-[(2-O-β-D-glucopyranosyl-β-D-glucopyranosyl)oxy]kaur-16-en-18-oic acid-(6-O-β-D-xylopyranosyl-β-D-glucopyranosyl) ester; 13-[(2-O-β-D-glucopyranosyl-β-D-glucopyranosyl)oxy]kaur-16-en-18-oic acid-(4-O-(2-O-α-D-glucopyranosyl)-α-D-glucopyranosyl-β-D-glucopyranosyl) ester; 13-[(2-O-β-D-glucopyranosyl-3-O-β-D-glucopyranosyl-β-D-glucopyranosyl)oxy]kaur-16-en-18-oic acid-(2-O-6-deoxy-β-D-glucopyranosyl-β-D-glucopyranosyl) ester; 13-[(2-O-β-D-glucopyranosyl-β-D-glucopyranosyl)oxy]kaur-15-en-18-oic acid β-D-glucopyranosyl ester; 13-[(2-O-β-D-glucopyranosyl-3-O-β-D-xylopyranosyl-β-D-glucopyranosyl)oxy]kaur-16-en-18-oic acid β-D-glucopyranosyl ester; 13-[(2-O-β-D-xylopyranosyl-β-D-glucopyranosyl)oxy]kaur-16-en-18-oic acid β-D-glucopyranosyl ester; 13-[(3-O-β-D-glucopyranosyl-β-D-glucopyranosyl)oxy]kaur-16-en-18-oic acid β-D-glucopyranosyl ester; 13-[(2-O-6-deoxy-β-D-glucopyranosyl-3-O-β-D-glucopyranosyl-β-D-glucopyranosyl)oxy]kaur-16-en-18-oic acid β-D-glucopyranosyl ester; 13-[(2-O-6-deoxy-β-D-glucopyranosyl-β-D-glucopyranosyl)oxy]kaur-16-en-18-oic acid β-D-glucopyranosyl ester mogroside E; mogroside I A; mogroside I E; mogroside II A; mogroside II $A_1$; mogroside II B; mogroside II E; mogroside III; mogroside III $A_2$; mogroside IV; mogroside IV A; mogroside V; mogroside VI; 11-oxomogroside; 11-oxomogroside I A; 11-oxomogroside I $A_1$; 20-hydroxy-11-oxomogroside I $A_1$; 11-oxomogroside II $A_1$; 7-oxomogroside II E; 11-oxomogroside II E; 11-deoxymogroside III; 11-oxomogroside IV A; 7-oxomogroside V; 11-oxo-mogroside V; mogrol; 11-oxo-mogrol; siamenoside; siamenoside-1; isomogroside; isomogroside V; and polymorphic and amorphous forms thereof.

In at least one embodiment, the aqueous solubility of the Rebaudioside X complexes is increased compared to the aqueous solubility of Form A Rebaudioside X. For example, the aqueous solubility may be range from 0.1% to 7%, for example from 0.2% to 7%, such as from 0.2% to 5%. In some embodiments, the aqueous solubility may range from 0.5% to 7%, such as from 1% to 5%, or from 2% to 5%, or from 3% to 5%, or from 4% to 5%.

The Rebaudioside X complexes can be used as the sweet component (i.e. the material that provides sweetness) in a sweetener composition. In addition, sweetened compositions, e.g. beverages, can comprise the Rebaudioside X complexes provided herein.

Sweetener Compositions and Methods of Making the Same

Sweetener composition, as used herein, means a composition that contains at least one sweet component in combination with at least one other substance. The at least one other substance may be, for example, a functional ingredient and/or an additive. The sweetener compositions of the present invention are dry powders.

Sweetenable composition, as used herein, means a substance that is desirable to sweeten, including ingested substances and substances that are contacted with the mouth but not eaten or swallowed. Sweetenable compositions may be unsweetened, i.e. lack any sweetener component, or sweetened, i.e. already contain a sweetener component.

Sweetened composition, as used herein, means substances that contain both a sweetenable composition and a sweetener or sweetener composition.

For example, a beverage with no sweetener component is a type of sweetenable composition. A sweetener composition comprising amorphous Rebaudioside X can be added to the unsweetened beverage, thereby providing a sweetened beverage. The sweetened beverage is a type of sweetened composition.

In another example, a beverage that contains a non-Rebaudioside X sweetener is a type of sweetenable composition. A sweetener composition comprising amorphous Rebaudioside X can be added to a beverage that contains a non-Rebaudioside X sweetener, thereby providing a sweetened beverage. The sweetened beverage is a type of sweetened composition.

In the sweetener compositions of the forgoing embodiments, Rebaudioside X can be any form of Rebaudioside X described herein (e.g. Form A Rebaudioside X, amorphous Rebaudioside X, Form B Rebaudioside X). In another embodiment, Rebaudioside X can be provided as a Rebaudioside X complexes.

In a particular embodiment, the sweetener compositions comprise amorphous Rebaudioside, which X can be provided in the presence or absence of other compounds, i.e. amorphous Rebaudioside X can be part of a composition containing one or more compounds that are not amorphous Rebaudioside X.

In one embodiment, Rebaudioside X is provided in a composition containing or more additional compounds. The composition may contain Rebaudioside X in an amount greater than about 80% by weight on a dry basis, such as, for example, greater than about 85%, greater than about 90%, greater than about 91%, greater than about 92%, greater than about 93%, greater than about 94%, greater than about 95%, greater than about 96%, greater than about 97%, greater than about 98% or greater than about 99% amorphous Rebaudioside X by weight on a dry basis.

In a particular embodiment, Rebaudioside X is provided as a component of partially purified *Stevia* extract. For example, the *Stevia* extract may contain Rebaudioside X in an amount greater than about 80% by weight on a dry basis, such as, for example, greater than about 85%, greater than about 90%, greater than about 91%, greater than about 92%, greater than about 93%, greater than about 94%, greater than about 95%, greater than about 96%, greater than about 97%, greater than about 98% or greater than about 99% Rebaudioside X by weight on a dry basis.

In another particular embodiment, Rebaudioside X is provided as a component of a steviol glycoside mixture. The identities of steviol glycosides are known in the art and include, but are not limited to, steviol monoside, rubososide, steviolbioside, stevioside, Rebaudioside A, Rebaudioside B, Rebaudioside C, Rebaudioside D, Rebaudioside E, Rebaudioside F and dulcoside A. The steviol glycoside mixture may contain from about 5% to about 99% Rebaudioside X by weight on a dry basis. For example, a steviol glycoside mixture may contain greater than about 10%, greater than about 20%, greater than about 30%, greater than about 40%, greater than about 50%, greater than about 60%, greater than about 70%, greater than about 80% or greater than about 90% Rebaudioside X by weight on a dry basis. In still further embodiments, the steviol glycoside mixture may contain greater than about 90%, for example, greater than about 91%, greater than about 92%, greater than about 93%, greater than about 94%, greater than about 95%, greater than about 96%, greater than about 97%, greater than about 98% or greater than about 99% Rebaudioside X by weight on a dry basis.

It is contemplated that a composition can contain substantial quantities of non-Rebaudioside X compounds while the Rebaudioside X within the composition is substantially pure amorphous Rebaudioside X, i.e. does not contain greater than about 10% non-amorphous Rebaudioside X. For example, a composition may contain amorphous Rebaudioside X in an amount greater than about 80% by weight on a dry basis, wherein the amorphous Rebaudioside X is substantially pure. In another example, Rebaudioside X may be present in a *Stevia* extract in an amount of about 80% by weight on a dry basis wherein the Rebaudioside X is 100% pure amorphous Rebaudioside X with respect to other forms of Rebaudioside X.

In one embodiment, amorphous Rebaudioside X can be used as the sole sweetener in the sweetener composition, i.e. amorphous Rebaudioside X is the only compound present in the sweetener composition that provides sweetness. In another embodiment, amorphous Rebaudioside X is one of two or more sweetener compounds present in the sweetener composition.

In another embodiment, a Rebaudioside X complex can be used as the sole sweetener component in the sweetener composition, i.e. the complex is the only material present in the sweetener composition that provides sweetness. In other embodiments, other sweetener compounds can be present in the sweetener composition in addition to the Rebaudioside X complex.

The sweetness of a given composition is typically measured with reference to a solution of sucrose. See generally "A Systematic Study of Concentration-Response Relationships of Sweeteners," G. E. DuBois, D. E. Walters, S. S. Schiffman, Z. S. Warwick, B. J. Booth, S. D. Pecore, K. Gibes, B. T. Carr, and L. M. Brands, in *Sweeteners: Discovery, Molecular Design and Chemoreception*, D. E. Walters, F. T. Orthoefer, and G. E. DuBois, Eds., American Chemical Society, Washington, D.C. (1991), pp 261-276.

The amount of sucrose in a reference solution may be described in degrees Brix (° Bx). One degree Brix is 1 gram of sucrose in 100 grams of solution and represents the strength of the solution as percentage by weight (% w/w) (strictly speaking, by mass). In one embodiment, a sweetener composition contains amorphous Rebaudioside X in an amount effective to provide sweetness equivalent from about 0.50 to 14 degrees Brix of sugar when present in a sweetened composition, such as, for example, from about 5 to about 11 degrees Brix, from about 4 to about 7 degrees Brix, or about 5 degrees Brix. In another embodiment, amorphous Rebaudioside X is present in an amount effective to provide sweetness equivalent to about 10 degrees Brix when present in a sweetened composition.

The sweetness of a non-sucrose sweetener can also be measured against a sucrose reference by determining the non-sucrose sweetener's sucrose equivalence. Typically, taste panelists are trained to detect sweetness of reference sucrose solutions containing between 1-15% sucrose (w/v). Other non-sucrose sweeteners are then tasted at a series of dilutions to determine the concentration of the non-sucrose sweetener that is as sweet as a given percent sucrose reference. For example, if a 1% solution of a sweetener is as sweet as a 10% sucrose solution, then the sweetener is said to be 10 times as potent as sucrose.

In one embodiment, amorphous Rebaudioside X is present in a sweetener composition in an amount effective to provide a sucrose equivalence of greater than about 10% (w/v) when present in a sweetened composition, such as, for example, greater than about 11%, greater than about 12%, greater than about 13% or greater than about 14%.

In another embodiment, a Rebaudioside X complex is present in a sweetener composition in an amount effective to provide a sucrose equivalence of greater than about 10% (w/v) when present in a sweetened composition, such as, for example, greater than about 11%, greater than about 12%, greater than about 13% or greater than about 14%.

In some embodiments, sweetener compositions contain one or more additional sweeteners. The additional sweetener can be any type of sweetener, for example, a natural, non-natural, or synthetic sweetener. In at least one embodiment, the at least one additional sweetener is chosen from natural sweeteners other than *Stevia* sweeteners. In another embodiment, the at least one additional sweetener is chosen from synthetic high potency sweeteners.

For example, the at least one additional sweetener may be a carbohydrate sweetener. Non-limiting examples of suitable carbohydrate sweeteners include sucrose, fructose, glucose, erythritol, maltitol, lactitol, sorbitol, mannitol, xylitol, D-tagatose, trehalose, galactose, rhamnose, cyclodextrin (e.g., α-cyclodextrin, β-cyclodextrin, and γ-cyclodextrin), ribulose, threose, arabinose, xylose, lyxose, allose, altrose, mannose, idose, lactose, maltose, invert sugar, isotrehalose, neotrehalose, palatinose or isomaltulose, erythrose, deoxyribose, gulose, idose, talose, erythrulose, xylulose, psicose, turanose, cellobiose, glucosamine, mannosamine, fucose, fuculose, glucuronic acid, gluconic acid, glucono-lactone, abequose, galactosamine, xylo-oligosaccharides (xylotriose, xylobiose and the like), gentio-oligosaccharides (gentiobiose, gentiotriose, gentiotetraose and the like), galacto-oligosaccharides, sorbose, ketotriose (dehydroxyacetone), aldotriose (glyceraldehyde), nigero-oligosaccharides, fructooligosaccharides (kestose, nystose and the like), maltotetraose, maltotriol, tetrasaccharides, mannan-oligosaccharides, malto-oligosaccharides (maltotriose, maltotetraose, maltopentaose, maltohexaose, maltoheptaose and the like), dextrins, lactulose, melibiose, raffinose, rhamnose, ribose, isomerized liquid sugars such as high fructose corn/starch syrup (HFCS/HFSS) (e.g., HFCS55, HFCS42, or HFCS90), coupling sugars, soybean oligosaccharides, glucose syrup and combinations thereof.

In other embodiments, the additional sweetener is a carbohydrate sweetener selected from the group consisting of glucose, fructose, sucrose and combinations thereof.

The Rebaudioside X and carbohydrate sweetener may be present in the sweetener composition in any weight ratio, such as, for example, from about 0.001:14 to about 1:0.01, such as, for example, about 0.06:6. Carbohydrates are present in the sweetener composition in an amount effective to provide a concentration from about 100 ppm to about 140,000 ppm when present in a sweetened composition, such as, for example, a beverage.

In yet other embodiments, the at least one additional sweetener is a synthetic sweetener. As used herein, the phrase "synthetic sweetener" refers to any composition which is not found naturally in nature and characteristically has a sweetness potency greater than sucrose, fructose, or glucose, yet has less calories. Non-limiting examples of synthetic high-potency sweeteners suitable for embodiments of this disclosure include sucralose, potassium acesulfame, acesulfame acid and salts thereof, aspartame, alitame, saccharin and salts thereof, neohesperidin dihydrochalcone, cyclamate, cyclamic acid and salts thereof, neotame, advantame, glucosylated steviol glycosides (GSGs) and combinations thereof. The synthetic sweetener is present in the sweetener composition in an amount effective to provide a concentration from about 0.3 ppm to about 3,500 ppm when present in a sweetened composition, such as, for example, a beverage.

In still other embodiments, the additional sweetener can be a natural high potency sweetener. Suitable natural high potency sweeteners include, but are not limited to, rebaudioside A, rebaudioside B, rebaudioside C, rebaudioside D, rebaudioside E, rebaudioside F, rebaudioside I, rebaudioside H, rebaudioside L, rebaudioside K, rebaudioside J, rebaudioside M, rebaudioside N, rebaudioside O, dulcoside A, dulcoside B, rubusoside, *stevia*, stevioside, mogroside IV, mogroside V, Luo Han Guo sweetener, siamenoside, monatin and its salts (monatin SS, RR, RS, SR), curculin, glycyrrhizic acid and its salts, thaumatin, monellin, mabinlin, brazzein, hernandulcin, phyllodulcin, glycyphyllin, phloridzin, trilobatin, baiyunoside, osladin, polypodoside A, pterocaryoside A, pterocaryoside B, mukurozioside, phlomisoside I, periandrin I, abrusoside A, steviolbioside and cyclocarioside I. The natural high potency sweetener can be provided as a pure compound or, alternatively, as part of an extract. For example, rebaudioside A can be provided as a sole compound or as part of a *Stevia* extract. The natural high potency sweetener is present in the sweetener composition in an amount effective to provide a concentration from about 0.1 ppm to about 3,000 ppm when present in a sweetened composition, such as, for example, a beverage.

The sweetener compositions can be customized to obtain a desired calorie content. In one embodiment, the sweetener composition is "full-calorie", such that the composition imparts the desired sweetness when added to a sweetenable composition (such as, for example, a beverage) and the sweetened composition has about 120 calories per 8 oz serving.

In another embodiment, the sweetener composition is "mid-calorie", such that the composition imparts the desired sweetness when added to a sweetenable composition (such as, for example, as beverage) and less than about 60 calories per 8 oz serving.

In another embodiment, the sweetener composition is "low-calorie", such that the composition imparts the desired sweetness when added to a sweetenable composition (such as, for example, as beverage) and the sweetened composition has less than about 40 calories per 8 oz serving.

In yet other embodiments, the sweetener compositions can be "zero-calorie", such that the composition imparts the desired sweetness when added to a sweetenable composition (such as, for example, a beverage) and the sweetened composition has less than about 5 calories per 8 oz. serving.

Additives

In addition to Rebaudioside X and, optionally, other sweeteners, the sweetener compositions of the present invention can optionally include additional additives, detailed herein below. In some embodiments, the sweetener composition contains additives including, but not limited to, carbohydrates, polyols, amino acids and their corresponding salts, poly-amino acids and their corresponding salts, sugar acids and their corresponding salts, nucleotides, organic acids, inorganic acids, organic salts including organic acid salts and organic base salts, inorganic salts, bitter compounds, flavorants and flavoring ingredients, astringent compounds, proteins or protein hydrolysates, surfactants, emulsifiers, weighing agents, gums, antioxidants, colorants, flavonoids, alcohols, polymers and combinations thereof. In some embodiments, the additives act to improve the temporal and flavor profile of the sweetener to provide a sweetener composition with a taste similar to sucrose.

In one embodiment, the sweetener compositions comprise one or more polyols.

In certain embodiments, the polyol is present in the sweetener composition in an amount effective to provide a concentration from about 100 ppm to about 250,000 ppm when present in a sweetened composition, such as, for example, a beverage. In other embodiments, the polyol is present in the sweetener composition in an amount effective to provide a concentration from about 400 ppm to about 80,000 ppm when present in a sweetened composition, such as, for example, from about 5,000 ppm to about 40,000 ppm.

In other embodiments, Rebaudioside X and the polyol are present in the sweetener composition in a weight ratio from about 1:1 to about 1:800, such as, for example, from about 1:4 to about 1:800, from about 1:20 to about 1:600, from about 1:50 to about 1:300 or from about 1:75 to about 1:150.

Suitable amino acid additives include, but are not limited to, aspartic acid, arginine, glycine, glutamic acid, proline, threonine, theanine, cysteine, cystine, alanine, valine, tyrosine, leucine, arabinose, trans-4-hydroxyproline, isoleucine, asparagine, serine, lysine, histidine, ornithine, methionine, carnitine, aminobutyric acid (α-, β-, and/or δ-isomers), glutamine, hydroxyproline, taurine, norvaline, sarcosine, and their salt forms such as sodium or potassium salts or acid salts. The amino acid additives also may be in the D- or L-configuration and in the mono-, di-, or tri-form of the same or different amino acids. Additionally, the amino acids may be α-, β-, γ- and/or δ-isomers if appropriate. Combinations of the foregoing amino acids and their corresponding salts (e.g., sodium, potassium, calcium, magnesium salts or other alkali or alkaline earth metal salts thereof, or acid salts) also are suitable additives in some embodiments. The amino acids may be natural or synthetic. The amino acids also may be modified. Modified amino acids refers to any amino acid wherein at least one atom has been added, removed, substituted, or combinations thereof (e.g., N-alkyl amino acid, N-acyl amino acid, or N-methyl amino acid). Non-limiting examples of modified amino acids include amino acid derivatives such as trimethyl glycine, N-methyl-glycine, and N-methyl-alanine. As used herein, modified amino acids encompass both modified and unmodified amino acids. As used herein, amino acids also encompass both peptides and polypeptides (e.g., dipeptides, tripeptides, tetrapeptides, and pentapeptides) such as glutathione and L-alanyl-L-glutamine. Suitable polyamino acid additives include poly-L-aspartic acid, poly-L-lysine (e.g., poly-L-α-lysine or poly-L-ε-lysine), poly-L-ornithine (e.g., poly-L-□α-ornithine or poly-L-□ε-ornithine), poly-L-arginine, other polymeric forms of amino acids, and salt forms thereof (e.g., calcium, potassium, sodium, or magnesium salts such as L-glutamic acid mono sodium salt). The poly-amino acid additives also may be in the D- or L-configuration. Additionally, the poly-amino acids may be α-, β-, γ-, δ-, and ε-isomers if appropriate. Combinations of the foregoing poly-amino acids and their corresponding salts (e.g., sodium, potassium, calcium, magnesium salts or other alkali or alkaline earth metal salts thereof or acid salts) also are suitable additives in some embodiments. The poly-amino acids described herein also may comprise co-polymers of different amino acids. The poly-amino acids may be natural or synthetic. The poly-amino acids also may be modified, such that at least one atom has been added, removed, substituted, or combinations thereof (e.g., N-alkyl poly-amino acid or N-acyl poly-amino acid). As used herein, poly-amino acids encompass both modified and unmodified poly-amino acids. For example, modified poly-amino acids include, but are not limited to, poly-amino acids of various molecular weights (MW), such as poly-L-α-lysine with a MW of 1,500, MW of 6,000, MW of 25,200, MW of 63,000, MW of 83,000, or MW of 300,000.

In particular embodiments, the amino acid is present in the sweetener composition in an amount effective to provide a concentration from about 10 ppm to about 50,000 ppm when present in a sweetened composition, such as, for example, a beverage. In another embodiment, the amino acid is present in the sweetener composition in an amount effective to provide a concentration from about 1,000 ppm to about 10,000 ppm when present in a sweetened composition, such as, for example, from about 2,500 ppm to about 5,000 ppm or from about 250 ppm to about 7,500 ppm.

Suitable sugar acid additives include, but are not limited to, aldonic, uronic, aldaric, alginic, gluconic, glucuronic, glucaric, galactaric, galacturonic, and salts thereof (e.g., sodium, potassium, calcium, magnesium salts or other physiologically acceptable salts), and combinations thereof.

Suitable nucleotide additives include, but are not limited to, inosine monophosphate ("IMP"), guanosine monophosphate ("GMP"), adenosine monophosphate ("AMP"), cytosine monophosphate (CMP), uracil monophosphate (UMP), inosine diphosphate, guanosine diphosphate, adenosine diphosphate, cytosine diphosphate, uracil diphosphate, inosine triphosphate, guanosine triphosphate, adenosine triphosphate, cytosine triphosphate, uracil triphosphate, alkali or alkaline earth metal salts thereof, and combinations thereof. The nucleotides described herein also may comprise nucleotide-related additives, such as nucleosides or nucleic acid bases (e.g., guanine, cytosine, adenine, thymine, uracil).

The nucleotide is present in the sweetener composition in an amount effective to provide a concentration from about 5 ppm to about 1,000 ppm when present in sweetened composition, such as, for example, a beverage.

Suitable organic acid additives include any compound which comprises a —COOH moiety, such as, for example, C2-C30 carboxylic acids, substituted hydroxyl C2-C30 carboxylic acids, butyric acid (ethyl esters), substituted butyric acid (ethyl esters), benzoic acid, substituted benzoic acids (e.g., 2,4-dihydroxybenzoic acid), substituted cinnamic acids, hydroxyacids, substituted hydroxybenzoic acids, anisic acid substituted cyclohexyl carboxylic acids, tannic acid, aconitic acid, lactic acid, tartaric acid, citric acid, isocitric acid, gluconic acid, glucoheptonic acids, adipic acid, hydroxycitric acid, malic acid, fruitaric acid (a blend of malic, fumaric, and tartaric acids), fumaric acid, maleic acid, succinic acid, chlorogenic acid, salicylic acid, creatine, caffeic acid, bile acids, acetic acid, ascorbic acid, alginic acid, erythorbic acid, polyglutamic acid, glucono delta lactone, and their alkali or alkaline earth metal salt derivatives thereof. In addition, the organic acid additives also may be in either the D- or L-configuration.

Suitable organic acid additive salts include, but are not limited to, sodium, calcium, potassium, and magnesium salts of all organic acids, such as salts of citric acid, malic acid, tartaric acid, fumaric acid, lactic acid (e.g., sodium lactate), alginic acid (e.g., sodium alginate), ascorbic acid (e.g., sodium ascorbate), benzoic acid (e.g., sodium benzoate or potassium benzoate), sorbic acid and adipic acid. The examples of the organic acid additives described optionally may be substituted with at least one group chosen from hydrogen, alkyl, alkenyl, alkynyl, halo, haloalkyl, carboxyl, acyl, acyloxy, amino, amido, carboxyl derivatives, alkylamino, dialkylamino, acylamino, alkoxy, aryloxy, nitro, cyano, sulfo, thiol, imine, sulfonyl, sulfenyl, sulfinyl, sulfamyl, carboxalkoxy, carboxamido, phosphonyl, phosphinyl, phosphoryl, phosphino, thioester, thioether, anhydride, oximino, hydrazino, carbamyl, phosphor or phosphonato. In particular embodiments, the organic acid additive is present in the sweetener composition in an amount from about 10 ppm to about 5,000 ppm.

Suitable inorganic acid additives include, but are not limited to, phosphoric acid, phosphorous acid, polyphosphoric acid, hydrochloric acid, sulfuric acid, carbonic acid, sodium dihydrogen phosphate, and alkali or alkaline earth metal salts thereof (e.g., inositol hexaphosphate Mg/Ca).

The inorganic acid additive is present in the sweetener composition in an amount effective to provide a concentration from about 25 ppm to about 25,000 ppm when present in a sweetened composition, such as, for example, a beverage.

Suitable bitter compound additives include, but are not limited to, caffeine, quinine, urea, bitter orange oil, naringin, quassia, and salts thereof.

The bitter compound is present in the sweetener composition in an amount effective to provide a concentration from about 25 ppm to about 25,000 ppm when present in a sweetened composition, such as, for example, a beverage.

Suitable flavorant and flavoring ingredient additives for include, but are not limited to, vanillin, vanilla extract, mango extract, cinnamon, citrus, coconut, ginger, viridiflorol, almond, menthol (including menthol without mint), grape skin extract, and grape seed extract. "Flavorant" and "flavoring ingredient" are synonymous and can include natural or synthetic substances or combinations thereof. Flavorants also include any other substance which imparts flavor and may include natural or non-natural (synthetic) substances which are safe for human or animals when used in a generally accepted range. Non-limiting examples of proprietary flavorants include Dohler™ Natural Flavoring Sweetness Enhancer K14323 (Dohler™ Darmstadt, Germany), Symrise™ Natural Flavor Mask for Sweeteners 161453 and 164126 (Symrise™, Holzminden, Germany), Natural Advantage™ Bitterness Blockers 1, 2, 9 and 10 (Natural Advantage™, Freehold, N.J., U.S.A.), and Sucramask™ (Creative Research Management, Stockton, Calif., U.S.A.).

The flavorant is present in the sweetener composition in an amount effective to provide a concentration from about 0.1 ppm to about 3,000 ppm when present in a sweetened composition, such as, for example, a beverage.

Suitable polymer additives include, but are not limited to, chitosan, pectin, pectic, pectinic, polyuronic, polygalacturonic acid, starch, food hydrocolloid or crude extracts thereof (e.g., gum acacia senegal (Fibergum™), gum acacia seyal, carageenan), poly-L-lysine (e.g., poly-L-α-lysine or poly-L-ε-lysine), poly-L-ornithine (e.g., poly-L-α-ornithine or poly-L-ε-ornithine), polypropylene glycol, polyethylene glycol, poly(ethylene glycol methyl ether), polyarginine, polyaspartic acid, polyglutamic acid, polyethylene imine, alginic acid, sodium alginate, propylene glycol alginate, and sodium polyethyleneglycolalginate, sodium hexametaphosphate and its salts, and other cationic polymers and anionic polymers.

The polymer is present in the sweetener composition in an amount effective to provide a concentration from about 30 ppm to about 2,000 ppm when present in a sweetened composition, such as, for example, a beverage.

Suitable protein or protein hydrolysate additives include, but are not limited to, bovine serum albumin (BSA), whey protein (including fractions or concentrates thereof such as 90% instant whey protein isolate, 34% whey protein, 50% hydrolyzed whey protein, and 80% whey protein concentrate), soluble rice protein, soy protein, protein isolates, protein hydrolysates, reaction products of protein hydrolysates, glycoproteins, and/or proteoglycans containing amino acids (e.g., glycine, alanine, serine, threonine, asparagine, glutamine, arginine, valine, isoleucine, leucine, norvaline, methionine, proline, tyrosine, hydroxyproline, and the like), collagen (e.g., gelatin), partially hydrolyzed collagen (e.g., hydrolyzed fish collagen), and collagen hydrolysates (e.g., porcine collagen hydrolysate).

The protein hydrosylate is present in the sweetener composition in an amount effective to provide a concentration from about 200 ppm to about 50,000 ppm when present in a sweetened composition, such as, for example, a beverage.

Suitable surfactant additives include, but are not limited to, polysorbates (e.g., polyoxyethylene sorbitan monooleate (polysorbate 80), polysorbate 20, polysorbate 60), sodium dodecylbenzenesulfonate, dioctyl sulfosuccinate or dioctyl sulfosuccinate sodium, sodium dodecyl sulfate, cetylpyridinium chloride (hexadecylpyridinium chloride), hexadecyltrimethylammonium bromide, sodium cholate, carbamoyl, choline chloride, sodium glycocholate, sodium taurodeoxycholate, lauric arginate, sodium stearoyl lactylate, sodium taurocholate, lecithins, sucrose oleate esters, sucrose stearate esters, sucrose palmitate esters, sucrose laurate esters, and other emulsifiers, and the like.

The surfactant additive is present in the sweetener composition in an amount effective to provide a concentration from about 30 ppm to about 2,000 ppm when present in a sweetened composition, such as, for example, a beverage.

Suitable flavonoid additives are classified as flavonols, flavones, flavanones, flavan-3-ols, isoflavones, or anthocyanidins. Non-limiting examples of flavonoid additives include, but are not limited to, catechins (e.g., green tea extracts such as Polyphenon™ 60, Polyphenon™ 30, and Polyphenon™ 25 (Mitsui Norin Co., Ltd., Japan), polyphenols, rutins (e.g., enzyme modified rutin Sanmelin™ AO (San-fi Gen F.F.I., Inc., Osaka, Japan)), neohesperidin, naringin, neohesperidin dihydrochalcone, and the like.

The flavonoid additive is present in the sweetener composition in an amount effective to provide a concentration from about 0.1 ppm to about 1,000 ppm when present in sweetened composition, such as, for example, a beverage.

Suitable alcohol additives include, but are not limited to, ethanol. In particular embodiments, the alcohol additive is present in the sweetener composition in an amount effective to provide a concentration from about 625 ppm to about 10,000 ppm when present in a sweetened composition, such as, for example, a beverage.

Suitable astringent compound additives include, but are not limited to, tannic acid, europium chloride ($EuCl_3$), gadolinium chloride ($GdCl_3$), terbium chloride ($TbCl_3$), alum, tannic acid, and polyphenols (e.g., tea polyphenols). The astringent additive is present in the sweetener composition in an amount effective to provide a concentration from about 10 ppm to about 5,000 ppm when present in a sweetened composition, such as, for example, a beverage.

In particular embodiments, a sweetener composition comprises amorphous Rebaudioside X; a polyol selected from erythritol, maltitol, mannitol, xylitol, sorbitol, and combinations thereof; and optionally at least one additional sweetener and/or functional ingredient. In a particular embodiment, the polyol is erythritol. The amorphous Rebaudioside X can be provided as a pure compound or as part of a *Stevia* extract or steviol glycoside mixture, as described above. Amorphous Rebaudioside X can be present in an amount from about 5% to about 99% by weight on a dry basis in either a steviol glycoside mixture or a *Stevia* extract. In one embodiment, amorphous Rebaudioside X and the polyol are present in a sweetener composition in a weight ratio from about 1:1 to about 1:800, such as, for example, from about 1:4 to about 1:800, from about 1:20 to about 1:600, from about 1:50 to about 1:300 or from about 1:75 to about 1:150. In another embodiment, amorphous Rebaudioside X is present in the sweetener composition in an amount effective to provide a concentration from about 1 ppm to about 10,000 ppm when present in a sweetened composition, such as, for example, about 500 ppm. The polyol, such as, for example, erythritol, can be present in the sweetener composition in an amount effective to provide a concentration from about 100 ppm to about 250,000 ppm when present in a sweetened composition, such as, for example, from about 5,000 ppm to about 40,000 ppm, from about 1,000 ppm to about 35,000 ppm.

In particular embodiments, a sweetener composition comprises amorphous Rebaudioside X; a carbohydrate sweetener selected from sucrose, fructose, glucose, maltose and combinations thereof; and optionally at least one additional sweetener and/or functional ingredient. The amorphous Rebaudioside X can be provided as a pure compound or as part of a *Stevia* extract or steviol glycoside mixture, as described above. Amorphous Rebaudioside X can be present in an amount from about 5% to about 99% by weight on a dry basis in either a steviol glycoside mixture or a *Stevia* extract. In one embodiment, amorphous Rebaudioside X and the carbohydrate are present in a sweetener composition in a weight ratio from about 0.001:14 to about 1:0.01, such as, for example, about 0.06:6. In one embodiment, amorphous Rebaudioside X is present in the sweetener composition in an amount effective to provide a concentration from about 1 ppm to about 10,000 ppm when present in a sweetened composition, such as, for example, about 500 ppm. The carbohydrate, such as, for example, sucrose, can be present in the sweetener composition in an amount effective to provide a concentration from about 100 ppm to about 140,000 ppm when present in a sweetened composition, such as, for example, from about 1,000 ppm to about 100,000 ppm, from about 5,000 ppm to about 80,000 ppm.

In particular embodiments, a sweetener composition comprises amorphous Rebaudioside X; an amino acid selected from glycine, alanine, proline and combinations thereof; and optionally at least one additional sweetener and/or functional ingredient. The amorphous Rebaudioside X can be provided as a pure compound or as part of a *Stevia* extract or steviol glycoside mixture, as described above. Amorphous Rebaudioside X can be present in an amount from about 5% to about 99% by weight on a dry basis in either a steviol glycoside mixture or a *Stevia* extract. In another embodiment, amorphous Rebaudioside X is present in the sweetener composition in an amount effective to provide a concentration from about 1 ppm to about 10,000 ppm when present in a sweetened composition, such as, for example, about 500 ppm. The amino acid, such as, for example, glycine, can be present in the sweetener composition in an amount effective to provide a concentration from about 10 ppm to about 50,000 ppm when present in a sweetened composition, such as, for example, from about 1,000 ppm to about 10,000 ppm, from about 2,500 ppm to about 5,000 ppm In particular embodiments, a sweetener composition comprises amorphous Rebaudioside X; a salt selected from sodium chloride, magnesium chloride, potassium chloride, calcium chloride and combinations thereof; and optionally at least one additional sweetener and/or functional ingredient. The amorphous Rebaudioside X can be provided as a pure compound or as part of a *Stevia* extract or steviol glycoside mixture, as described above. Amorphous Rebaudioside X can be present in an amount from about 5% to about 99% by weight on a dry basis in either a steviol glycoside mixture or a *Stevia* extract. In one embodiment, amorphous Rebaudioside X is present in the sweetener composition in an amount effective to provide a concentration from about 1 ppm to about 10,000 ppm, such as, for example, about 100 to about 1,000 ppm. The inorganic salt, such as, for example, magnesium chloride, is present in the sweetener composition in an amount effective to provide a concentration from about 25 ppm to about 25,000 ppm when present in a sweetened composition, such as, for example, from about 100 ppm to about 4,000 ppm or from about 100 ppm to about 3,000 ppm.

Functional Ingredients

The sweetener composition or sweetened composition can also contain one or more functional ingredients, which provide a real or perceived heath benefit to the composition. Functional ingredients include, but are not limited to, saponins, antioxidants, dietary fiber sources, fatty acids, vitamins, glucosamine, minerals, preservatives, hydration agents, probiotics, prebiotics, weight management agents, osteoporosis management agents, phytoestrogens, long chain primary aliphatic saturated alcohols, phytosterols and combinations thereof.

Saponin

In certain embodiments, the functional ingredient is at least one saponin. As used herein, the at least one saponin may comprise a single saponin or a plurality of saponins as a functional ingredient for the sweetener composition or sweetened compositions provided herein. Generally, according to particular embodiments of this invention, the at least one saponin is present in the sweetener composition or sweetened composition in an amount sufficient to promote health and wellness.

Saponins are glycosidic natural plant products comprising an aglycone ring structure and one or more sugar moieties. The combination of the nonpolar aglycone and the water soluble sugar moiety gives saponins surfactant properties, which allow them to form a foam when shaken in an aqueous solution.

The saponins are grouped together based on several common properties. In particular, saponins are surfactants which display hemolytic activity and form complexes with cholesterol. Although saponins share these properties, they are structurally diverse. The types of aglycone ring structures forming the ring structure in saponins can vary greatly. Non-limiting examples of the types of aglycone ring structures in saponin for use in particular embodiments of the invention include steroids, triterpenoids, and steroidal alkaloids. Non-limiting examples of specific aglycone ring structures for use in particular embodiments of the invention include soyasapogenol A, soyasapogenol B and soyasopogenol E. The number and type of sugar moieties attached to the aglycone ring structure can also vary greatly. Non-limiting examples of sugar moieties for use in particular embodiments of the invention include glucose, galactose, glucuronic acid, xylose, rhamnose, and methylpentose moieties. Non-limiting examples of specific saponins for use in particular embodiments of the invention include group A acetyl saponin, group B acetyl saponin, and group E acetyl saponin.

Saponins can be found in a large variety of plants and plant products, and are especially prevalent in plant skins and barks where they form a waxy protective coating. Several common sources of saponins include soybeans, which have approximately 5% saponin content by dry weight, soapwort plants (*Saponaria*), the root of which was used historically as soap, as well as alfalfa, aloe, asparagus, grapes, chickpeas, *yucca*, and various other beans and weeds. Saponins may be obtained from these sources by using extraction techniques well known to those of ordinary skill in the art. A description of conventional extraction techniques can be found in U.S. patent application Ser. No. 2005/0123662, the disclosure of which is expressly incorporated by reference.

Antioxidant

In certain embodiments, the functional ingredient is at least one antioxidant. As used herein, the at least one antioxidant may comprise a single antioxidant or a plurality of antioxidants as a functional ingredient for the sweetener composition or sweetened compositions provided herein. Generally, according to particular embodiments of this invention, the at least one antioxidant is present in the sweetener composition or sweetened composition in an amount sufficient to promote health and wellness.

As used herein "antioxidant" refers to any substance which inhibits, suppresses, or reduces oxidative damage to cells and biomolecules. Without being bound by theory, it is believed that antioxidants inhibit, suppress, or reduce oxidative damage to cells or biomolecules by stabilizing free radicals before they can cause harmful reactions. As such, antioxidants may prevent or postpone the onset of some degenerative diseases.

Examples of suitable antioxidants for embodiments of this invention include, but are not limited to, vitamins, vitamin cofactors, minerals, hormones, carotenoids, carotenoid terpenoids, non-carotenoid terpenoids, flavonoids, flavonoid polyphenolics (e.g., bioflavonoids), flavonols, flavones, phenols, polyphenols, esters of phenols, esters of polyphenols, nonflavonoid phenolics, isothiocyanates, and combinations thereof. In some embodiments, the antioxidant is vitamin A, vitamin C, vitamin E, ubiquinone, mineral selenium, manganese, melatonin, α-carotene, β-carotene, lycopene, lutein, zeanthin, crypoxanthin, reservatol, eugenol, quercetin, catechin, gossypol, hesperetin, curcumin, ferulic acid, thymol, hydroxytyrosol, tumeric, thyme, olive oil, lipoic acid, glutathinone, gutamine, oxalic acid, tocopherol-derived compounds, butylated hydroxyanisole (BHA), butylated hydroxytoluene (BHT), ethylenediaminetetraacetic acid (EDTA), tert-butylhydroquinone, acetic acid, pectin, tocotrienol, tocopherol, coenzyme Q10, zeaxanthin, astaxanthin, canthaxantin, saponins, limonoids, kaempfedrol, myricetin, isorhamnetin, proanthocyanidins, quercetin, rutin, luteolin, apigenin, tangeritin, hesperetin, naringenin, erodictyol, flavan-3-ols (e.g., anthocyanidins), gallocatechins, epicatechin and its gallate forms, epigallocatechin and its gallate forms (ECGC) theaflavin and its gallate forms, thearubigins, isoflavone phytoestrogens, genistein, daidzein, glycitein, anythocyanins, cyaniding, delphinidin, malvidin, pelargonidin, peonidin, petunidin, ellagic acid, gallic acid, salicylic acid, rosmarinic acid, cinnamic acid and its derivatives (e.g., ferulic acid), chlorogenic acid, chicoric acid, gallotannins, ellagitannins, anthoxanthins, betacyanins and other plant pigments, silymarin, citric acid, lignan, antinutrients, bilirubin, uric acid, R-α-lipoic acid, N-acetylcysteine, emblicanin, apple extract, apple skin extract (applephenon), rooibos extract red, rooibos extract, green, hawthorn berry extract, red raspberry extract, green coffee antioxidant (GCA), aronia extract 20%, grape seed extract (VinOseed), cocoa extract, hops extract, mangosteen extract, mangosteen hull extract, cranberry extract, pomegranate extract, pomegranate hull extract, pomegranate seed extract, hawthorn berry extract, pomella pomegranate extract, cinnamon bark extract, grape skin extract, bilberry extract, pine bark extract, pycnogenol, elderberry extract, mulberry root extract, wolfberry (gogi) extract, blackberry extract, blueberry extract, blueberry leaf extract, raspberry extract, turmeric extract, citrus bioflavonoids, black currant, ginger, acai powder, green coffee bean extract, green tea extract, and phytic acid, or combinations thereof. In alternate embodiments, the antioxidant is a synthetic antioxidant such as butylated hydroxytolune or butylated hydroxyanisole, for example. Other sources of suitable antioxidants for embodiments of this invention include, but are not limited to, fruits, vegetables, tea, cocoa, chocolate, spices, herbs, rice, organ meats from livestock, yeast, whole grains, or cereal grains.

Particular antioxidants belong to the class of phytonutrients called polyphenols (also known as "polyphenolics"), which are a group of chemical substances found in plants, characterized by the presence of more than one phenol group per molecule. A variety of health benefits may derived from polyphenols, including prevention of cancer, heart disease, and chronic inflammatory disease and improved mental strength and physical strength, for example. Suitable polyphenols for embodiments of this invention, include catechins, proanthocyanidins, procyanidins, anthocyanins, quercerin, rutin, reservatrol, isoflavones, curcumin, punicalagin, ellagitannin, hesperidin, naringin, citrus flavonoids, chlorogenic acid, other similar materials, and combinations thereof.

In particular embodiments, the antioxidant is a catechin such as, for example, epigallocatechin gallate (EGCG). Suitable sources of catechins for embodiments of this invention include, but are not limited to, green tea, white tea, black tea, oolong tea, chocolate, cocoa, red wine, grape seed, red grape skin, purple grape skin, red grape juice, purple grape juice, berries, pycnogenol, and red apple peel.

In some embodiments, the antioxidant is chosen from proanthocyanidins, procyanidins or combinations thereof. Suitable sources of proanthocyanidins and procyanidins for embodiments of this invention include, but are not limited to, red grapes, purple grapes, cocoa, chocolate, grape seeds, red wine, cacao beans, cranberry, apple peel, plum, blueberry, black currants, choke berry, green tea, sorghum, cinnamon, barley, red kidney bean, pinto bean, hops, almonds, hazelnuts, pecans, pistachio, pycnogenol, and colorful berries.

In particular embodiments, the antioxidant is a anthocyanin. Suitable sources of anthocyanins for embodiments of this invention include, but are not limited to, red berries, blueberries, bilberry, cranberry, raspberry, cherry, pomegranate, strawberry, elderberry, choke berry, red grape skin, purple grape skin, grape seed, red wine, black currant, red currant, cocoa, plum, apple peel, peach, red pear, red cabbage, red onion, red orange, and blackberries.

In some embodiments, the antioxidant is chosen from quercetin, rutin or combinations thereof. Suitable sources of quercetin and rutin for embodiments of this invention include, but are not limited to, red apples, onions, kale, bog whortleberry, lingonberrys, chokeberry, cranberry, blackberry, blueberry, strawberry, raspberry, black currant, green tea, black tea, plum, apricot, parsley, leek, broccoli, chili pepper, berry wine, and ginkgo.

In some embodiments, the antioxidant is resveratrol. Suitable sources of resveratrol for embodiments of this invention include, but are not limited to, red grapes, peanuts, cranberry, blueberry, bilberry, mulberry, Japanese Itadori tea, and red wine.

In particular embodiments, the antioxidant is an isoflavone. Suitable sources of isoflavones for embodiments of this invention include, but are not limited to, soy beans, soy products, legumes, alfalfa spouts, chickpeas, peanuts, and red clover.

In some embodiments, the antioxidant is curcumin. Suitable sources of curcumin for embodiments of this invention include, but are not limited to, turmeric and mustard.

In particular embodiments, the antioxidant is chosen from punicalagin, ellagitannin or combinations thereof. Suitable sources of punicalagin and ellagitannin for embodiments of this invention include, but are not limited to, pomegranate, raspberry, strawberry, walnut, and oak-aged red wine.

In some embodiments, the antioxidant is a citrus flavonoid, such as hesperidin or naringin. Suitable sources of citrus flavonids, such as hesperidin or naringin, for embodiments of this invention include, but are not limited to, oranges, grapefruits, and citrus juices.

In particular embodiments, the antioxidant is chlorogenic acid. Suitable sources of chlorogenic acid for embodiments of this invention include, but are not limited to, green coffee, yerba mate, red wine, grape seed, red grape skin, purple grape skin, red grape juice, purple grape juice, apple juice, cranberry, pomegranate, blueberry, strawberry, sunflower, *Echinacea*, pycnogenol, and apple peel.

Dietary Fiber

In certain embodiments, the functional ingredient is at least one dietary fiber source. As used herein, the at least one dietary fiber source may comprise a single dietary fiber source or a plurality of dietary fiber sources as a functional ingredient for the sweetener compositions or sweetened compositions provided herein. Generally, according to particular embodiments of this invention, the at least one dietary fiber source is present in the sweetener composition or sweetened composition in an amount sufficient to promote health and wellness.

Numerous polymeric carbohydrates having significantly different structures in both composition and linkages fall within the definition of dietary fiber. Such compounds are well known to those skilled in the art, non-limiting examples of which include non-starch polysaccharides, lignin, cellulose, methylcellulose, the hemicelluloses, β-glucans, pectins, gums, mucilage, waxes, inulins, oligosaccharides, fructooligosaccharides, cyclodextrins, chitins, and combinations thereof.

Polysaccharides are complex carbohydrates composed of monosaccharides joined by glycosidic linkages. Non-starch polysaccharides are bonded with β-linkages, which humans are unable to digest due to a lack of an enzyme to break the β-linkages. Conversely, digestible starch polysaccharides generally comprise α(1-4) linkages.

Lignin is a large, highly branched and cross-linked polymer based on oxygenated phenylpropane units. Cellulose is a linear polymer of glucose molecules joined by a β(1-4) linkage, which mammalian amylases are unable to hydrolyze. Methylcellulose is a methyl ester of cellulose that is often used in foodstuffs as a thickener, and emulsifier. It is commercially available (e.g., Citrucel by GlaxoSmithKline, Celevac by Shire Pharmaceuticals). Hemicelluloses are highly branched polymers consisting mainly of glucurono- and 4-O-methylglucuroxylans. β-Glucans are mixed-linkage (1-3), (1-4) β-D-glucose polymers found primarily in cereals, such as oats and barley. Pectins, such as beta pectin, are a group of polysaccharides composed primarily of D-galacturonic acid, which is methoxylated to variable degrees.

Gums and mucilages represent a broad array of different branched structures. Guar gum, derived from the ground endosperm of the guar seed, is a galactomannan. Guar gum is commercially available (e.g., Benefiber by Novartis AG). Other gums, such as gum arabic andpectins, have still different structures. Still other gums include xanthan gum, gellan gum, tara gum, psylium seed husk gum, and locust been gum.

Waxes are esters of ethylene glycol and two fatty acids, generally occurring as a hydrophobic liquid that is insoluble in water.

Inulins comprise naturally occurring oligosaccharides belonging to a class of carbohydrates known as fructans. They generally are comprised of fructose units joined by β(2-1) glycosidic linkages with a terminal glucose unit. Oligosaccharides are saccharide polymers containing typically three to six component sugars. They are generally found either O- or N-linked to compatible amino acid side chains in proteins or to lipid molecules. Fructooligosaccharides are oligosaccharides consisting of short chains of fructose molecules.

Cyclodextrins are a family of cyclic oligosaccharides composed of α-D-glucopyranoside units. They can be produced from starch by means of enzymatic conversion. α-Cyclodextrin is a six sugar ring molecule, whereas β- and γ-cyclodextrins have seven and eight sugar ring molecules, respectively. Non-cyclic dextrins are known as maltodextrins and are generally easily digested by humans. Digestion resistant maltodextrin is commercially available (e.g., Fibersol-2 by ADM).

Food sources of dietary fiber include, but are not limited to, grains, legumes, fruits, and vegetables. Grains providing dietary fiber include, but are not limited to, oats, rye, barley, wheat. Legumes providing fiber include, but are not limited to, peas and beans such as soybeans. Fruits and vegetables providing a source of fiber include, but are not limited to, apples, oranges, pears, bananas, berries, tomatoes, green beans, broccoli, cauliflower, carrots, potatoes, celery. Plant foods such as bran, nuts, and seeds (such as flax seeds) are also sources of dietary fiber. Parts of plants providing dietary fiber include, but are not limited to, the stems, roots, leaves, seeds, pulp, and skin.

Although dietary fiber generally is derived from plant sources, indigestible animal products such as chitins are also classified as dietary fiber. Chitin is a polysaccharide composed of units of acetylglucosamine joined by β(1-4) linkages, similar to the linkages of cellulose.

Sources of dietary fiber often are divided into categories of soluble and insoluble fiber based on their solubility in water. Both soluble and insoluble fibers are found in plant foods to varying degrees depending upon the characteristics of the plant. Although insoluble in water, insoluble fiber has passive hydrophilic properties that help increase bulk, soften stools, and shorten transit time of fecal solids through the intestinal tract.

Unlike insoluble fiber, soluble fiber readily dissolves in water. Soluble fiber undergoes active metabolic processing via fermentation in the colon, increasing the colonic microflora and thereby increasing the mass of fecal solids. Fermentation of fibers by colonic bacteria also yields end-products with significant health benefits. For example, fermentation of the food masses produces gases and short-chain fatty acids. Acids produced during fermentation include butyric, acetic, propionic, and valeric acids that have various beneficial properties such as stabilizing blood glucose levels by acting on pancreatic insulin release and providing liver control by glycogen breakdown. In addition, fiber fermentation may reduce atherosclerosis by lowering cholesterol synthesis by the liver and reducing blood levels of LDL and triglycerides. The acids produced during fermentation lower colonic pH, thereby protecting the colon lining from cancer polyp formation. The lower colonic pH also increases mineral absorption, improves the barrier properties of the colonic mucosal layer, and inhibits inflammatory and adhesion irritants. Fermentation of fibers also may benefit the immune system by stimulating production of T-helper cells, antibodies, leukocytes, splenocytes, cytokinins and lymphocytes.

Fatty Acid

In certain embodiments, the functional ingredient is at least one fatty acid. As used herein, the at least one fatty acid may be single fatty acid or a plurality of fatty acids as a functional ingredient for the sweetener composition or sweetened compositions provided herein. Generally, according to particular embodiments of this invention, the at least one fatty acid is present in the sweetener composition or sweetened composition in an amount sufficient to promote health and wellness.

As used herein, "fatty acid" refers to any straight chain monocarboxylic acid and includes saturated fatty acids, unsaturated fatty acids, long chain fatty acids, medium chain fatty acids, short chain fatty acids, fatty acid precursors (including omega-9 fatty acid precursors), and esterified fatty acids. As used herein, "long chain polyunsaturated fatty acid" refers to any polyunsaturated carboxylic acid or organic acid with a long aliphatic tail. As used herein, "omega-3 fatty acid" refers to any polyunsaturated fatty acid having a first double bond as the third carbon-carbon bond from the terminal methyl end of its carbon chain. In particular embodiments, the omega-3 fatty acid may comprise a long chain omega-3 fatty acid. As used herein, "omega-6 fatty acid" any polyunsaturated fatty acid having a first double bond as the sixth carbon-carbon bond from the terminal methyl end of its carbon chain.

Suitable omega-3 fatty acids for use in embodiments of the present invention can be derived from algae, fish, animals, plants, or combinations thereof, for example. Examples of suitable omega-3 fatty acids include, but are not limited to, linolenic acid, alpha-linolenic acid, eicosapentaenoic acid, docosahexaenoic acid, stearidonic acid, eicosatetraenoic acid and combinations thereof. In some embodiments, suitable omega-3 fatty acids can be provided in fish oils, (e.g., menhaden oil, tuna oil, salmon oil, bonito oil, and cod oil), microalgae omega-3 oils or combinations thereof. In particular embodiments, suitable omega-3 fatty acids may be derived from commercially available omega-3 fatty acid oils such as Microalgae DHA oil (from Martek, Columbia, Md.), OmegaPure (from Omega Protein, Houston, Tex.), Marinol C-38 (from Lipid Nutrition, Channahon, Ill.), Bonito oil and MEG-3 (from Ocean Nutrition, Dartmouth, NS), Evogel (from Symrise, Holzminden, Germany), Marine Oil, from tuna or salmon (from Arista Wilton, Conn.), OmegaSource 2000, Marine Oil, from menhaden and Marine Oil, from cod (from OmegaSource, RTP, NC).

Suitable omega-6 fatty acids include, but are not limited to, linoleic acid, gamma-linolenic acid, dihommo-gamma-linolenic acid, arachidonic acid, eicosadienoic acid, docosadienoic acid, adrenic acid, docosapentaenoic acid and combinations thereof.

Suitable esterified fatty acids for embodiments of the present invention may include, but are not limited to, monoacylglycerols containing omega-3 and/or omega-6 fatty acids, diacylglycerols containing omega-3 and/or omega-6 fatty acids, or triacylglycerols containing omega-3 and/or omega-6 fatty acids and combinations thereof.

Vitamin

In certain embodiments, the functional ingredient is at least one vitamin. As used herein, the at least one vitamin may be single vitamin or a plurality of vitamins as a functional ingredient for the sweetener and sweetened compositions provided herein. Generally, according to particular embodiments of this invention, the at least one vitamin is present in the sweetener composition or sweetened composition in an amount sufficient to promote health and wellness.

Vitamins are organic compounds that the human body needs in small quantities for normal functioning. The body uses vitamins without breaking them down, unlike other nutrients such as carbohydrates and proteins. To date, thirteen vitamins have been recognized, and one or more can be used in the functional sweetener and sweetened compositions herein. Suitable vitamins include, vitamin A, vitamin D, vitamin E, vitamin K, vitamin B1, vitamin B2, vitamin B3, vitamin B5, vitamin B6, vitamin B7, vitamin B9, vitamin B12, and vitamin C. Many of vitamins also have alternative chemical names, non-limiting examples of which are provided below.

| Vitamin | Alternative names |
| --- | --- |
| Vitamin A | Retinol |
| | Retinaldehyde |
| | Retinoic acid |
| | Retinoids |
| | Retinal |
| | Retinoic ester |
| Vitamin D | Calciferol |
| (vitamins D1-D5) | Cholecalciferol |
| | Lumisterol |
| | Ergocalciferol |
| | Dihydrotachysterol |
| | 7-dehydrocholesterol |
| Vitamin E | Tocopherol |
| | Tocotrienol |
| Vitamin K | Phylloquinone |
| | Naphthoquinone |
| Vitamin B1 | Thiamin |
| Vitamin B2 | Riboflavin |
| | Vitamin G |
| Vitamin | Alternative names |
| Vitamin B3 | Niacin |
| | Nicotinic acid |
| | Vitamin PP |
| Vitamin B5 | Pantothenic acid |
| Vitamin B6 | Pyridoxine |
| | Pyridoxal |
| | Pyridoxamine |
| Vitamin B7 | Biotin |
| | Vitamin H |
| Vitamin B9 | Folic acid |
| | Folate |
| | Folacin |
| | Vitamin M |
| | Pteroyl-L-glutamic acid |
| Vitamin B12 | Cobalamin |
| | Cyanocobalamin |
| Vitamin C | Ascorbic Acid |

Various other compounds have been classified as vitamins by some authorities. These compounds may be termed pseudo-vitamins and include, but are not limited to, compounds such as ubiquinone (coenzyme Q10), pangamic acid, dimethylglycine, taestrile, amygdaline, flavanoids, para-aminobenzoic acid, adenine, adenylic acid, and s-methylmethionine. As used herein, the term vitamin includes pseudo-vitamins.

In some embodiments, the vitamin is a fat-soluble vitamin chosen from vitamin A, D, E, K and combinations thereof.

In other embodiments, the vitamin is a water-soluble vitamin chosen from vitamin B1, vitamin B2, vitamin B3, vitamin B6, vitamin B12, folic acid, biotin, pantothenic acid, vitamin C and combinations thereof.

Glucosamine

In certain embodiments, the functional ingredient is glucosamine. Generally, according to particular embodiments of this invention, glucosamine is present in the functional sweetener composition or sweetened composition in an amount sufficient to promote health and wellness.

Glucosamine, also called chitosamine, is an amino sugar that is believed to be an important precurosor in the biochemical synthesis of glycosylated proteins and lipids. D-glucosamine occurs naturally in the cartilage in the form of glucosamine-6-phosphate, which is synthesized from fructose-6-phosphate and glutamine. However, glucosamine also is available in other forms, non-limiting examples of which include glucosamine hydrochloride, glucosamine sulfate, N-acetyl-glucosamine, or any other salt forms or combinations thereof. Glucosamine may be obtained by acid hydrolysis of the shells of lobsters, crabs, shrimps, or prawns using methods well known to those of ordinary skill in the art. In a particular embodiment, glucosamine may be derived from fungal biomass containing chitin, as described in U.S. Patent Publication No. 2006/0172392.

The sweetener compositions or sweetened composition can further comprise chondroitin sulfate.

Mineral

In certain embodiments, the functional ingredient is at least one mineral. As used herein, the at least one mineral may be single mineral or a plurality of minerals as a functional ingredient for the sweetener compositions or sweetened compositions provided herein. Generally, according to particular embodiments of this invention, the at least one mineral is present in the sweetener composition or sweetened composition in an amount sufficient to promote health and wellness.

Minerals, in accordance with the teachings of this invention, comprise inorganic chemical elements required by living organisms. Minerals are comprised of a broad range of compositions (e.g., elements, simple salts, and complex silicates) and also vary broadly in crystalline structure. They may naturally occur in foods and beverages, may be added as a supplement, or may be consumed or administered separately from foods or beverages.

Minerals may be categorized as either bulk minerals, which are required in relatively large amounts, or trace minerals, which are required in relatively small amounts. Bulk minerals generally are required in amounts greater than or equal to about 100 mg per day and trace minerals are those that are required in amounts less than about 100 mg per day.

In particular embodiments of this invention, the mineral is chosen from bulk minerals, trace minerals or combinations thereof. Non-limiting examples of bulk minerals include calcium, chlorine, magnesium, phosphorous, potassium, sodium, and sulfur. Non-limiting examples of trace minerals include chromium, cobalt, copper, fluorine, iron, manganese, molybdenum, selenium, zinc, and iodine. Although iodine generally is classified as a trace mineral, it is required in larger quantities than other trace minerals and often is categorized as a bulk mineral.

In other particular embodiments of this invention, the mineral is a trace mineral, believed to be necessary for human nutrition, non-limiting examples of which include bismuth, boron, lithium, nickel, rubidium, silicon, strontium, tellurium, tin, titanium, tungsten, and vanadium.

The minerals embodied herein may be in any form known to those of ordinary skill in the art. For example, in a particular embodiment the minerals may be in their ionic form, having either a positive or negative charge. In another particular embodiment the minerals may be in their molecular form. For example, sulfur and phosphorous often are found naturally as sulfates, sulfides, and phosphates.

Preservative

In certain embodiments, the functional ingredient is at least one preservative. As used herein, the at least one preservative may be single preservative or a plurality of preservatives as a functional ingredient for the sweetener compositions or sweetened composition provided herein. Generally, according to particular embodiments of this invention, the at least one preservative is present in the sweetener composition or sweetened composition in an amount sufficient to promote health and wellness.

In particular embodiments of this invention, the preservative is chosen from antimicrobials, antioxidants, antienzymatics or combinations thereof. Non-limiting examples of antimicrobials include sulfites, propionates, benzoates, sorbates, nitrates, nitrites, bacteriocins, salts, sugars, acetic acid, dimethyl dicarbonate (DMDC), ethanol, and ozone.

According to a particular embodiment, the preservative is a sulfite. Sulfites include, but are not limited to, sulfur dioxide, sodium bisulfite, and potassium hydrogen sulfite.

According to another particular embodiment, the preservative is a propionate. Propionates include, but are not limited to, propionic acid, calcium propionate, and sodium propionate.

According to yet another particular embodiment, the preservative is a benzoate. Benzoates include, but are not limited to, sodium benzoate and benzoic acid.

In another particular embodiment, the preservative is a sorbate. Sorbates include, but are not limited to, potassium sorbate, sodium sorbate, calcium sorbate, and sorbic acid.

In still another particular embodiment, the preservative is a nitrate and/or a nitrite. Nitrates and nitrites include, but are not limited to, sodium nitrate and sodium nitrite.

In yet another particular embodiment, the at least one preservative is a bacteriocin, such as, for example, nisin.

In another particular embodiment, the preservative is ethanol.

In still another particular embodiment, the preservative is ozone.

Non-limiting examples of antienzymatics suitable for use as preservatives in particular embodiments of the invention include ascorbic acid, citric acid, and metal chelating agents such as ethylenediaminetetraacetic acid (EDTA).

Hydration Agent

In certain embodiments, the functional ingredient is at least one hydration agent. As used herein, the at least one hydration agent may be single hydration agent or a plurality of hydration agents as a functional ingredient for the sweetener compositions or sweetened composition provided herein. Generally, according to particular embodiments of this invention, the at least one hydration agent is present in the sweetener composition or sweetened composition in an amount sufficient to promote health and wellness.

Hydration products help the body to replace fluids that are lost through excretion. For example, fluid is lost as sweat in order to regulate body temperature, as urine in order to excrete waste substances, and as water vapor in order to exchange gases in the lungs. Fluid loss can also occur due to a wide range of external causes, non-limiting examples of which include physical activity, exposure to dry air, diarrhea, vomiting, hyperthermia, shock, blood loss, and hypotension. Diseases causing fluid loss include diabetes, cholera, gastroenteritis, shigellosis, and yellow fever. Forms of malnutrition that cause fluid loss include the excessive consumption of alcohol, electrolyte imbalance, fasting, and rapid weight loss.

In a particular embodiment, the hydration product is a composition that helps the body replace fluids that are lost during exercise. Accordingly, in a particular embodiment, the hydration product is an electrolyte, non-limiting examples of which include sodium, potassium, calcium, magnesium, chloride, phosphate, bicarbonate, and combinations thereof. Suitable electrolytes for use in particular embodiments of this invention are also described in U.S. Pat. No. 5,681,569, the disclosure of which is expressly incorporated herein by reference. In particular embodiments, the electrolytes are obtained from their corresponding water-soluble salts. Non-limiting examples of salts for use in particular embodiments include chlorides, carbonates, sulfates, acetates, bicarbonates, citrates, phosphates, hydrogen phosphates, tartrates, sorbates, citrates, benzoates, or combinations thereof. In other embodiments, the electrolytes are provided by juice, fruit extracts, vegetable extracts, tea, or teas extracts.

In particular embodiments of this invention, the hydration product is a carbohydrate to supplement energy stores burned by muscles. Suitable carbohydrates for use in particular embodiments of this invention are described in U.S. Pat. Nos. 4,312,856, 4,853,237, 5,681,569, and 6,989,171, the disclosures of which are expressly incorporated herein by reference. Non-limiting examples of suitable carbohydrates include monosaccharides, disaccharides, oligosaccharides, complex polysaccharides or combinations thereof. Non-limiting examples of suitable types of monosaccharides for use in particular embodiments include trioses, tetroses, pentoses, hexoses, heptoses, octoses, and nonoses. Non-limiting examples of specific types of suitable monosaccharides include glyceraldehyde, dihydroxyacetone, erythrose, threose, erythrulose, arabinose, lyxose, ribose, xylose, ribulose, xylulose, allose, altrose, galactose, glucose, gulose, idose, mannose, talose, fructose, psicose, sorbose, tagatose, mannoheptulose, sedoheptulose, octolose, and sialose. Non-limiting examples of suitable disaccharides include sucrose, lactose, and maltose. Non-limiting examples of suitable oligosaccharides include saccharose, maltotriose, and maltodextrin. In other particular embodiments, the carbohydrates are provided by a corn syrup, a beet sugar, a cane sugar, a juice, or a tea.

In another particular embodiment, the hydration is a flavanol that provides cellular rehydration. Flavanols are a class of natural substances present in plants, and generally comprise a 2-phenylbenzopyrone molecular skeleton attached to one or more chemical moieties. Non-limiting examples of suitable flavanols for use in particular embodiments of this invention include catechin, epicatechin, gallocatechin, epigallocatechin, epicatechin gallate, epigallocatechin 3-gallate, theaflavin, theaflavin 3-gallate, theaflavin 3'-gallate, theaflavin 3,3' gallate, thearubigin or combinations thereof. Several common sources of flavanols include tea plants, fruits, vegetables, and flowers. In preferred embodiments, the flavanol is extracted from green tea.

In a particular embodiment, the hydration product is a glycerol solution to enhance exercise endurance. The ingestion of a glycerol containing solution has been shown to provide beneficial physiological effects, such as expanded blood volume, lower heart rate, and lower rectal temperature.

Probiotics/Probiotics

In certain embodiments, the functional ingredient is chosen from at least one probiotic, prebiotic and combination thereof. As used herein, the at least one probiotic or prebiotic may be single probiotic or prebiotic or a plurality of probiotics or prebiotics as a functional ingredient for the sweetener compositions or sweetened composition provided herein. Generally, according to particular embodiments of this invention, the at least one probiotic, prebiotic or combination thereof is present in the sweetener composition or sweetened composition in an amount sufficient to promote health and wellness.

Probiotics, in accordance with the teachings of this invention, comprise microorganisms that benefit health when consumed in an effective amount. Desirably, probiotics beneficially affect the human body's naturally-occurring gastrointestinal microflora and impart health benefits apart from nutrition. Probiotics may include, without limitation, bacteria, yeasts, and fungi.

According to particular embodiments, the probiotic is a beneficial microorganisms that beneficially affects the human body's naturally-occurring gastrointestinal microflora and imparts health benefits apart from nutrition. Examples of probiotics include, but are not limited to, bacteria of the genus *Lactobacilli*, *Bifidobacteria*, *Streptococci*, or combinations thereof, that confer beneficial effects to humans.

In particular embodiments of the invention, the at least one probiotic is chosen from the genus *Lactobacilli*. *Lactobacilli* (i.e., bacteria of the genus *Lactobacillus*, hereinafter "L.") have been used for several hundred years as a food preservative and for promoting human health. Non-limiting examples of species of *Lactobacilli* found in the human intestinal tract include *L. acidophilus*, *L. casei*, *L. fermentum*, *L. saliva roes*, *L. brevis*, *L. leichmannii*, *L. plantarum*, *L. cellobiosus*, *L. reuteri*, *L. rhamnosus*, *L. GG*, *L. bulgaricus*, and *L. thermophilus*.

According to other particular embodiments of this invention, the probiotic is chosen from the genus *Bifidobacteria*. *Bifidobacteria* also are known to exert a beneficial influence on human health by producing short chain fatty acids (e.g., acetic, propionic, and butyric acids), lactic, and formic acids as a result of carbohydrate metabolism. Non-limiting species of *Bifidobacteria* found in the human gastrointestinal tract include *B. angulatum*, *B. animalis*, *B. asteroides*, *B. bifidum*, *B. boum*, *B. breve*, *B. catenulatum*, *B. choerinum*, *B. coryneforme*, *B. cuniculi*, *B. dentium*, *B. gallicum*, *B. gallinarum*, *B indicum*, *B. longum*, *B. magnum*, *B. merycicum*, *B. minimum*, *B. pseudocatenulatum*, *B. pseudolongum*, *B. psychraerophilum*, *B. pullorum*, *B. ruminantium*, *B. saeculare*, *B. scardovii*, *B. simiae*, *B. subtile*, *B. thermacidophilum*, *B. thermophilum*, *B. urinalis*, and B. sp.

According to other particular embodiments of this invention, the probiotic is chosen from the genus *Streptococcus*. *Streptococcus thermophilus* is a gram-positive facultative anaerobe. It is classified as a lactic acid bacteria and commonly is found in milk and milk products, and is used in the production of yogurt. Other non-limiting probiotic species of this bacteria include *Streptococcus salivarus* and *Streptococcus cremoris*.

Probiotics that may be used in accordance with this invention are well-known to those of skill in the art. Non-limiting examples of foodstuffs comprising probiotics include yogurt, sauerkraut, kefir, kimchi, fermented vegetables, and other foodstuffs containing a microbial element that beneficially affects the host animal by improving the intestinal microbalance.

Prebiotics, in accordance with the teachings of this invention, are compositions that promote the growth of beneficial bacteria in the intestines. Prebiotic substances can be consumed by a relevant probiotic, or otherwise assist in keeping the relevant probiotic alive or stimulate its growth. When consumed in an effective amount, prebiotics also beneficially affect the human body's naturally-occurring gastrointestinal microflora and thereby impart health benefits apart from just nutrition. Prebiotic foods enter the colon and serve as substrate for the endogenous bacteria, thereby indirectly providing the host with energy, metabolic substrates, and essential micronutrients. The body's digestion and absorption of prebiotic foods is dependent upon bacterial metabolic activity, which salvages energy for the host from nutrients that escaped digestion and absorption in the small intestine.

Prebiotics, in accordance with the embodiments of this invention, include, without limitation, mucopolysaccharides, oligosaccharides, polysaccharides, amino acids, vitamins, nutrient precursors, proteins and combinations thereof.

According to a particular embodiment of this invention, the prebiotic is chosen from dietary fibers, including, without limitation, polysaccharides and oligosaccharides. These compounds have the ability to increase the number of probiotics, which leads to the benefits conferred by the probiotics. Non-limiting examples of oligosaccharides that are categorized as prebiotics in accordance with particular embodiments of this invention include fructooligosaccharides, inulins, isomalto-oligosaccharides, lactilol, lactosucrose, lactulose, pyrodextrins, soy oligosaccharides, transgalacto-oligosaccharides, and xylo-oligosaccharides.

According to other particular embodiments of the invention, the prebiotic is an amino acid. Although a number of known prebiotics break down to provide carbohydrates for probiotics, some probiotics also require amino acids for nourishment.

Prebiotics are found naturally in a variety of foods including, without limitation, bananas, berries, asparagus, garlic, wheat, oats, barley (and other whole grains), flaxseed, tomatoes, Jerusalem artichoke, onions and chicory, greens (e.g., dandelion greens, spinach, collard greens, chard, kale, mustard greens, turnip greens), and legumes (e.g., lentils, kidney beans, chickpeas, navy beans, white beans, black beans).

Weight Management Agent

In certain embodiments, the functional ingredient is at least one weight management agent. As used herein, the at least one weight management agent may be single weight management agent or a plurality of weight management agents as a functional ingredient for the sweetener compositions or sweetened composition provided herein. Generally, according to particular embodiments of this invention, the at least one weight management agent is present in the sweetener composition or sweetened composition in an amount sufficient to promote health and wellness.

As used herein, "a weight management agent" includes an appetite suppressant and/or a thermogenesis agent. As used herein, the phrases "appetite suppressant", "appetite satiation compositions", "satiety agents", and "satiety ingredients" are synonymous. The phrase "appetite suppressant" describes macronutrients, herbal extracts, exogenous hormones, anorectics, anorexigenics, pharmaceutical drugs, and combinations thereof, that when delivered in an effective amount, suppress, inhibit, reduce, or otherwise curtail a person's appetite. The phrase "thermogenesis agent" describes macronutrients, herbal extracts, exogenous hormones, anorectics, anorexigenics, pharmaceutical drugs, and combinations thereof, that when delivered in an effective amount, activate or otherwise enhance a person's thermogenesis or metabolism.

Suitable weight management agents include macronutrient selected from the group consisting of proteins, carbohydrates, dietary fats, and combinations thereof. Consumption of proteins, carbohydrates, and dietary fats stimulates the release of peptides with appetite-suppressing effects. For example, consumption of proteins and dietary fats stimulates the release of the gut hormone cholecytokinin (CCK), while consumption of carbohydrates and dietary fats stimulates release of Glucagon-like peptide 1 (GLP-1).

Suitable macronutrient weight management agents also include carbohydrates. Carbohydrates generally comprise sugars, starches, cellulose and gums that the body converts into glucose for energy. Carbohydrates often are classified into two categories, digestible carbohydrates (e.g., monosaccharides, disaccharides, and starch) and non-digestible carbohydrates (e.g., dietary fiber). Studies have shown that non-digestible carbohydrates and complex polymeric carbohydrates having reduced absorption and digestibility in the small intestine stimulate physiologic responses that inhibit food intake. Accordingly, the carbohydrates embodied herein desirably comprise non-digestible carbohydrates or carbohydrates with reduced digestibility. Non-limiting examples of such carbohydrates include polydextrose; inulin; monosaccharide-derived polyols such as erythritol, mannitol, xylitol, and sorbitol; disaccharide-derived alcohols such as isomalt, lactitol, and maltitol; and hydrogenated starch hydrolysates. Carbohydrates are described in more detail herein below.

In another particular embodiment weight management agents is dietary fat. Dietary fats are lipids comprising combinations of saturated and unsaturated fatty acids. Poly-unsaturated fatty acids have been shown to have a greater satiating power than mono-unsaturated fatty acids. Accordingly, the dietary fats embodied herein desirably comprise poly-unsaturated fatty acids, non-limiting examples of which include triacylglycerols.

In a particular embodiment, the weight management agents is an herbal extract. Extracts from numerous types of plants have been identified as possessing appetite suppressant properties. Non-limiting examples of plants whose extracts have appetite suppressant properties include plants of the genus *Hoodia, Trichocaulon, Caralluma, Stapelia, Orbea, Asclepias,* and *Camelia*. Other embodiments include extracts derived from Gymnema Sylvestre, Kola Nut, Citrus Auran tium, Yerba Mate, Griffonia Simplicifolia, Guarana, myrrh, guggul Lipid, and black current seed oil.

The herbal extracts may be prepared from any type of plant material or plant biomass. Non-limiting examples of plant material and biomass include the stems, roots, leaves, dried powder obtained from the plant material, and sap or dried sap. The herbal extracts generally are prepared by extracting sap from the plant and then spray-drying the sap. Alternatively, solvent extraction procedures may be employed. Following the initial extraction, it may be desirable to further fractionate the initial extract (e.g., by column chromatography) in order to obtain an herbal extract with enhanced activity. Such techniques are well known to those of ordinary skill in the art.

In a particular embodiment, the herbal extract is derived from a plant of the genus Hoodia, species of which include *H. alstonii, H. currorii, H. dregei, H. flava, H. gordonii, H. jutatae, H. mossamedensis, H. officinalis, H. parviflorai, H. pedicellata, H. pilifera, H. ruschii,* and *H. triebneri*. Hoodia plants are stem succulents native to southern Africa. A sterol glycoside of Hoodia, known as P57, is believed to be responsible for the appetite-suppressant effect of the Hoodia species.

In another particular embodiment, the herbal extract is derived from a plant of the genus Caralluma, species of which include *C. indica, C. fimbriata, C. attenuate, C. tuberculata, C. edulis, C. adscendens, C. stalagmifera, C. umbellate, C. penicillata, C. russeliana, C. retrospicens, C. Arabica,* and *C. lasiantha*. *Carralluma* plants belong to the same Subfamily as Hoodia, Asclepiadaceae. Caralluma are small, erect and fleshy plants native to India having medicinal properties, such as appetite suppression, that generally are attributed to glycosides belonging to the pregnane group of glycosides, non-limiting examples of which include caratuberside A, caratuberside B, bouceroside I, bouceroside II, bouceroside III, bouceroside IV, bouceroside V, bouceroside VI, bouceroside VII, bouceroside VIII, bouceroside IX, and bouceroside X.

In another particular embodiment, the at least one herbal extract is derived from a plant of the genus Trichocaulon. Trichocaulon plants are succulents that generally are native to southern Africa, similar to Hoodia, and include the species *T. piliferum* and *T. officinale*.

In another particular embodiment, the herbal extract is derived from a plant of the genus *Stapelia* or *Orbea*, species of which include *S. gigantean* and *O. variegate*, respectively. Both *Stapelia* and *Orbea* plants belong to the same Subfamily as Hoodia, Asclepiadaceae. Not wishing to be bound by any theory, it is believed that they compounds exhibiting appetite suppressant activity are saponins, such as pregnane glycosides, which include stavarosides A, B, C, D, E, F, G, H, I, J, and K.

In another particular embodiment, the herbal extract is derived from a plant of the genus *Asclepias*. *Asclepias* plants also belong to the Asclepiadaceae family of plants. Non-limiting examples of *Asclepias* plants include *A. incarnate, A. curassayica, A. syriaca*, and *A. tuberose*. Not wishing to be bound by any theory, it is believed that the extracts comprise steroidal compounds, such as pregnane glycosides and pregnane aglycones, having appetite suppressant effects.

In a particular embodiment, the weight management agent is an exogenous hormone having a weight management effect. Non-limiting examples of such hormones include CCK, peptide YY, ghrelin, bombesin and gastrin-releasing peptide (GRP), enterostatin, apolipoprotein A-IV, GLP-1, amylin, somastatin, and leptin.

In another embodiment, the weight management agent is a pharmaceutical drug. Non-limiting examples include phentenime, diethylpropion, phendimetrazine, sibutramine, rimonabant, oxyntomodulin, floxetine hydrochloride, ephedrine, phenethylamine, or other stimulants.

The at least one weight management agent may be utilized individually or in combination as a functional ingredient for the sweetener compositions provided in this invention.

Osteoporosis Management Agent

In certain embodiments, the functional ingredient is at least one osteoporosis management agent. As used herein, the at least one osteoporosis management agent may be single osteoporosis management agent or a plurality of osteoporosis management agent as a functional ingredient for the sweetener compositions or sweetened composition provided herein. Generally, according to particular embodiments of this invention, the at least one osteoporosis management agent is present in the sweetener composition or sweetened composition in an amount sufficient to promote health and wellness.

Osteoporosis is a skeletal disorder of compromised bone strength, resulting in an increased risk of bone fracture. Generally, osteoporosis is characterized by reduction of the bone mineral density (BMD), disruption of bone micro-architecture, and changes to the amount and variety of non-collagenous proteins in the bone.

In certain embodiments, the osteoporosis management agent is at least one calcium source. According to a particular embodiment, the calcium source is any compound containing calcium, including salt complexes, solubilized species, and other forms of calcium. Non-limiting examples of calcium sources include amino acid chelated calcium, calcium carbonate, calcium oxide, calcium hydroxide, calcium sulfate, calcium chloride, calcium phosphate, calcium hydrogen phosphate, calcium dihydrogen phosphate, calcium citrate, calcium malate, calcium citrate malate, calcium gluconate, calcium tartrate, calcium lactate, solubilized species thereof, and combinations thereof.

According to a particular embodiment, the osteoporosis management agent is a magnesium source. The magnesium source is any compound containing magnesium, including salt complexes, solubilized species, and other forms of magnesium. Non-limiting examples of magnesium sources include magnesium chloride, magnesium citrate, magnesium gluceptate, magnesium gluconate, magnesium hydroxide, magnesium picolate, magnesium sulfate, solubilized species thereof, and mixtures thereof. In another particular embodiment, the magnesium source comprises an amino acid chelated or creatine chelated magnesium.

In other embodiments, the osteoporosis agent is chosen from vitamins D, C, K, their precursors and/or beta-carotene and combinations thereof.

Numerous plants and plant extracts also have been identified as being effective in the prevention and treatment of osteoporosis. Not wishing to be bound by any theory, it is believed that the plants and plant extracts stimulates bone morphogenic proteins and/or inhibits bone resorption, thereby stimulating bone regeneration and strength. Non-limiting examples of suitable plants and plant extracts as osteoporosis management agents include species of the genus *Taraxacum* and *Amelanchier*, as disclosed in U.S. Patent Publication No. 2005/0106215, and species of the genus *Lindera, Artemisia, Acorus, Carthamus, Carum, Cnidium, Curcuma, Cyperus, Juniperus, Prunus, Iris, Cichorium, Dodonaea, Epimedium, Erigonoum, Soya, Mentha, Ocimum, thymus, Tanacetum, Plantago, Spearmint, Bixa, Vitis, Rosemarinus, Rhus*, and *Anethum*, as disclosed in U.S. Patent Publication No. 2005/0079232.

Phytoestrogen

In certain embodiments, the functional ingredient is at least one phytoestrogen. As used herein, the at least one phytoestrogen may be single phytoestrogen or a plurality of phytoestrogens as a functional ingredient for the sweetener compositions or sweetened composition provided herein. Generally, according to particular embodiments of this invention, the at least one phytoestrogen is present in the sweetener composition or sweetened composition in an amount sufficient to promote health and wellness.

Phytoestrogens are compounds found in plants which can typically be delivered into human bodies by ingestion of the plants or the plant parts having the phytoestrogens. As used herein, "phytoestrogen" refers to any substance which, when introduced into a body causes an estrogen-like effect of any degree. For example, a phytoestrogen may bind to estrogen receptors within the body and have a small estrogen-like effect.

Examples of suitable phytoestrogens for embodiments of this invention include, but are not limited to, isoflavones, stilbenes, lignans, resorcyclic acid lactones, coumestans, coumestrol, equol, and combinations thereof. Sources of suitable phytoestrogens include, but are not limited to, whole grains, cereals, fibers, fruits, vegetables, black cohosh, agave root, black currant, black haw, chasteberries, cramp bark, dong quai root, devil's club root, false unicorn root, *ginseng* root, groundsel herb, licorice, liferoot herb, motherwort herb, peony root, raspberry leaves, rose family plants, sage leaves, sarsaparilla root, saw palmetto berried, wild yam root, yarrow blossoms, legumes, soybeans, soy products (e.g., miso, soy flour, soymilk, soy nuts, soy protein isolate, tempen, or tofu) chick peas, nuts, lentils, seeds, clover, red clover, dandelion leaves, dandelion roots, fenugreek seeds, green tea, hops, red wine, flaxseed, garlic, onions, linseed, borage, butterfly weed, caraway, chaste tree, vitex, dates, dill, fennel seed, gotu kola, milk thistle, pennyroyal, pomegranates, southernwood, soya flour, tansy, and root of the kudzu vine (*pueraria* root) and the like, and combinations thereof.

Isoflavones belong to the group of phytonutrients called polyphenols. In general, polyphenols (also known as "polyphenolics"), are a group of chemical substances found in plants, characterized by the presence of more than one phenol group per molecule.

Suitable phytoestrogen isoflavones in accordance with embodiments of this invention include genistein, daidzein, glycitein, biochanin A, formononetin, their respective naturally occurring glycosides and glycoside conjugates, matairesinol, secoisolariciresinol, enterolactone, enterodiol, textured vegetable protein, and combinations thereof.

Suitable sources of isoflavones for embodiments of this invention include, but are not limited to, soy beans, soy products, legumes, alfalfa spouts, chickpeas, peanuts, and red clover.

Long-Chain Primary Aliphatic Saturated Alcohol

In certain embodiments, the functional ingredient is at least one long chain primary aliphatic saturated alcohol. In one embodiment, a sweetener composition comprises at least one long chain primary aliphatic saturated alcohol, Rebaudioside X, and optionally at least one additive. In another embodiment, a sweetened composition comprises a sweetenable composition and a sweetener composition, wherein the sweetener composition comprises at least one long chain primary aliphatic saturated alcohol, Rebaudioside X, and optionally at least one additive. As used herein, the at least one long chain primary aliphatic saturated alcohol may be single long chain primary aliphatic saturated alcohol or a plurality of long chain primary aliphatic saturated alcohols as a functional ingredient for the sweetener compositions or sweetened composition provided herein. Generally, according to particular embodiments of this invention, the at least one long chain primary aliphatic saturated alcohol is present in the sweetener composition or sweetened composition in an amount sufficient to promote health and wellness.

Long-chain primary aliphatic saturated alcohols are a diverse group of organic compounds. The term alcohol refers to the fact these compounds feature a hydroxyl group (—OH) bound to a carbon atom. The term primary refers to the fact that in these compounds the carbon atom which is bound to the hydroxyl group is bound to only one other carbon atom. The term saturated refers to the fact that these compounds feature no carbon to carbon pi bonds. The term aliphatic refers to the fact that the carbon atoms in these compounds are joined together in straight or branched chains rather than in rings. The term long-chain refers to the fact that the number of carbon atoms in these compounds is at least 8 carbons).

Non-limiting examples of particular long-chain primary aliphatic saturated alcohols for use in particular embodiments of the invention include the 8 carbon atom 1-octanol, the 9 carbon 1-nonanol, the 10 carbon atom 1-decanol, the 12 carbon atom 1-dodecanol, the 14 carbon atom 1-tetradecanol, the 16 carbon atom 1-hexadecanol, the 18 carbon atom 1-octadecanol, the 20 carbon atom 1-eicosanol, the 22 carbon 1-docosanol, the 24 carbon 1-tetracosanol, the 26 carbon 1-hexacosanol, the 27 carbon 1-heptacosanol, the 28 carbon 1-octanosol, the 29 carbon 1-nonacosanol, the 30 carbon 1-triacontanol, the 32 carbon 1-dotriacontanol, and the 34 carbon 1-tetracontanol.

In a particularly desirable embodiment of the invention, the long-chain primary aliphatic saturated alcohols is policosanol. Policosanol is the term for a mixture of long-chain primary aliphatic saturated alcohols composed primarily of 28 carbon 1-octanosol and 30 carbon 1-triacontanol, as well as other alcohols in lower concentrations such as 22 carbon 1-docosanol, 24 carbon 1-tetracosanol, 26 carbon 1-hexacosanol, 27 carbon 1-heptacosanol, 29 carbon 1-nonacosanol, 32 carbon 1-dotriacontanol, and 34 carbon 1-tetracontanol.

Long-chain primary aliphatic saturated alcohols are derived from natural fats and oils. They may be obtained from these sources by using extraction techniques well known to those of ordinary skill in the art. Policosanols can be isolated from a variety of plants and materials including sugar cane (*Saccharum officinarium*), yams (e.g. *Dioscorea opposite*), bran from rice (e.g. *Oryza sativa*), and beeswax. Policosanols may be obtained from these sources by using extraction techniques well known to those of ordinary skill in the art. A description of such extraction techniques can be found in U.S. Pat. Appl. No. 2005/0220868, the disclosure of which is expressly incorporated by reference.

Phytosterols

In certain embodiments, the functional ingredient is at least one phytosterol, phytostanol or combination thereof. Generally, according to particular embodiments of this invention, the at least one phytosterol, phytostanol or combination thereof is present in the sweetener composition or sweetened composition in an amount sufficient to promote health and wellness.

As used herein, the phrases "stanol", "plant stanol" and "phytostanol" are synonymous.

Plant sterols and stanols are present naturally in small quantities in many fruits, vegetables, nuts, seeds, cereals, legumes, vegetable oils, bark of the trees and other plant sources. Although people normally consume plant sterols and stanols every day, the amounts consumed are insufficient to have significant cholesterol-lowering effects or other health benefits. Accordingly, it would be desirable to supplement food and beverages with plant sterols and stanols.

Sterols are a subgroup of steroids with a hydroxyl group at C-3. Generally, phytosterols have a double bond within the steroid nucleus, like cholesterol; however, phytosterols also may comprise a substituted sidechain (R) at C-24, such as an ethyl or methyl group, or an additional double bond. The structures of phytosterols are well known to those of skill in the art.

At least 44 naturally-occurring phytosterols have been discovered, and generally are derived from plants, such as corn, soy, wheat, and wood oils; however, they also may be produced synthetically to form compositions identical to those in nature or having properties similar to those of naturally-occurring phytosterols. According to particular embodiments of this invention, non-limiting examples of phytosterols well known to those or ordinary skill in the art include 4-desmethylsterols (e.g., β-sitosterol, campesterol, stigmasterol, brassicasterol, 22-dehydrobrassicasterol, and Δ5-avenasterol), 4-monomethyl sterols, and 4,4-dimethyl sterols (triterpene alcohols) (e.g., cycloartenol, 24-methylenecycloartanol, and cyclobranol).

As used herein, the phrases "stanol", "plant stanol" and "phytostanol" are synonymous. Phytostanols are saturated sterol alcohols present in only trace amounts in nature and also may be synthetically produced, such as by hydrogenation of phytosterols. According to particular embodiments of this invention, non-limiting examples of phytostanols include β-sitostanol, campestanol, cycloartanol, and saturated forms of other triterpene alcohols.

Both phytosterols and phytostanols, as used herein, include the various isomers such as the α and β isomers (e.g., α-sitosterol and β-sitostanol, which comprise one of the most effective phytosterols and phytostanols, respectively, for lowering serum cholesterol in mammals).

The phytosterols and phytostanols of the present invention also may be in their ester form. Suitable methods for deriving the esters of phytosterols and phytostanols are well known to those of ordinary skill in the art, and are disclosed in U.S. Pat. Nos. 6,589,588, 6,635,774, 6,800,317, and U.S. Patent Publication Number 2003/0045473, the disclosures of which are incorporated herein by reference in their entirety. Non-limiting examples of suitable phytosterol and phytostanol esters include sitosterol acetate, sitosterol oleate, stigmasterol oleate, and their corresponding phytostanol esters. The phytosterols and phytostanols of the present invention also may include their derivatives.

Tabletop Sweetener Compositions

Tabletop sweetener compositions comprising Rebaudioside X are also contemplated herein. The tabletop composition can further include at least one bulking agent, additive, anti-caking agent, functional ingredient or combination thereof. In one embodiment, the Rebaudioside X is amorphous Rebaudioside X. In another embodiment, a Rebaudioside X complex provides the source of Rebaudioside X for the tabletop sweetener compositions.

Suitable "bulking agents" include, but are not limited to, maltodextrin (10 DE, 18 DE, or 5 DE), corn syrup solids (20 or 36 DE), sucrose, fructose, glucose, invert sugar, sorbitol, xylose, ribulose, mannose, xylitol, mannitol, galactitol, erythritol, maltitol, lactitol, isomalt, maltose, tagatose, lactose, inulin, glycerol, propylene glycol, polyols, polydextrose, fructooligosaccharides, cellulose and cellulose derivatives, and the like, and mixtures thereof. Additionally, in accordance with still other embodiments of the invention, granulated sugar (sucrose) or other caloric sweeteners such as crystalline fructose, other carbohydrates, or sugar alcohol can be used as a bulking agent due to their provision of good content uniformity without the addition of significant calories.

As used herein, the phrase "anti-caking agent" and "flow agent" refer to any composition which assists in content uniformity and uniform dissolution. In accordance with particular embodiments, non-limiting examples of anti-caking agents include cream of tartar, calcium silicate, silicon dioxide, microcrystalline cellulose (Avicel, FMC BioPolymer, Philadelphia, Pa.), and tricalcium phosphate. In one embodiment, the anti-caking agents are present in the tabletop functional sweetener composition in an amount from about 0.001 to about 3% by weight of the tabletop functional sweetener composition.

The tabletop sweetener compositions can be packaged in any form known in the art. Non-limiting forms include, but are not limited to, powder form, granular form, packets, tablets, sachets, pellets, cubes and solids.

In one embodiment, the tabletop sweetener composition is a single-serving (portion control) packet comprising a dry-blend. Dry-blend formulations generally may comprise powder or granules. Although the tabletop sweetener composition may be in a packet of any size, an illustrative non-limiting example of conventional portion control tabletop sweetener packets are approximately 2.5 by 1.5 inches and hold approximately 1 gram of a sweetener composition having a sweetness equivalent to 2 teaspoons of granulated sugar (~8 g). The amount of Rebaudioside X in a dry-blend tabletop sweetener formulation can vary. In a particular embodiment, a dry-blend tabletop sweetener formulation may contain Rebaudioside X in an amount from about 1% (w/w) to about 10% (w/w) of the tabletop sweetener composition.

Solid tabletop sweetener embodiments include cubes and tablets. A non-limiting example of conventional cubes are equivalent in size to a standard cube of granulated sugar, which is approximately 2.2×2.2×2.2 cm$^3$ and weigh approximately 8 g. In one embodiment, a solid tabletop sweetener is in the form of a tablet or any other form known to those skilled in the art.

Generally, the amount of functional ingredient in the sweetener composition or sweetened composition varies widely depending on the particular sweetener composition or sweetened composition and the desired functional ingredient. Those of ordinary skill in the art will readily ascertain the appropriate amount of functional ingredient for each sweetener composition or sweetened composition.

Sweetened Compositions

In one embodiment, the Rebaudioside X in sweetened compositions described herein can be amorphous Rebaudioside X or sweetener compositions comprising amorphous Rebaudioside X. The amorphous Rebaudioside X or sweetener composition comprising Rebaudioside X can be incorporated in any known sweetenable composition, such as, for example, pharmaceutical compositions, edible gel mixes and compositions, dental compositions, foodstuffs (confections, condiments, chewing gum, cereal compositions baked goods dairy products, and tabletop sweetener compositions) beverages and beverage products to provide a sweetened composition.

In another embodiment, a sweetened composition comprises a sweetenable composition and amorphous Rebaudioside X. In another embodiment, the sweetened composition comprises a sweetener composition comprising amorphous Rebaudioside X. The sweetened compositions can optionally include additives, sweeteners, functional ingredients and combinations thereof. Because the amorphous form of Rebaudioside X does not exist once the material is dissolved in water/liquid, sweetenable compositions that do not require dissolution of the amorphous Rebaudioside X include dry powdered Rebaudioside X. Liquid or semi-liquid sweetened compositions prepared with amorphous Rebaudioside X will only contain amorphous Rebaudioside X until dissolution, after which the Rebaudioside X will be solvated.

In another embodiment, the Rebaudioside X in the sweetened compositions described herein can be provided by Rebaudioside X complexes or sweetener compositions comprising Rebaudioside X complexes. The Rebaudioside X complex or sweetener composition comprising Rebaudioside X complex can also be incorporated in any known sweetenable compositions, such as, for example, pharmaceutical compositions, edible gel mixes and compositions, dental compositions, foodstuffs (confections, condiments, chewing gum, cereal compositions baked goods dairy products, and tabletop sweetener compositions) beverages and beverage products, to provide a sweetened composition.

In a particular embodiment, a sweetened composition comprises a sweetenable composition and amorphous Rebaudioside X. In a particular embodiment, the sweetenable composition is a beverage or beverage product. The beverage or beverage product can further comprise additional sweeteners, additives and/or functional ingredients, as detailed herein.

In another particular embodiment, a sweetened composition comprises a sweetenable composition and a sweetener composition comprising amorphous Rebaudioside X. The sweetener composition can further comprise additional sweeteners, additives and/or functional ingredients, as detailed herein. In a particular embodiment, the sweetenable composition is a beverage or beverage product.

In a particular embodiment, a sweetened composition comprises a sweetenable composition and a Rebaudioside X complex. In a particular embodiment, the sweetenable composition is a beverage or beverage product. The beverage or beverage product can further comprise additional sweeteners, additives and/or functional ingredients, as detailed herein.

In another particular embodiment, a sweetened composition comprises a sweetenable composition and a sweetener composition comprising a Rebaudioside X complex. The sweetener composition can further comprise additional sweeteners, additives and/or functional ingredients, as detailed herein. In a particular embodiment, the sweetenable composition is a beverage or beverage product.

Pharmaceutical Compositions

In one embodiment, a pharmaceutical composition contains a pharmaceutically active substance and amorphous Rebaudioside X. In another embodiment, a pharmaceutical composition contains a pharmaceutically active substance and a sweetener composition comprising amorphous Rebaudioside X. The amorphous Rebaudioside X or sweetener composition comprising Rebaudioside X can be present as an excipient material in the pharmaceutical composition, which can mask a bitter or otherwise undesirable taste of a pharmaceutically active substance or another excipient material.

In another embodiment, a pharmaceutical composition contains a pharmaceutically active substance and a Rebaudioside X complex. In another embodiment, a pharmaceutical composition contains a pharmaceutically active substance and a sweetener composition comprising a Rebaudioside X complex. The Rebaudioside X complex or sweetener composition comprising a Rebaudioside X complex can be present as an excipient material in the pharmaceutical composition, which can mask a bitter or otherwise undesirable taste of a pharmaceutically active substance or another excipient material.

The pharmaceutical composition may be in the form of a tablet, a capsule, an aerosol, a powder, an effervescent tablet or powder, a syrup, an emulsion, a suspension, a solution, or any other form for providing the pharmaceutical composition to a patient. In particular embodiments, the pharmaceutical composition may be in a form for oral administration, buccal administration, sublingual administration, or any other route of administration as known in the art.

As referred to herein, "pharmaceutically active substance" means any drug, drug formulation, medication, prophylactic agent, therapeutic agent, or other substance having biological activity. As referred to herein, "excipient material" refers to any inactive substance used as a vehicle for an active ingredient, such as any material to facilitate handling, stability, dispersibility, wettability, and/or release kinetics of a pharmaceutically active substance.

Suitable pharmaceutically active substances include, but are not limited to, medications for the gastrointestinal tract or digestive system, for the cardiovascular system, for the central nervous system, for pain or consciousness, for musculo-skeletal disorders, for the eye, for the ear, nose and oropharynx, for the respiratory system, for endocrine problems, for the reproductive system or urinary system, for contraception, for obstetrics and gynecology, for the skin, for infections and infestations, for immunology, for allergic disorders, for nutrition, for neoplastic disorders, for diagnostics, for euthanasia, or other biological functions or disorders. Examples of suitable pharmaceutically active substances for embodiments of the present invention include, but are not limited to, antacids, reflux suppressants, antiflatulents, antidopaminergics, proton pump inhibitors, cytoprotectants, prostaglandin analogues, laxatives, antispasmodics, antidiarrhoeals, bile acid sequestrants, opioids, beta-receptor blockers, calcium channel blockers, diuretics, cardiac glycosides, antiarrhythmics, nitrates, antianginals, vasoconstrictors, vasodilators, peripheral activators, ACE inhibitors, angiotensin receptor blockers, alpha blockers, anticoagulants, heparin, antiplatelet drugs, fibrinolytics, anti-hemophilic factors, haemostatic drugs, hypolipidaemic agents, statins, hynoptics, anaesthetics, antipsychotics, antidepressants, anti-emetics, anticonvulsants, antiepileptics, anxiolytics, barbiturates, movement disorder drugs, stimulants, benzodiazepines, cyclopyrrolones, dopamine antagonists, antihistamines, cholinergics, anticholinergics, emetics, cannabinoids, analgesics, muscle relaxants, antibiotics, aminoglycosides, anti-virals, anti-fungals, anti-inflammatories, anti-gluacoma drugs, sympathomimetics, steroids, ceruminolytics, bronchodilators, NSAIDS, antitussive, mucolytics, decongestants, corticosteroids, androgens, antiandrogens, gonadotropins, growth hormones, insulin, antidiabetics, thyroid hormones, calcitonin, diphosponates, vasopressin analogues, alkalizing agents, quinolones, anticholinesterase, sildenafil, oral contraceptives, Hormone Replacement Therapies, bone regulators, follicle stimulating hormones, luteinizings hormones, gamolenic acid, progestogen, dopamine agonist, oestrogen, prostaglandin, gonadorelin, clomiphene, tamoxifen, diethylstilbestrol, antileprotics, antituberculous drugs, antimalarials, anthelmintics, antiprotozoal, antiserums, vaccines, interferons, tonics, vitamins, cytotoxic drugs, sex hormones, aromatase inhibitors, somatostatin inhibitors, or similar type substances, or combinations thereof. Such components generally are recognized as safe (GRAS) and/or are U.S. Food and Drug Administration (FDA)-approved.

The pharmaceutically active substance is present in the pharmaceutical composition in widely ranging amounts depending on the particular pharmaceutically active agent being used and its intended applications. An effective dose of any of the herein described pharmaceutically active substances can be readily determined by the use of conventional techniques and by observing results obtained under analogous circumstances. In determining the effective dose, a number of factors are considered including, but not limited to: the species of the patient; its size, age, and general health; the specific disease involved; the degree of involvement or the severity of the disease; the response of the individual patient; the particular pharmaceutically active agent administered; the mode of administration; the bioavailability characteristic of the preparation administered; the dose regimen selected; and the use of concomitant medication. The pharmaceutically active substance is included in the pharmaceutically acceptable carrier, diluent, or excipient in an amount sufficient to deliver to a patient a therapeutic amount of the pharmaceutically active substance in vivo in the absence of serious toxic effects when used in generally acceptable amounts. Thus, suitable amounts can be readily discerned by those skilled in the art.

According to particular embodiments of the present invention, the concentration of pharmaceutically active substance in the pharmaceutical composition will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimes should be adjusted over time according to the individual need and the professional judgment of the person administering or supervising the administration of the pharmaceutical compositions, and that the dosage ranges set forth herein are exemplary only and are not intended to limit the scope or practice of the claimed composition. The pharmaceutically active substance may be administered at once, or may be divided into a number of smaller doses to be administered at varying intervals of time.

The pharmaceutical composition also may comprise other pharmaceutically acceptable excipient materials. Examples of suitable excipient materials for embodiments of this invention include, but are not limited to, antiadherents, binders (e.g., microcrystalline cellulose, gum tragacanth, or gelatin), coatings, disintegrants, fillers, diluents, softeners, emulsifiers, flavoring agents, coloring agents, adjuvants, lubricants, functional agents (e.g., nutrients), viscosity modifiers, bulking agents, glidiants (e.g., colloidal silicon dioxide) surface active agents, osmotic agents, diluents, or any other non-active ingredient, or combinations thereof. For example, the pharmaceutical compositions of the present invention may include excipient materials selected from the group consisting of calcium carbonate, coloring agents, whiteners, preservatives, and flavors, triacetin, magnesium stearate, sterotes, natural or artificial flavors, essential oils, plant extracts, fruit essences, gelatins, or combinations thereof.

The excipient material of the pharmaceutical composition may optionally include other artificial or natural sweeteners, bulk sweeteners, or combinations thereof. Bulk sweeteners include both caloric and non-caloric compounds. In a particular embodiment, the additive functions as the bulk sweetener. Non-limiting examples of bulk sweeteners include sucrose, dextrose, maltose, dextrin, dried invert sugar, fructose, high fructose corn syrup, levulose, galactose, corn syrup solids, tagatose, polyols (e.g., sorbitol, mannitol, xylitol, lactitol, erythritol, and maltitol), hydrogenated starch hydrolysates, isomalt, trehalose, and mixtures thereof. In particular embodiments, the bulk sweetener is present in the pharmaceutical composition in widely ranging amounts depending on the degree of sweetness desired. Suitable amounts of both sweeteners would be readily discernable to those skilled in the art.

Edible Gel Mixes and Edible Gel Compositions

In one embodiment, an edible gel or edible gel mix comprises amorphous Rebaudioside X. In another embodiment, an edible gel or edible gel mix comprises a sweetener composition comprising amorphous Rebaudioside X. The edible gel or edible gel mixes can optionally include additives, functional ingredients or combinations thereof.

In another embodiment, an edible gel or edible gel mix comprises a Rebaudioside X complex. In another embodiment, an edible gel or edible gel mix comprises a sweetener composition comprising a Rebaudioside X complex. The edible gel or edible gel mixes can optionally include additives, functional ingredients or combinations thereof.

Edible gels are gels that can be eaten. A gel is a colloidal system in which a network of particles spans the volume of a liquid medium. Although gels mainly are composed of liquids, and thus exhibit densities similar to liquids, gels have the structural coherence of solids due to the network of particles that spans the liquid medium. For this reason, gels generally appear to be solid, jelly-like materials. Gels can be used in a number of applications. For example, gels can be used in foods, paints, and adhesives.

Non-limiting examples of edible gel compositions for use in particular embodiments include gel desserts, puddings, jellies, pastes, trifles, aspics, marshmallows, gummy candies, or the like. Edible gel mixes generally are powdered or granular solids to which a fluid may be added to form an edible gel composition. Non-limiting examples of fluids for use in particular embodiments include water, dairy fluids, dairy analogue fluids, juices, alcohol, alcoholic beverages, and combinations thereof. Non-limiting examples of dairy fluids which may be used in particular embodiments include milk, cultured milk, cream, fluid whey, and mixtures thereof. Non-limiting examples of dairy analogue fluids which may be used in particular embodiments include, for example, soy milk and non-dairy coffee whitener. Because edible gel products found in the marketplace typically are sweetened with sucrose, it is desirable to sweeten edible gels with an alternative sweetener in order provide a low-calorie or non-calorie alternative.

As used herein, the term "gelling ingredient" denotes any material that can form a colloidal system within a liquid medium. Non-limiting examples of gelling ingredients for use in particular embodiments include gelatin, alginate, carageenan, gum, pectin, konjac, agar, food acid, rennet, starch, starch derivatives, and combinations thereof. It is well known to those having ordinary skill in the art that the amount of gelling ingredient used in an edible gel mix or an edible gel composition varies considerably depending on a number of factors, such as the particular gelling ingredient used, the particular fluid base used, and the desired properties of the gel.

It is well known to those having ordinary skill in the art that the edible gel mixes and edible gels may be prepared using other ingredients in addition to Rebaudioside X and the gelling agent. Non-limiting examples of other ingredients for use in particular embodiments include a food acid, a salt of a food acid, a buffering system, a bulking agent, a sequestrant, a cross-linking agent, one or more flavors, one or more colors, and combinations thereof. Non-limiting examples of food acids for use in particular embodiments include citric acid, adipic acid, fumaric acid, lactic acid, malic acid, and combinations thereof. Non-limiting examples of salts of food acids for use in particular embodiments include sodium salts of food acids, potassium salts of food acids, and combinations thereof. Non-limiting examples of bulking agents for use in particular embodiments include raftilose, isomalt, sorbitol, polydextrose, maltodextrin, and combinations thereof. Non-limiting examples of sequestrants for use in particular embodiments include calcium disodium ethylene tetra-acetate, glucono delta-lactone, sodium gluconate, potassium gluconate, ethylenediaminetetraacetic acid (EDTA), and combinations thereof. Non-limiting examples of cross-linking agents for use in particular embodiments include calcium ions, magnesium ions, sodium ions, and combinations thereof.

Dental Compositions

In one embodiment, a dental composition comprises amorphous Rebaudioside X. In another embodiment, a dental composition comprises a sweetener composition comprising amorphous Rebaudioside X. Dental compositions generally comprise an active dental substance and a base material. Amorphous Rebaudioside X, or a sweetener composition comprising amorphous Rebaudioside X, can be used as the base material to sweeten the dental composition.

In one embodiment, a dental composition comprises a Rebaudioside X complex. In another embodiment, a dental composition comprises a sweetener composition comprising a Rebaudioside X complex. Dental compositions generally comprise an active dental substance and a base material. Rebaudioside X complexes, or a sweetener composition comprising Rebaudioside X complexes, can be used as the base material to sweeten the dental composition.

The dental composition may be in the form of any oral composition used in the oral cavity such as mouth freshening agents, gargling agents, mouth rinsing agents, toothpaste, tooth polish, dentifrices, mouth sprays, teeth-whitening agent, dental floss, and the like, for example.

As referred to herein, "active dental substance" means any composition which can be used to improve the aesthetic appearance and/or health of teeth or gums or prevent dental caries. As referred to herein, "base material" refers to any inactive substance used as a vehicle for an active dental substance, such as any material to facilitate handling, stability, dispersibility, wettability, foaming, and/or release kinetics of an active dental substance.

Suitable active dental substances for embodiments of this invention include, but are not limited to, substances which remove dental plaque, remove food from teeth, aid in the elimination and/or masking of halitosis, prevent tooth decay, and prevent gum disease (i.e., Gingiva). Examples of suitable active dental substances for embodiments of the present invention include, but are not limited to, anticarries drugs, fluoride, sodium fluoride, sodium monofluorophosphate, stannos fluoride, hydrogen peroxide, carbamide peroxide (i.e., urea peroxide), antibacterial agents, plaque removing agents, stain removers, anticalculus agents, abrasives, baking soda, percarbonates, perborates of alkali and alkaline earth metals, or similar type substances, or combinations thereof. Such components generally are recognized as safe (GRAS) and/or are U.S. Food and Drug Administration (FDA)-approved.

According to particular embodiments of the invention, the active dental substance is present in the dental composition in an amount ranging from about 50 ppm to about 3000 ppm of the dental composition. Generally, the active dental substance is present in the dental composition in an amount effective to at least improve the aesthetic appearance and/or health of teeth or gums marginally or prevent dental caries. For example, a dental composition comprising a toothpaste may include an active dental substance comprising fluoride in an amount of about 850 to 1,150 ppm.

The dental composition also may comprise other base materials in addition to Rebaudioside X. Examples of suitable base materials for embodiments of this invention include, but are not limited to, water, sodium lauryl sulfate or other sulfates, humectants, enzymes, vitamins, herbs, calcium, flavorings (e.g., mint, bubblegum, cinnamon, lemon, or orange), surface-active agents, binders, preservatives, gelling agents, pH modifiers, peroxide activators, stabilizers, coloring agents, or similar type materials, and combinations thereof.

The base material of the dental composition may optionally include other artificial or natural sweeteners, bulk sweeteners, or combinations thereof. Bulk sweeteners include both caloric and non-caloric compounds. Non-limiting examples of bulk sweeteners include sucrose, dextrose, maltose, dextrin, dried invert sugar, fructose, high fructose corn syrup, levulose, galactose, corn syrup solids, tagatose, polyols (e.g., sorbitol, mannitol, xylitol, lactitol, erythritol, and maltitol), hydrogenated starch hydrolysates, isomalt, trehalose, and mixtures thereof.

Generally, the amount of bulk sweetener present in the dental composition ranges widely depending on the particular embodiment of the dental composition and the desired degree of sweetness. Those of ordinary skill in the art will readily ascertain the appropriate amount of bulk sweetener. In particular embodiments, the bulk sweetener is present in the dental composition in an amount in the range of about 0.1 to about 5 weight percent of the dental composition.

According to particular embodiments of the invention, the base material is present in the dental composition in an amount ranging from about 20 to about 99 percent by weight of the dental composition. Generally, the base material is present in an amount effective to provide a vehicle for an active dental substance.

Generally, the amount of the sweetener varies widely depending on the nature of the particular dental composition and the desired degree of sweetness. Those skilled in the art will be able to discern a suitable amount of sweetener for such dental composition. In a particular embodiment, amorphous Rebaudioside X is present in the dental composition in an amount in the range of about 1 to about 5,000 ppm of the dental composition and the at least one additive is present in the dental composition in an amount in the range of about 0.1 to about 100,000 ppm of the dental composition.

Foodstuffs include, but are not limited to, confections, condiments, chewing gum, cereal, baked goods, and dairy products.

Confections

In one embodiment, a confection comprises amorphous Rebaudioside X. In another embodiment, a confection comprises a sweetener composition comprising amorphous Rebaudioside X.

In one embodiment, a confection comprises a Rebaudioside X complex. In another embodiment, a confection comprises a sweetener composition comprising a Rebaudioside X complex.

As referred to herein, "confection" can mean a sweet, a lollie, a confectionery, or similar term. The confection generally contains a base composition component and a sweetener component. The confection may be in the form of any food that is typically perceived to be rich in sugar or is typically sweet. According to particular embodiments of the present invention, the confections may be bakery products such as pastries; desserts such as yogurt, jellies, drinkable jellies, puddings, Bavarian cream, blancmange, cakes, brownies, mousse and the like, sweetened food products eaten at tea time or following meals; frozen foods; cold confections, e. g. types of ice cream such as ice cream, ice milk, lacto-ice and the like (food products in which sweeteners and various other types of raw materials are added to milk products, and the resulting mixture is agitated and frozen), and ice confections such as sherbets, dessert ices and the like (food products in which various other types of raw materials are added to a sugary liquid, and the resulting mixture is agitated and frozen); general confections, e.g., baked confections or steamed confections such as crackers, biscuits, buns with bean-jam filling, halvah, alfajor, and the like; rice cakes and snacks; table top products; general sugar confections such as chewing gum (e.g. including compositions which comprise a substantially water-insoluble, chewable gum base, such as chicle or substitutes thereof, including jetulong, guttakay rubber or certain comestible natural synthetic resins or waxes), hard candy, soft candy, mints, nougat candy, jelly beans, fudge, toffee, taffy, Swiss milk tablet, licorice candy, chocolates, gelatin candies, marshmallow, marzipan, divinity, cotton candy, and the like; sauces including fruit flavored sauces, chocolate sauces and the like; edible gels; crémes including butter crémes, flour pastes, whipped cream and the like; jams including strawberry jam, marmalade and the like; and breads including sweet breads and the like or other starch products, and combinations thereof.

As referred to herein, "base composition" means any composition which can be a food item and provides a matrix for carrying the sweetener component.

Suitable base compositions for embodiments of this invention may include flour, yeast, water, salt, butter, eggs, milk, milk powder, liquor, gelatin, nuts, chocolate, citric acid, tartaric acid, fumaric acid, natural flavors, artificial flavors, colorings, polyols, sorbitol, isomalt, maltitol, lactitol, malic acid, magnesium stearate, lecithin, hydrogenated glucose syrup, glycerine, natural or synthetic gum, starch, and the like, and combinations thereof. Such components generally are recognized as safe (GRAS) and/or are U.S. Food and Drug Administration (FDA)-approved. According to particular embodiments of the invention, the base composition is present in the confection in an amount ranging from about 0.1 to about 99 weight percent of the confection.

The base composition of the confection may optionally include other artificial or natural sweeteners, bulk sweeteners, or combinations thereof. Bulk sweeteners include both caloric and non-caloric compounds. Non-limiting examples of bulk sweeteners include sucrose, dextrose, maltose, dextrin, dried invert sugar, fructose, high fructose corn syrup, levulose, galactose, corn syrup solids, tagatose, polyols (e.g., sorbitol, mannitol, xylitol, lactitol, erythritol, and maltitol), hydrogenated starch hydrolysates, isomalt, trehalose, and mixtures thereof. Generally, the amount of bulk sweetener present in the confection ranges widely depending on the particular embodiment of the confection and the desired degree of sweetness. Those of ordinary skill in the art will readily ascertain the appropriate amount of bulk sweetener.

In a particular embodiment, a confection comprises Rebaudioside X and a base composition. Generally, the amount of Rebaudioside X in the confection ranges widely depending on the particular embodiment of the confection and the desired degree of sweetness. Those of ordinary skill in the art will readily ascertain the appropriate amount of sweetener. In a particular embodiment, Rebaudioside X is present in the confection in an amount in the range of about 30 ppm to about 6000 ppm of the confection. In another embodiment, Rebaudioside X is present in the confection in an amount in the range of about 1 ppm to about 10,000 ppm of the confection. In embodiments where the confection comprises hard candy, Rebaudioside X is present in an amount in the range of about 150 ppm to about 2250 ppm of the hard candy.

Condiment Compositions

In one embodiment, a condiment comprises amorphous Rebaudioside X. In another embodiment a condiment comprises a sweetener composition comprising amorphous Rebaudioside X.

In another embodiment, a condiment comprises a Rebaudioside X complex. In another embodiment a condiment comprises a sweetener composition comprising a Rebaudioside X complex.

Condiments, as used herein, are compositions used to enhance or improve the flavor of a food or beverage. Non-limiting examples of condiments include ketchup (catsup); mustard; barbecue sauce; butter; chili sauce; chutney; cocktail sauce; curry; dips; fish sauce; horseradish; hot sauce; jellies, jams, marmalades, or preserves; mayonnaise; peanut butter; relish; remoulade; salad dressings (e.g., oil and vinegar, Caesar, French, ranch, bleu cheese, Russian, Thousand Island, Italian, and balsamic vinaigrette), salsa; sauerkraut; soy sauce; steak sauce; syrups; tartar sauce; and Worcestershire sauce.

Condiment bases generally comprise a mixture of different ingredients, non-limiting examples of which include vehicles (e.g., water and vinegar); spices or seasonings (e.g., salt, pepper, garlic, mustard seed, onion, paprika, turmeric, and combinations thereof); fruits, vegetables, or their products (e.g., tomatoes or tomato-based products (paste, puree), fruit juices, fruit juice peels, and combinations thereof); oils or oil emulsions, particularly vegetable oils; thickeners (e.g., xanthan gum, food starch, other hydrocolloids, and combinations thereof); and emulsifying agents (e.g., egg yolk solids, protein, gum arabic, carob bean gum, guar gum, gum karaya, gum tragacanth, carageenan, pectin, propylene glycol esters of alginic acid, sodium carboxymethyl-cellulose, polysorbates, and combinations thereof). Recipes for condiment bases and methods of making condiment bases are well known to those of ordinary skill in the art.

Generally, condiments also comprise caloric sweeteners, such as sucrose, high fructose corn syrup, molasses, honey, or brown sugar. In exemplary embodiments of the condiments provided herein, Rebaudioside X or sweetener compositions comprising Rebaudioside X are used instead of traditional caloric sweeteners. Accordingly, a condiment composition desirably comprises Rebaudioside X or a sweetener composition comprising Rebaudioside X and a condiment base.

The condiment composition optionally may include other natural and/or synthetic high-potency sweeteners, bulk sweeteners, pH modifying agents (e.g., lactic acid, citric acid, phosphoric acid, hydrochloric acid, acetic acid, and combinations thereof), fillers, functional agents (e.g., pharmaceutical agents, nutrients, or components of a food or plant), flavorings, colorings, or combinations thereof.

Chewing Gum Compositions

In one embodiment, a chewing gum composition comprises amorphous Rebaudioside X. In another embodiment, a chewing gum composition comprises a sweetener composition comprising amorphous Rebaudioside X.

In another embodiment, a chewing gum composition comprises a Rebaudioside X complex. In another embodiment, a chewing gum composition comprises a sweetener composition comprising a Rebaudioside X complex.

Chewing gum compositions generally comprise a water-soluble portion and a water-insoluble chewable gum base portion. The water soluble portion, which typically includes the sweetener or sweetener composition, dissipates with a portion of the flavoring agent over a period of time during chewing while the insoluble gum base portion is retained in the mouth. The insoluble gum base generally determines whether a gum is considered chewing gum, bubble gum, or a functional gum.

The insoluble gum base, which is generally present in the chewing gum composition in an amount in the range of about 15 to about 35 weight percent of the chewing gum composition, generally comprises combinations of elastomers, softeners (plasticizers), emulsifiers, resins, and fillers. Such components generally are considered food grade, recognized as safe (GRA), and/or are U.S. Food and Drug Administration (FDA)-approved.

Elastomers, the primary component of the gum base, provide the rubbery, cohesive nature to gums and can include one or more natural rubbers (e.g., smoked latex, liquid latex, or guayule); natural gums (e.g., jelutong, perillo, sorva, massaranduba balata, massaranduba chocolate, nispero, rosindinha, chicle, and gutta hang kang); or synthetic elastomers (e.g., butadiene-styrene copolymers, isobutylene-isoprene copolymers, polybutadiene, polyisobutylene, and vinyl polymeric elastomers). In a particular embodiment, the elastomer is present in the gum base in an amount in the range of about 3 to about 50 weight percent of the gum base.

Resins are used to vary the firmness of the gum base and aid in softening the elastomer component of the gum base. Non-limiting examples of suitable resins include a rosin ester, a terpene resin (e.g., a terpene resin from α-pinene, β-pinene and/or d-limonene), polyvinyl acetate, polyvinyl alcohol, ethylene vinyl acetate, and vinyl acetate-vinyl laurate copolymers. Non-limiting examples of rosin esters include a glycerol ester of a partially hydrogenated rosin, a glycerol ester of a polymerized rosin, a glycerol ester of a partially dimerized rosin, a glycerol ester of rosin, a pentaerythritol ester of a partially hydrogenated rosin, a methyl ester of rosin, or a methyl ester of a partially hydrogenated rosin. In a particular embodiment, the resin is present in the gum base in an amount in the range of about 5 to about 75 weight percent of the gum base.

Softeners, which also are known as plasticizers, are used to modify the ease of chewing and/or mouthfeel of the chewing gum composition. Generally, softeners comprise oils, fats, waxes, and emulsifiers. Non-limiting examples of oils and fats include tallow, hydrogenated tallow, large, hydrogenated or partially hydrogenated vegetable oils (e.g., soybean, canola, cottonseed, sunflower, palm, coconut, corn, safflower, or palm kernel oils), cocoa butter, glycerol monostearate, glycerol triacetate, glycerol abietate, leithin, monoglycerides, diglycerides, triglycerides acetylated monoglycerides, and free fatty acids. Non-limiting examples of waxes include polypropylene/polyethylene/Fisher-Tropsch waxes, paraffin, and microcrystalline and natural waxes (e.g., candelilla, beeswax and carnauba). Microcrystalline waxes, especially those with a high degree of crystallinity and a high melting point, also may be considered as bodying agents or textural modifiers. In a particular embodiment, the softeners are present in the gum base in an amount in the range of about 0.5 to about 25 weight percent of the gum base.

Emulsifiers are used to form a uniform dispersion of the insoluble and soluble phases of the chewing gum composition and also have plasticizing properties. Suitable emulsifiers include glycerol monostearate (GMS), lecithin (Phosphatidyl choline), polyglycerol polyricinoleic acid (PPGR), mono and diglycerides of fatty acids, glycerol distearate, tracetin, acetylated monoglyceride, glycerol triactetate, and magnesium stearate. In a particular embodiment, the emulsifiers are present in the gum base in an amount in the range of about 2 to about 30 weight percent of the gum base.

The chewing gum composition also may comprise adjuvants or fillers in either the gum base and/or the soluble portion of the chewing gum composition. Suitable adjuvants and fillers include lecithin, inulin, polydextrin, calcium carbonate, magnesium carbonate, magnesium silicate, ground limestome, aluminum hydroxide, aluminum silicate, talc, clay, alumina, titanium dioxide, and calcium phosphate. In particular embodiments, lecithin can be used as an inert filler to decrease the stickiness of the chewing gum composition. In other particular embodiments, lactic acid copolymers, proteins (e.g., gluten and/or zein) and/or guar can be used to create a gum that is more readily biodegradable. The adjuvants or fillers are generally present in the gum base in an amount up to about 20 weight percent of the gum base. Other optional ingredients include coloring agents, whiteners, preservatives, and flavors.

In particular embodiments of the chewing gum composition, the gum base comprises about 5 to about 95 weight percent of the chewing gum composition, more desirably about 15 to about 50 weight percent of the chewing gum composition, and even more desirably from about 20 to about 30 weight percent of the chewing gum composition.

The soluble portion of the chewing gum composition may optionally include other artificial or natural sweeteners, bulk sweeteners, softeners, emulsifiers, flavoring agents, coloring agents, adjuvants, fillers, functional agents (e.g., pharmaceutical agents or nutrients), or combinations thereof. Suitable examples of softeners and emulsifiers are described above.

Bulk sweeteners include both caloric and non-caloric compounds. Non-limiting examples of bulk sweeteners include sucrose, dextrose, maltose, dextrin, dried invert sugar, fructose, high fructose corn syrup, levulose, galactose, corn syrup solids, tagatose, polyols (e.g., sorbitol, mannitol, xylitol, lactitol, erythritol, and maltitol), hydrogenated starch hydrolysates, isomalt, trehalose, and mixtures thereof. In particular embodiments, the bulk sweetener is present in the chewing gum composition in an amount in the range of about 1 to about 75 weight percent of the chewing gum composition.

Flavoring agents may be used in either the insoluble gum base or soluble portion of the chewing gum composition. Such flavoring agents may be natural or artificial flavors. In a particular embodiment, the flavoring agent comprises an essential oil, such as an oil derived from a plant or a fruit, peppermint oil, spearmint oil, other mint oils, clove oil, cinnamon oil, oil of wintergreen, bay, thyme, cedar leaf, nutmeg, allspice, sage, mace, and almonds. In another particular embodiment, the flavoring agent comprises a plant extract or a fruit essence such as apple, banana, watermelon, pear, peach, grape, strawberry, raspberry, cherry, plum, pineapple, apricot, and mixtures thereof. In still another particular embodiment, the flavoring agent comprises a citrus flavor, such as an extract, essence, or oil of lemon, lime, orange, tangerine, grapefruit, citron, or kumquat.

In a particular embodiment, a chewing gum composition comprises Rebaudioside X or a sweetener composition comprising Rebaudioside X and a gum base. In a particular embodiment, Rebaudioside X is present in the chewing gum composition in an amount in the range of about 1 ppm to about 10,000 ppm of the chewing gum composition.

Cereal Compositions

In one embodiment, a cereal composition comprises amorphous Rebaudioside X. In another embodiment, a cereal composition comprises a sweetener composition comprising amorphous Rebaudioside X.

In one embodiment, a cereal composition comprises a Rebaudioside X complex. In another embodiment, a cereal composition comprises a sweetener composition comprising a Rebaudioside X complex.

Cereal compositions typically are eaten either as staple foods or as snacks. Non-limiting examples of cereal compositions for use in particular embodiments include ready-to-eat cereals as well as hot cereals. Ready-to-eat cereals are cereals which may be eaten without further processing (i.e. cooking) by the consumer. Examples of ready-to-eat cereals include breakfast cereals and snack bars. Breakfast cereals typically are processed to produce a shredded, flaky, puffy, or extruded form. Breakfast cereals generally are eaten cold and are often mixed with milk and/or fruit. Snack bars include, for example, energy bars, rice cakes, granola bars, and nutritional bars. Hot cereals generally are cooked, usually in either milk or water, before being eaten. Non-limiting examples of hot cereals include grits, porridge, polenta, rice, and rolled oats.

Cereal compositions generally comprise at least one cereal ingredient. As used herein, the term "cereal ingredient" denotes materials such as whole or part grains, whole or part seeds, and whole or part grass. Non-limiting examples of cereal ingredients for use in particular embodiments include maize, wheat, rice, barley, bran, bran endosperm, bulgur, soghums, millets, oats, rye, triticale, buchwheat, fonio, quinoa, bean, soybean, amaranth, teff, spelt, and kaniwa.

In a particular embodiment, the cereal composition comprises Rebaudioside X or a sweetener composition comprising Rebaudioside X and at least one cereal ingredient. Rebaudioside X or the sweetener composition comprising Rebaudioside X may be added to the cereal composition in a variety of ways, such as, for example, as a coating, as a frosting, as a glaze, or as a matrix blend (i.e. added as an ingredient to the cereal formulation prior to the preparation of the final cereal product).

Accordingly, in a particular embodiment, Rebaudioside X or a sweetener composition comprising Rebaudioside X is added to the cereal composition as a matrix blend. In one embodiment, Rebaudioside X or a sweetener composition comprising Rebaudioside X is blended with a hot cereal prior to cooking to provide a sweetened hot cereal product. In another embodiment, Rebaudioside X or a sweetener comprising Rebaudioside X is blended with the cereal matrix before the cereal is extruded.

In another particular embodiment, Rebaudioside X or a sweetener composition comprising Rebaudioside X is added to the cereal composition as a coating, such as, for example, by combining Rebaudioside X or a sweetener comprising Rebaudioside X with a food grade oil and applying the mixture onto the cereal. In a different embodiment, Rebaudioside X or a sweetener composition comprising Rebaudioside X and the food grade oil may be applied to the cereal separately, by applying either the oil or the sweetener first. Non-limiting examples of food grade oils for use in particular embodiments include vegetable oils such as corn oil, soybean oil, cottonseed oil, peanut oil, coconut oil, canola oil, olive oil, sesame seed oil, palm oil, palm kernel oil, and mixtures thereof. In yet another embodiment, food grade fats may be used in place of the oils, provided that the fat is melted prior to applying the fat onto the cereal.

In another embodiment, the Rebaudioside X or a sweetener composition comprising Rebaudioside X is added to the cereal composition as a glaze. Non-limiting examples of glazing agents for use in particular embodiments include corn syrup, honey syrups and honey syrup solids, maple syrups and maple syrup solids, sucrose, isomalt, polydextrose, polyols, hydrogenated starch hydrosylate, aqueous solutions thereof, and mixtures thereof. In another such embodiment, Rebaudioside X or a sweetener composition comprising Rebaudioside X is added as a glaze by combining with a glazing agent and a food grade oil or fat and applying the mixture to the cereal. In yet another embodiment, a gum system, such as, for example, gum acacia, carboxymethyl cellulose, or algin, may be added to the glaze to provide structural support. In addition, the glaze also may include a coloring agent, and also may include a flavor.

In another embodiment, Rebaudioside X or a sweetener composition comprising Rebaudioside X is added to the cereal composition as a frosting. In one such embodiment, Rebaudioside X or a sweetener composition comprising Rebaudioside X is combined with water and a frosting agent and then applied to the cereal. Non-limiting examples of frosting agents for use in particular embodiments include maltodextrin, sucrose, starch, polyols, and mixtures thereof. The frosting also may include a food grade oil, a food grade fat, a coloring agent, and/or a flavor.

Generally, the amount of Rebaudioside X in a cereal composition varies widely depending on the particular type of cereal composition and its desired sweetness. Those of ordinary skill in the art can readily discern the appropriate amount of sweetener to put in the cereal composition. In a particular embodiment, Rebaudioside X is present in the cereal composition in an amount in the range of about 0.02 to about 1.5 weight percent of the cereal composition and the at least one additive is present in the cereal composition in an amount in the range of about 1 to about 5 weight percent of the cereal composition.

Baked Goods

In one embodiment, a baked good comprises amorphous Rebaudioside X. In another embodiment, a baked good comprises a sweetener composition comprising amorphous Rebaudioside X.

In another embodiment, a baked good comprises a Rebaudioside X complex. In another embodiment, a baked good comprises a sweetener composition comprising a Rebaudioside X complex.

Baked goods, as used herein, include ready to eat and all ready to bake products, flours, and mixes requiring preparation before serving. Non-limiting examples of baked goods include cakes, crackers, cookies, brownies, muffins, rolls, bagels, donuts, strudels, pastries, croissants, biscuits, bread, bread products, and buns.

Preferred baked goods in accordance with embodiments of this invention can be classified into three groups: bread-type doughs (e.g., white breads, variety breads, soft buns, hard rolls, bagels, pizza dough, and flour tortillas), sweet doughs (e.g., danishes, croissants, crackers, puff pastry, pie crust, biscuits, and cookies), and batters (e.g., cakes such as sponge, pound, devil's food, cheesecake, and layer cake, donuts or other yeast raised cakes, brownies, and muffins). Doughs generally are characterized as being flour-based, whereas batters are more water-based.

Baked goods in accordance with particular embodiments of this invention generally comprise a combination of sweetener, water, and fat. Baked goods made in accordance with many embodiments of this invention also contain flour in order to make a dough or a batter. The term "dough" as used herein is a mixture of flour and other ingredients stiff enough to knead or roll. The term "batter" as used herein consists of flour, liquids such as milk or water, and other ingredients, and is thin enough to pour or drop from a spoon. Desirably, in accordance with particular embodiments of the invention, the flour is present in the baked goods in an amount in the range of about 15 to about 60% on a dry weight basis, more desirably from about 23 to about 48% on a dry weight basis.

The type of flour may be selected based on the desired product. Generally, the flour comprises an edible non-toxic flour that is conventionally utilized in baked goods. According to particular embodiments, the flour may be a bleached bake flour, general purpose flour, or unbleached flour. In other particular embodiments, flours also may be used that have been treated in other manners. For example, in particular embodiments flour may be enriched with additional vitamins, minerals, or proteins. Non-limiting examples of flours suitable for use in particular embodiments of the invention include wheat, corn meal, whole grain, fractions of whole grains (wheat, bran, and oatmeal), and combinations thereof. Starches or farinaceous material also may be used as the flour in particular embodiments. Common food starches generally are derived from potato, corn, wheat, barley, oat, tapioca, arrow root, and sago. Modified starches and pregelatinized starches also may be used in particular embodiments of the invention.

The type of fat or oil used in particular embodiments of the invention may comprise any edible fat, oil, or combination thereof that is suitable for baking. Non-limiting examples of fats suitable for use in particular embodiments of the invention include vegetable oils, tallow, lard, marine oils, and combinations thereof. According to particular embodiments, the fats may be fractionated, partially hydrogenated, and/or interesterified. In another particular embodiment, the fat desirably comprises reduced, low calorie, or non-digestible fats, fat substitutes, or synthetic fats. In yet another particular embodiment, shortenings, fats, or mixtures of hard and soft fats also may be used. In particular embodiments, shortenings may be derived principally from triglycerides derived from vegetable sources (e.g., cotton seed oil, soybean oil, peanut oil, linseed oil, sesame oil, palm oil, palm kernel oil, rapeseed oil, safflower oil, coconut oil, corn oil, sunflower seed oil, and mixtures thereof). Synthetic or natural triglycerides of fatty acids having chain lengths from 8 to 24 carbon atoms also may be used in particular embodiments. Desirably, in accordance with particular embodiments of this invention, the fat is present in the baked good in an amount in the range of about 2 to about 35% by weight on a dry basis, more desirably from about 3 to about 29% by weight on a dry basis.

Baked goods in accordance with particular embodiments of this invention also comprise water in amounts sufficient to provide the desired consistency, enabling proper forming, machining and cutting of the baked good prior or subsequent to cooking. The total moisture content of the baked good includes any water added directly to the baked good as well as water present in separately added ingredients (e.g., flour, which generally includes about 12 to about 14% by weight moisture). Desirably, in accordance with particular embodiments of this invention, the water is present in the baked good in an amount up to about 25% by weight of the baked good.

Baked goods in accordance with particular embodiments of this invention also may comprise a number of additional conventional ingredients such as leavening agents, flavors, colors, milk, milk by-products, egg, egg by-products, cocoa, vanilla or other flavoring, as well as inclusions such as nuts, raisins, cherries, apples, apricots, peaches, other fruits, citrus peel, preservative, coconuts, flavored chips such a chocolate chips, butterscotch chips, and caramel chips, and combinations thereof. In particular embodiments, the baked goods may also comprise emulsifiers, such as lecithin and monoglycerides.

According to particular embodiments of this invention, leavening agents may comprise chemical leavening agents or yeast leavening agents. Non-limiting examples of chemical leavening agents suitable for use in particular embodiments of this invention include baking soda (e.g., sodium, potassium, or aluminum bicarbonate), baking acid (e.g., sodium aluminum phosphate, monocalcium phosphate, or dicalcium phosphate), and combinations thereof.

In accordance with another particular embodiment of this invention, cocoa may comprise natural or "Dutched" chocolate from which a substantial portion of the fat or cocoa butter has been expressed or removed by solvent extraction, pressing, or other means. In a particular embodiment, it may be necessary to reduce the amount of fat in a baked good comprising chocolate because of the additional fat present in cocoa butter. In particular embodiments, it may be necessary to add larger amounts of chocolate as compared to cocoa in order to provide an equivalent amount of flavoring and coloring.

Baked goods generally also comprise caloric sweeteners, such as sucrose, high fructose corn syrup, erythritol, molasses, honey, or brown sugar. In exemplary embodiments of the baked goods provided herein, the caloric sweetener is replaced partially or totally with Rebaudioside X or a sweetener composition comprising Rebaudioside X. Accordingly, in one embodiment a baked good comprises Rebaudioside X or a sweetener composition comprising Rebaudioside X in combination with a fat, water, and optionally flour. In a particular embodiment, the baked good optionally may include other natural and/or synthetic high-potency sweeteners and/or bulk sweeteners.

Dairy Products

In one embodiment, a dairy product comprises amorphous Rebaudioside X. In another embodiment, a dairy product comprises a sweetener composition comprising amorphous Rebaudioside X.

In another embodiment, a dairy product comprises a Rebaudioside X complex. In another embodiment, a dairy product comprises a sweetener composition comprising a Rebaudioside X complex.

Dairy products and processes for making dairy products suitable for use in this invention are well known to those of ordinary skill in the art. Dairy products, as used herein, comprise milk or foodstuffs produced from milk. Non-limiting examples of dairy products suitable for use in embodiments of this invention include milk, milk cream, sour cream, crème fraiche, buttermilk, cultured buttermilk, milk powder, condensed milk, evaporated milk, butter, cheese, cottage cheese, cream cheese, yogurt, ice cream, frozen custard, frozen yogurt, gelato, vla, piima, filmjolk, kajmak, kephir, viili, kumiss, airag, ice milk, casein, ayran, lassi, khoa, or combinations thereof.

Milk is a fluid secreted by the mammary glands of female mammals for the nourishment of their young. The female ability to produce milk is one of the defining characteristics of mammals and provides the primary source of nutrition for newborns before they are able to digest more diverse foods. In particular embodiments of this invention, the dairy products are derived from the raw milk of cows, goats, sheep, horses, donkeys, camels, water buffalo, yaks, reindeer, moose, or humans.

In particular embodiments of this invention, the processing of the dairy product from raw milk generally comprises the steps of pasteurizing, creaming, and homogenizing. Although raw milk may be consumed without pasteurization, it usually is pasteurized to destroy harmful microorganisms such as bacteria, viruses, protozoa, molds, and yeasts. Pasteurizing generally comprises heating the milk to a high temperature for a short period of time to substantially reduce the number of microorganisms, thereby reducing the risk of disease.

Creaming traditionally follows pasteurization step, and involves the separation of milk into a higher-fat cream layer and a lower-fat milk layer. Milk will separate into milk and cream layers upon standing for twelve to twenty-four hours. The cream rises to the top of the milk layer and may be skimmed and used as a separate dairy product. Alternatively, centrifuges may be used to separate the cream from the milk.

The remaining milk is classified according to the fat content of the milk, non-limiting examples of which include whole, 2%, 1%, and skim milk.

After removing the desired amount of fat from the milk by creaming, milk is often homogenized. Homogenization prevents cream from separating from the milk and generally involves pumping the milk at high pressures through narrow tubes in order to break up fat globules in the milk. Pasteurization, creaming, and homogenization of milk are common but are not required to produce consumable dairy products. Accordingly, suitable dairy products for use in embodiments of this invention may undergo no processing steps, a single processing step, or combinations of the processing steps described herein. Suitable dairy products for use in embodiments of this invention may also undergo processing steps in addition to or apart from the processing steps described herein.

Particular embodiments of this invention comprise dairy products produced from milk by additional processing steps. As described above, cream may be skimmed from the top of milk or separated from the milk using machine-centrifuges. In a particular embodiment, the dairy product comprises sour cream, a dairy product rich in fats that is obtained by fermenting cream using a bacterial culture. The bacteria produce lactic acid during fermentation, which sours and thickens the cream. In another particular embodiment, the dairy product comprises crème fraiche, a heavy cream slightly soured with bacterial culture in a similar manner to sour cream. Crème fraiche ordinarily is not as thick or as sour as sour cream. In yet another particular embodiment, the dairy product comprises cultured buttermilk. Cultured buttermilk is obtained by adding bacteria to milk. The resulting fermentation, in which the bacterial culture turns lactose into lactic acid, gives cultured buttermilk a sour taste. Although it is produced in a different manner, cultured buttermilk generally is similar to traditional buttermilk, which is a by-product of butter manufacture.

According to other particular embodiments of this invention, the dairy products comprise milk powder, condensed milk, evaporated milk, or combinations thereof. Milk powder, condensed milk, and evaporated milk generally are produced by removing water from milk. In a particular embodiment, the dairy product comprises a milk powder comprising dried milk solids with a low moisture content. In another particular embodiment, the dairy product comprises condensed milk. Condensed milk generally comprises milk with a reduced water content and added sweetener, yielding a thick, sweet product with a long shelf-life. In yet another particular embodiment, the dairy product comprises evaporated milk. Evaporated milk generally comprises fresh, homogenized milk from which about 60% of the water has been removed, that has been chilled, fortified with additives such as vitamins and stabilizers, packaged, and finally sterilized. According to another particular embodiment of this invention, the dairy product comprises a dry creamer and Rebaudioside X or a Rebaudioside X sweetener composition.

In another particular embodiment, the dairy product provided herein comprises butter. Butter generally is made by churning fresh or fermented cream or milk. Butter generally comprises butterfat surrounding small droplets comprising mostly water and milk proteins. The churning process damages the membranes surrounding the microscopic globules of butterfat, allowing the milk fats to conjoin and to separate from the other parts of the cream. In yet another particular embodiment, the dairy product comprises buttermilk, which is the sour-tasting liquid remaining after producing butter from full-cream milk by the churning process.

In still another particular embodiment, the dairy product comprises cheese, a solid foodstuff produced by curdling milk using a combination of rennet or rennet substitutes and acidification. Rennet, a natural complex of enzymes produced in mammalian stomachs to digest milk, is used in cheese-making to curdle the milk, causing it to separate into solids known as curds and liquids known as whey. Generally, rennet is obtained from the stomachs of young ruminants, such as calves; however, alternative sources of rennet include some plants, microbial organisms, and genetically modified bacteria, fungus, or yeast. In addition, milk may be coagulated by adding acid, such as citric acid. Generally, a combination of rennet and/or acidification is used to curdle the milk. After separating the milk into curds and whey, some cheeses are made by simply draining, salting, and packaging the curds. For most cheeses, however, more processing is needed. Many different methods may be used to produce the hundreds of available varieties of cheese. Processing methods include heating the cheese, cutting it into small cubes to drain, salting, stretching, cheddaring, washing, molding, aging, and ripening. Some cheeses, such as the blue cheeses, have additional bacteria or molds introduced to them before or during aging, imparting flavor and aroma to the finished product. Cottage cheese is a cheese curd product with a mild flavor that is drained but not pressed so that some whey remains. The curd is usually washed to remove acidity. Cream cheese is a soft, mild-tasting, white cheese with a high fat content that is produced by adding cream to milk and then curdling to form a rich curd. Alternatively, cream cheese can be made from skim milk with cream added to the curd. It should be understood that cheese, as used herein, comprises all solid foodstuff produced by the curdling milk.

In another particular embodiment of this invention, the dairy product comprises yogurt. Yogurt generally is produced by the bacterial fermentation of milk. The fermentation of lactose produces lactic acid, which acts on proteins in milk to give the yogurt a gel-like texture and tartness. In particularly desirable embodiments, the yogurt may be sweetened with a sweetener and/or flavored. Non-limiting examples of flavorings include, but are not limited to, fruits (e.g., peach, strawberry, banana), vanilla, and chocolate. Yogurt, as used herein, also includes yogurt varieties with different consistencies and viscosities, such as dahi, dadih or dadiah, labneh or labaneh, bulgarian, kefir, and matsoni. In another particular embodiment, the dairy product comprises a yogurt-based beverage, also known as drinkable yogurt or a yogurt smoothie. In particularly desirable embodiments, the yogurt-based beverage may comprise sweeteners, flavorings, other ingredients, or combinations thereof.

Other dairy products beyond those described herein may be used in particular embodiments of this invention. Such dairy products are well known to those of ordinary skill in the art, non-limiting examples of which include milk, milk and juice, coffee, tea, vla, piima, filmjolk, kajmak, kephir, viili, kumiss, airag, ice milk, casein, ayran, lassi, and khoa.

According to particular embodiments of this invention, the dairy compositions also may comprise other additives. Non-limiting examples of suitable additives include sweeteners and flavorants such as chocolate, strawberry, and banana. Particular embodiments of the dairy compositions provided herein also may comprise additional nutritional supplements such as vitamins (e.g., vitamin D) and minerals (e.g., calcium) to improve the nutritional composition of the milk.

In a particularly desirable embodiment, the dairy composition comprises Rebaudioside X or a sweetener composition comprising Rebaudioside X in combination with a dairy product. In a particular embodiment, Rebaudioside X is present in the dairy composition in an amount in the range of about 200 to about 20,000 weight percent of the dairy composition.

Rebaudioside X or sweetener compositions comprising Rebaudioside X are also suitable for use in processed agricultural products, livestock products or seafood; processed meat products such as sausage and the like; retort food products, pickles, preserves boiled in soy sauce, delicacies, side dishes; soups; snacks such as potato chips, cookies, or the like; as shredded filler, leaf, stem, stalk, homogenized leaf cured and animal feed.

Methods for Preparing Sweetener Compositions and Sweetened Compositions

Sweetener Compositions

In one embodiment, a method for preparing a sweetener composition comprises combining Rebaudioside X with one or more additional sweetener, additive, functional ingredients or combinations thereof.

In a particular embodiment, a method for preparing a sweetener composition comprises combining amorphous Rebaudioside X with one or more additional sweetener, additive, functional ingredient or combination thereof.

In another embodiment, a method for preparing a sweetener composition comprises combining a Rebaudioside X complex with one or more additional sweetener, additive, functional ingredient or combination thereof.

Any of the sweeteners, additives and functional ingredients described herein can be used in the sweetener compositions of the present invention.

Sweetened Compositions

In one embodiment, the invention provides a method for preparing a sweetened composition comprising combining a sweetenable composition with amorphous Rebaudioside X or a sweetener composition comprising amorphous Rebaudioside X In another embodiment, the invention provides a method for preparing a sweetened composition comprising combining a sweetenable composition with a Rebaudioside X complex or a sweetener compositing comprising a Rebaudioside X complex.

The sweetenable composition can be any sweetenable composition described herein, including, for example, pharmaceutical compositions, edible gel mixes and compositions, dental compositions, foodstuffs (confections, condiments, chewing gum, cereal compositions, baked goods, dairy products, beverages and beverage products. In a particular embodiment, the sweetenable composition is an unsweetened beverage. In another particular embodiment, the sweetenable composition is a sweetened beverage.

Beverage and Beverage Products

In one embodiment, the invention provides a method for preparing a beverage or beverage product comprising combining a unsweetened beverage with amorphous Rebaudioside X or a sweetener composition comprising amorphous Rebaudioside X.

In another embodiment, the invention provides a method for preparing a beverage or beverage product comprising combining a unsweetened beverage with a Rebaudioside X complex or a sweetener composition comprising a Rebaudioside complex. As used herein, the term "unsweetened beverage" refers to a beverage that does not contain a sweetener component.

In one embodiment, the invention provides a method for preparing a beverage or beverage product comprising combining a sweetened beverage with amorphous Rebaudioside X or a sweetener compositions comprising amorphous Rebaudioside X.

In another embodiment, the invention provides a method for preparing a beverage or beverage product comprising combining a sweetened beverage with a Rebaudioside X complex or a sweetener composition comprising a Rebaudioside X complex.

As used herein, the term "sweetened beverage" refers to a beverage that contains one or more non-Rebaudioside X sweeteners, including natural or synthetic sweeteners.

As used herein, a "beverage or beverage product" is a ready-to-drink beverage, a beverage concentrate, a beverage syrup, or a powdered beverage. Suitable ready-to-drink beverages include carbonated and non-carbonated beverages. Carbonated beverages include, but are not limited to, cola, lemon-lime flavored sparkling beverage, orange flavored sparkling beverage, grape flavored sparkling beverage, strawberry flavored sparkling beverage, pineapple flavored sparkling beverage, ginger-ale, soft drinks and root beer. Non-carbonated beverages include, but are not limited to fruit juice, fruit-flavored juice, juice drinks, nectars, vegetable juice, vegetable-flavored juice, sports drinks, energy drinks, enhanced water with vitamins, near water drinks (e.g., water with natural or synthetic flavorants), coconut water, tea type (e.g. black tea, green tea, red tea, oolong tea), coffee, cocoa drink, beverage containing milk components (e.g. milk beverages, coffee containing milk components, café au lait, milk tea, fruit milk beverages), beverages containing cereal extracts, smoothies and combinations thereof.

Beverage concentrates and beverage syrups are prepared with an initial volume of liquid matrix (e.g. water) and the desired beverage ingredients. Full strength beverages are then prepared by adding further volumes of water. Powdered beverages are prepared by dry-mixing all of the beverage ingredients in the absence of a liquid matrix. Full strength beverages are then prepared by adding the full volume of water.

Beverages contain a liquid matrix, i.e. the basic ingredient in which the ingredients—including the sweetener or sweetener compositions—are dissolved. In one embodiment, the liquid matrix is water of beverage quality, such as, for example deionized water, distilled water, reverse osmosis water, carbon-treated water, purified water, demineralized water and combinations thereof, can be used. Additional suitable liquid matrices include, but are not limited to phosphoric acid, phosphate buffer, citric acid, citrate buffer and carbon-treated water.

In one embodiment, amorphous Rebaudioside X is provided as the sole sweetener in the beverage.

In another embodiment, a beverage comprises a sweetener composition comprising amorphous Rebaudioside X.

In still another embodiment, a beverage comprises a Rebaudioside X complex. In yet another embodiment, a beverage comprises a sweetener composition comprising a Rebaudioside X complex. The Rebaudioside X complex may comprise Rebaudioside X and at least one polyol, for example erythritol. In another embodiment, the Rebaudioside X complex comprises Rebaudioside X and maltodextrin. In still another embodiment, the Rebaudioside X complex comprises Rebaudioside X and at least one cyclodextrin.

Any sweetener composition comprising Rebaudioside X detailed herein can be used to prepare the beverages. The sweetener composition can further include at least one additional sweetener. Any of the sweeteners detailed herein can be used, including natural, non-natural, or synthetic sweeteners.

Carbohydrate sweeteners can be present in the beverage in a concentration from about 100 ppm to about 140,000 ppm. Synthetic sweeteners may be present in the beverage in a concentration from about 0.3 ppm to about 3,500 ppm. Natural high potency sweeteners may be preset in the beverage in a concentration from about 0.1 ppm to about 3,000 ppm.

The sweetener composition can further include additives including, but are not limited to, carbohydrates, polyols, amino acids and their corresponding salts, poly-amino acids and their corresponding salts, sugar acids and their corresponding salts, nucleotides, organic acids, inorganic acids, organic salts including organic acid salts and organic base salts, inorganic salts, bitter compounds, caffeine, flavorants and flavoring ingredients, astringent compounds, proteins or protein hydrolysates, surfactants, emulsifiers, weighing agents, juice, dairy, cereal and other plant extracts, flavonoids, alcohols, polymers and combinations thereof. Any suitable additive described herein can be used.

In one embodiment, the polyol can be present in the beverage in a concentration from about 100 ppm to about 250,000 ppm, such as, for example, from about 5,000 ppm to about 40,000 ppm.

In another embodiment, the amino acid can be present in the beverage in a concentration from about 10 ppm to about 50,000 ppm, such as, for example, from about 1,000 ppm to about 10,000 ppm, from about 2,500 ppm to about 5,000 ppm or from about 250 ppm to about 7,500 ppm.

In still another embodiment, the nucleotide can be present in the beverage in a concentration from about 5 ppm to about 1,000 ppm.

In yet another embodiment, the organic acid additive can be present in the beverage in a concentration from about 10 ppm to about 5,000 ppm.

In yet another embodiment, the inorganic acid additive can be present in the beverage in a concentration from about 25 ppm to about 25,000 ppm.

In still another embodiment, the bitter compound can be present in the beverage in a concentration from about 25 ppm to about 25,000 ppm.

In yet another embodiment, the flavorant can be present in the beverage a concentration from about 0.1 ppm to about 3,000 ppm.

In a still further embodiment, the polymer can be present in the beverage in a concentration from about 30 ppm to about 2,000 ppm.

In another embodiment, the protein hydrosylate can be present in the beverage in a concentration from about 200 ppm to about 50,000.

In yet another embodiment, the surfactant additive can be present in the beverage in a concentration from about 30 ppm to about 2,000 ppm.

In still another embodiment, the flavonoid additive can be present in the beverage a concentration from about 0.1 ppm to about 1,000 ppm.

In yet another embodiment, the alcohol additive can be present in the beverage in a concentration from about 625 ppm to about 10,000 ppm.

In a still further embodiment, the astringent additive can be present in the beverage in a concentration from about 10 ppm to about 5,000 ppm.

The sweetener composition can further contain one or more functional ingredients, detailed above. Functional ingredients include, but are not limited to, vitamins, minerals, antioxidants, preservatives, glucosamine, polyphenols and combinations thereof. Any suitable functional ingredient described herein can be used.

In one embodiment, a beverage comprises Rebaudioside X in an amount ranging from about 1 ppm to about 10,000 ppm, such as, for example, from about 25 ppm to about 800 ppm. In another embodiment, Rebaudioside X is present in a beverage in an amount ranging from about 100 ppm to about 600 ppm. In yet other embodiments, Rebaudioside X is present in a beverage in an amount ranging from about 100 to about 200 ppm, from about 100 ppm to about 300 ppm, from about 100 ppm to about 400 ppm, or from about 100 ppm to about 500 ppm. In still another embodiment, Rebaudioside X is present in a beverage in an amount ranging from about 300 to about 700 ppm, such as, for example, from about 400 ppm to about 600 ppm. In a particular embodiment, Rebaudioside X is present in an amount of about 500 ppm.

In another embodiment, a beverage comprises a sweetener composition containing Rebaudioside X, wherein Rebaudioside X is present in the beverage in an amount ranging from about 1 ppm to about 10,000 ppm, such as, for example, from about 25 ppm to about 800 ppm. In another embodiment, Rebaudioside X is present in the beverage in an amount ranging from about 100 ppm to about 600 ppm. In yet other embodiments, Rebaudioside X is present in the beverage in an amount ranging from about 100 to about 200 ppm, from about 100 ppm to about 300 ppm, from about 100 ppm to about 400 ppm, or from about 100 ppm to about 500 ppm. In still another embodiment, Rebaudioside X is present in the beverage in an amount ranging from about 300 to about 700 ppm, such as, for example, from about 400 ppm to about 600 ppm. In a particular embodiment, Rebaudioside X is present in the beverage in an amount of about 500 ppm.

It is contemplated that the pH of the sweetened composition, such as, for example, a beverage, does not materially or adversely affect the taste of the sweetener. A non-limiting example of the pH range of the sweetenable composition may be from about 1.8 to about 10. A further example includes a pH range from about 2 to about 5. In a particular embodiment, the pH of beverage can be from about 2.5 to about 4.2. On of skill in the art will understand that the pH of the beverage can vary based on the type of beverage. Dairy beverages, for example, can have pHs greater than 4.2.

The titratable acidity of a beverage comprising Rebaudioside X may, for example, range from about 0.01 to about 1.0% by weight of beverage.

In one embodiment, the sparkling beverage product has an acidity from about 0.01 to about 1.0% by weight of the beverage, such as, for example, from about 0.05% to about 0.25% by weight of beverage.

The carbonation of a sparkling beverage product has 0 to about 2% (w/w) of carbon dioxide or its equivalent, for example, from about 0.1 to about 1.0% (w/w).

The temperature of a beverage comprising Rebaudioside X may, for example, range from about 4° C. to about 100° C., such as, for example, from about 4° C. to about 25° C.

The beverage can be a full-calorie beverage that has up to about 120 calories per 8 oz serving.

The beverage can be a mid-calorie beverage that has up to about 60 calories per 8 oz serving.

The beverage can be a low-calorie beverage that has up to about 40 calories per 8 oz serving.

The beverage can be a zero-calorie that has less than about 5 calories per 8 oz. serving.

In one embodiment, a beverage comprises between about 200 ppm and about 500 ppm Rebaudioside X, wherein the liquid matrix of the beverage is selected from the group consisting of water, phosphoric acid, phosphate buffer, citric acid, citrate buffer, carbon-treated water and combinations thereof. The pH of the beverage can be from about 2.5 to about 4.2. The beverage can further include additives, such as, for example, erythritol. The beverage can further include functional ingredients, such as vitamins.

In particular embodiments, a method for preparing a beverage comprises combining an unsweetened or sweetened beverage with amorphous Rebaudioside X; a polyol selected from erythritol, maltitol, mannitol, xylitol, glycerol, sorbitol, and combinations thereof and optionally at least one additional sweetener and/or functional ingredient. In a particular embodiment, the polyol is erythritol. In one embodiment, amorphous Rebaudioside X and the polyol are present in the beverage in a weight ratio from about 1:1 to about 1:800, such as, for example, from about 1:4 to about 1:800, from about 1:20 to about 1:600, from about 1:50 to about 1:300 or from about 1:75 to about 1:150. In another embodiment, Rebaudioside X is present in the beverage in a concentration from about 1 ppm to about 10,000 ppm, such as, for example, about 500 ppm. The polyol, such as, for example, erythritol, is present in the beverage in a concentration from about 100 ppm to about 250,000 ppm, such as, for example, from about 5,000 ppm to about 40,000 ppm, from about 1,000 ppm to about 35,000 ppm.

In particular embodiments, a method for preparing a beverage comprises combining an unsweetened or sweetened beverage with amorphous Rebaudioside X; a carbohydrate sweetener selected from sucrose, fructose, glucose, maltose and combinations thereof and optionally at least one additional sweetener and/or functional ingredient. In one embodiment, amorphous Rebaudioside X and the carbohydrate are present in a sweetener composition in a weight ratio from about 0.001:14 to about 1:0.01, such as, for example, about 0.06:6. In one embodiment, Rebaudioside X is present in the beverage in a concentration from about 1 ppm to about 10,000 ppm, such as, for example, about 500 ppm. The carbohydrate, such as, for example, sucrose, is present in the beverage a concentration from about 100 ppm to about 140,000 ppm, such as, for example, from about 1,000 ppm to about 100,000 ppm, from about 5,000 ppm to about 80,000 ppm.

In particular embodiments, a method for preparing a beverage comprises combining an unsweetened or sweetened beverage with amorphous Rebaudioside X; an amino acid selected from glycine, alanine, proline, taurine and combinations thereof; and optionally at least one additional sweetener and/or functional ingredient. In one embodiment, Rebaudioside X is present in the beverage in a concentration from about 1 ppm to about 10,000 ppm, such as, for example, about 500 ppm. The amino acid, such as, for example, glycine, can be present in the beverage in a concentration from about 10 ppm to about 50,000 ppm when present in a sweetened composition, such as, for example, from about 1,000 ppm to about 10,000 ppm, from about 2,500 ppm to about 5,000 ppm In particular embodiments, a method for preparing a beverage comprises combining an unsweetened or sweetened beverage with amorphous Rebaudioside X; a salt selected from sodium chloride, magnesium chloride, potassium chloride, calcium chloride, phosphate salts and combinations thereof; and optionally at least one additional sweetener and/or functional ingredient. In one embodiment, Rebaudioside X is present in the beverage in a concentration from about 1 ppm to about 10,000 ppm, such as, for example, about 500 ppm. The inorganic salt, such as, for example, magnesium chloride, is present in the beverage in a concentration from about 25 ppm to about 25,000 ppm, such as, for example, from about 100 ppm to about 4,000 ppm or from about 100 ppm to about 3,000 ppm.

In another embodiment, a method for preparing a beverage comprises combining an unsweetened or sweetened beverage with a Rebaudioside X complex. In one embodiment, the Rebaudioside X complex comprises Rebaudioside X and at least one polyol, for example erythritol. In another embodiment, the Rebaudioside X complex comprises Rebaudioside X and maltodextrin. In still another embodiment, the Rebaudioside X complex comprises Rebaudioside X and at least one cyclodextrin. The beverage can optionally contain other sweeteners, additives and/or functional ingredients. In one embodiment, a Rebaudioside X complex is present in a beverage in a concentration from about 1 ppm to about 10,000 pp.

Improving Temporal and/or Flavor Profile

A method for imparting a more sugar-like temporal profile, flavor profile, or both to a sweetenable composition comprises combining a sweetenable composition with amorphous Rebaudioside X or the sweetener compositions of the present invention, i.e., sweetener compositions containing amorphous Rebaudioside X. The Rebaudioside X is in dry powdered form. In a particular embodiment, the sweetenable composition is an unsweetened beverage.

The sweetener compositions include the addition of other sweeteners, additives, functional ingredients and combinations thereof. Any sweetener, additive or functional ingredient detailed herein can be used.

As used herein, the "sugar-like" characteristics include any characteristic similar to that of sucrose and include, but are not limited to, maximal response, flavor profile, temporal profile, adaptation behavior, mouthfeel, concentration/response function, tastant/and flavor/sweet taste interactions, spatial pattern selectivity, and temperature effects.

The flavor profile of a sweetener is a quantitative profile of the relative intensities of all of the taste attributes exhibited. Such profiles often are plotted as histograms or radar plots.

These characteristics are dimensions in which the taste of sucrose is different from the tastes of Rebaudioside X. Of these, however, the flavor profile and temporal profile are particularly important. In a single tasting of a sweet food or beverage, differences (1) in the attributes that constitute a sweetener's flavor profile and (2) in the rates of sweetness onset and dissipation, which constitute a sweetener's temporal profile, between those observed for sucrose and for Rebaudioside X can be noted.

Whether or not a characteristic is more sugar-like is determined by an expert sensory panel who taste compositions comprising sugar and compositions comprising Rebaudioside X, both with and without additives, and provide their impression as to the similarities of the characteristics of the sweetener compositions, both with and without additives, with those comprising sugar. A suitable procedure for determining whether a composition has a more sugar-like taste is described in embodiments described herein below.

In a particular embodiment, a panel of assessors is used to measure the reduction of sweetness linger. Briefly described, a panel of assessors (generally 8 to 12 individuals) is trained to evaluate sweetness perception and measure sweetness at several time points from when the sample is initially taken into the mouth until 3 minutes after it has been expectorated. Using statistical analysis, the results are compared between samples containing additives and samples that do not contain additives. A decrease in score for a time point measured after the sample has cleared the mouth indicates there has been a reduction in sweetness perception.

The panel of assessors may be trained using procedures well known to those of ordinary skill in the art. In a particular embodiment, the panel of assessors may be trained using the Spectrum™ Descriptive Analysis Method (Meilgaard et al, *Sensory Evaluation Techniques*, 3$^{rd}$ edition, Chapter 11). Desirably, the focus of training should be the recognition of and the measure of the basic tastes; specifically, sweet. In order to ensure accuracy and reproducibility of results, each assessor should repeat the measure of the reduction of sweetness linger about three to about five times per sample, taking at least a five minute break between each repetition and/or sample and rinsing well with water to clear the mouth.

Generally, the method of measuring sweetness comprises taking a 10 mL sample into the mouth, holding the sample in the mouth for 5 seconds and gently swirling the sample in the mouth, rating the sweetness intensity perceived at 5 seconds, expectorating the sample (without swallowing following expectorating the sample), rinsing with one mouthful of water (e.g., vigorously moving water in mouth as if with mouth wash) and expectorating the rinse water, rating the sweetness intensity perceived immediately upon expectorating the rinse water, waiting 45 seconds and, while waiting those 45 seconds, identifying the time of maximum perceived sweetness intensity and rating the sweetness intensity at that time (moving the mouth normally and swallowing as needed), rating the sweetness intensity after another 10 seconds, rating the sweetness intensity after another 60 seconds (cumulative 120 seconds after rinse), and rating the sweetness intensity after still another 60 seconds (cumulative 180 seconds after rinse). Between samples take a 5 minute break, rinsing well with water to clear the mouth.

EXAMPLES

Instrumentation
Inel XRG-3000 Diffractometer

XRPD patterns were collected with an Inel XRG-3000 diffractometer. An incident beam of Cu-Kα radiation was produced using a fine-focus tube and a parabolically graded multilayer mirror. Prior to the analysis, a silicon specimen (NIST SRM 640d) was analyzed to verify the observed position of the Si 111 peak is consistent with the NIST-certified position. A specimen of the sample was packed into a thin-walled glass capillary and a beam-stop was used to minimize the background from air. Diffraction patterns were collected in transmission geometry using Windif v. 6.6 software and a curved position-sensitive Equinox detector with a 2θ range of 120°. The data acquisition parameters for each pattern are displayed 2.5-40° 2θ.

PANalytical X'Pert PRO Diffractometer

High resolution XRPD patterns were collected with a PANalytical X'Pert PRO MPD diffractometer using an incident beam of Cu radiation produced using an Optix long, fine-focus source. An elliptically graded multilayer mirror was used to focus Cu Kα X-rays through the specimen and onto the detector. Prior to the analysis, a silicon specimen (NIST SRM 640d) was analyzed to verify the observed position of the Si 111 peak is consistent with the NIST-certified position. A specimen of the sample was sandwiched between 3-μm-thick films and analyzed in transmission geometry. A beam-stop, short antiscatter extension and anti-scatter knife edge were used to minimize the background generated by air. Soller slits for the incident and diffracted beams were used to minimize broadening from axial divergence. Diffraction patterns were collected using a scanning position-sensitive detector (X'Celerator) located 240 mm from the specimen and Data Collector software v. 2.2b.

Example 1

Purification of Reb X from *Stevia rebaudiana* Bertoni Plant Leaves

Two kg of *Stevia rebaudiana* Bertoni plant leaves were dried at 45° C. to an 8.0% moisture content and ground to 10-20 mm particles. The content of different glycosides in the leaves was as follows: Stevioside—2.55%, Reb A—7.78%, Reb B—0.01%, Reb C—1.04%, Reb D—0.21%, Reb F—0.14%, Reb X—0.10% Dulcoside A—0.05%, and Steviolbioside—0.05%. The dried material was loaded into a continuous extractor and the extraction was carried out with 40.0 L of water at a pH of 6.5 at 40° C. for 160 min. The filtrate was collected and subjected to chemical treatment. Calcium oxide in the amount of 400 g was added to the filtrate to adjust the pH within the range of 8.5-9.0, and the mixture was maintained for 15 min with slow agitation. Then, the pH was adjusted to around 3.0 by adding 600 g of $FeCl_3$ and the mixture was maintained for 15 min with slow agitation. A small amount of calcium oxide was further added to adjust the pH to 8.5-9.0 and the mixture was maintained for 30 min with slow agitation. The precipitate was removed by filtration on a plate-and-frame filter press using cotton cloth as the filtration material. The slightly yellow filtrate was passed through the column, packed with cation-exchange resin Amberlite FCP22 ($H^+$) and then, through the column with anion-exchange resin Amberlite FPA53 ($OH^-$). The flow rate in both columns was maintained at SV=0.8 hour$^{-1}$. After completion both columns were washed with RO water to recover the steviol glycosides left in the columns and the filtrates were combined. The portion of combined solution containing 120 g total steviol glycosides was passed through seven columns, wherein each column was packed with specific macroporous polymeric adsorbent YWD-03 (Cangzhou Yuanwei, China). The first column with the size of ⅓ of the others acted as a "catcher column". The SV was around 1.0 hour$^{-1}$. After all extract was passed through the columns, the resin sequentially was washed with 1 volume of water, 2 volumes of 0.5% NaOH, 1 volume of water, 2 volumes of 0.5% HCl, and finally with water until the pH was 7.0. The "catcher column" was washed separately.

Desorption of the adsorbed steviol glycosides was carried out with 52% ethanol at SV=1.0 hour$^{-1}$. Desorption of the first "catcher column" was carried out separately and the filtrate was not mixed with the main solution obtained from other columns. Desorption of the last column also was carried out separately. The quality of extract from different columns with specific macroporous adsorbent is shown in Table 3.

TABLE 3

| Steviol Glycoside Content | |
|---|---|
| Column | Total steviol glycosides, % |
| 1 (catcher) | 55.3 |
| 2 | 92.7 |
| 3 | 94.3 |

TABLE 3-continued

Steviol Glycoside Content

| Column | Total steviol glycosides, % |
|---|---|
| 4 | 96.1 |
| 5 | 96.3 |
| 6 | 95.8 |
| 7 | 80.2 |

The total steviol glycoside content can be determined experimentally by HPLC or HPLC/MS. For example, chromatographic analysis can be performed on a HPLC/MS system comprising an Agilent 1200 series (USA) liquid chromatograph equipped with binary pump, autosampler, thermostatted column compartment, UV detector (210 nm), and Agilent 6110 quadrupole MS detector interfaced with Chemstation data acquisition software. The column can be a "Phenomenex Prodigy 5u ODS3 250×4.6 mm; 5 μm (P/No. 00G-4097-E0)" column maintained at 40° C. The mobile phase can be 30:70 (vol/vol.) acetonitrile and water (containing 0.1% formic acid) and the flow rate through the column can be 0.5 mL/min. The steviol glycosides can be identified by their retention times in such a method, which are generally around 2.5 minutes for Reb D, around 2.9 minutes for Reb X, 5.5 minutes for Reb A, 5.8 minutes for Stevioside, 7.1 minutes for Reb F, 7.8 minutes for Reb C, 8.5 minutes for Dulcoside A, 11.0 minutes for Rubusoside, 15.4 minutes for Reb B and 16.4 minutes for Steviolbioside. One of skill in the art will appreciate that the retention times for the various steviol glycosides given above can vary with changes in solvent and/or equipment.

Eluates from second to sixth columns were combined and treated separately. The combined solution of steviol glycosides was mixed with 0.3% of activated carbon from the total volume of solution. The suspension was maintained at 25° C. for 30 min with continuous agitation. Separation of carbon was carried out on a press-filtration system. For additional decolorization the filtrate was passed through the columns packed with cation-exchange resin Amberlite FCP22 (H$^+$) followed with anion-exchange resin Amberlite FPA53 A30B (OH$^-$). The flow rate in both columns was around SV=0.5 hour$^{-1}$. The ethanol was distilled using a vacuum evaporator. The solids content in the final solution was around 15%. The concentrate was passed through the columns packed with cation-exchange resin Amberlite FCP22 (H$^+$) and anion-exchange resin Amberlite FPA53 (OH$^-$) with SV=0.5 hour$^{-1}$. After all the solution was passed through the columns, both resins were washed with RO water to recover the steviol glycosides left in the columns. The resulting refined extract was transferred to the nanofiltration device, concentrated to around 52% of solids content and spray dried to provide a highly purified mixture of steviol glycosides. The yield was 99.7 g. The mixture contained Stevioside—20.5%, Reb A—65.6%, Reb B—0.1%, Reb C—8.4%, Reb D—0.5%, Reb F—1.1%, Reb X—0.1%, Dulcoside A—0.4%, and Steviolbioside—0.4%.

The combined eluate from the last column, contained about 5.3 g of total steviol glycosides including 2.3 g Reb D and around 1.9 g Reb X (35.8% Reb X/TSG ratio). It was deionized and decolorized as discussed above and then concentrated to a 33.5% content of total solids.

The concentrate was mixed with two volumes of anhydrous methanol and maintained at 20-22° C. for 24 hours with intensive agitation.

The resulting precipitate was separated by filtration and washed with about two volumes of absolute methanol. The yield of Rebaudioside X was 1.5 g with around 80% purity.

For the further purification the precipitate was suspended in three volumes of 60% methanol and treated at 55° C. for 30 min, then cooled down to 20-22° C. and agitated for another 2 hours.

The resulting precipitate was separated by filtration and washed with about two volumes of absolute methanol and subjected to similar treatment with a mixture of methanol and water.

The yield of Rebaudioside X was 1.2 g with 97.3% purity.

Example 2

Structural Elucidation of Rebaudioside X

FIRMS: FIRMS (High Resolution Mass Spectrum) data was generated with a Waters Premier Quadrupole Time-of-Flight (Q-TOF) mass spectrometer equipped with an electrospray ionization source operated in the positive-ion mode. Samples were diluted and eluted with a gradient of 2:2:1 methanol:acetonitrile:water and introduced 50 μL via infusion using the onboard syringe pump NMR: The sample was dissolved in deuterated pyridine ($C_5D_5N$) and NMR spectra were acquired on Varian Unity Plus 600 MHz instruments using standard pulse sequences. The chemical shifts are given in δ (ppm), and coupling constants are reported in Hz.

The complete $^1$H and $^{13}$C NMR spectral assignments for the diterpene glycoside rebaudioside X determined on the basis of 1D ($^1$H and $^{13}$C) and 2D (COSY, HMQC and HMBC) NMR as well as high resolution mass spectroscopic data:

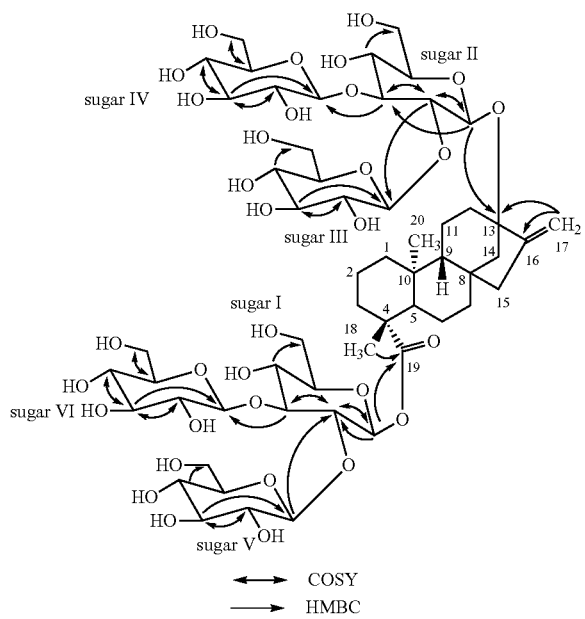

Discussion

Figure 11A:
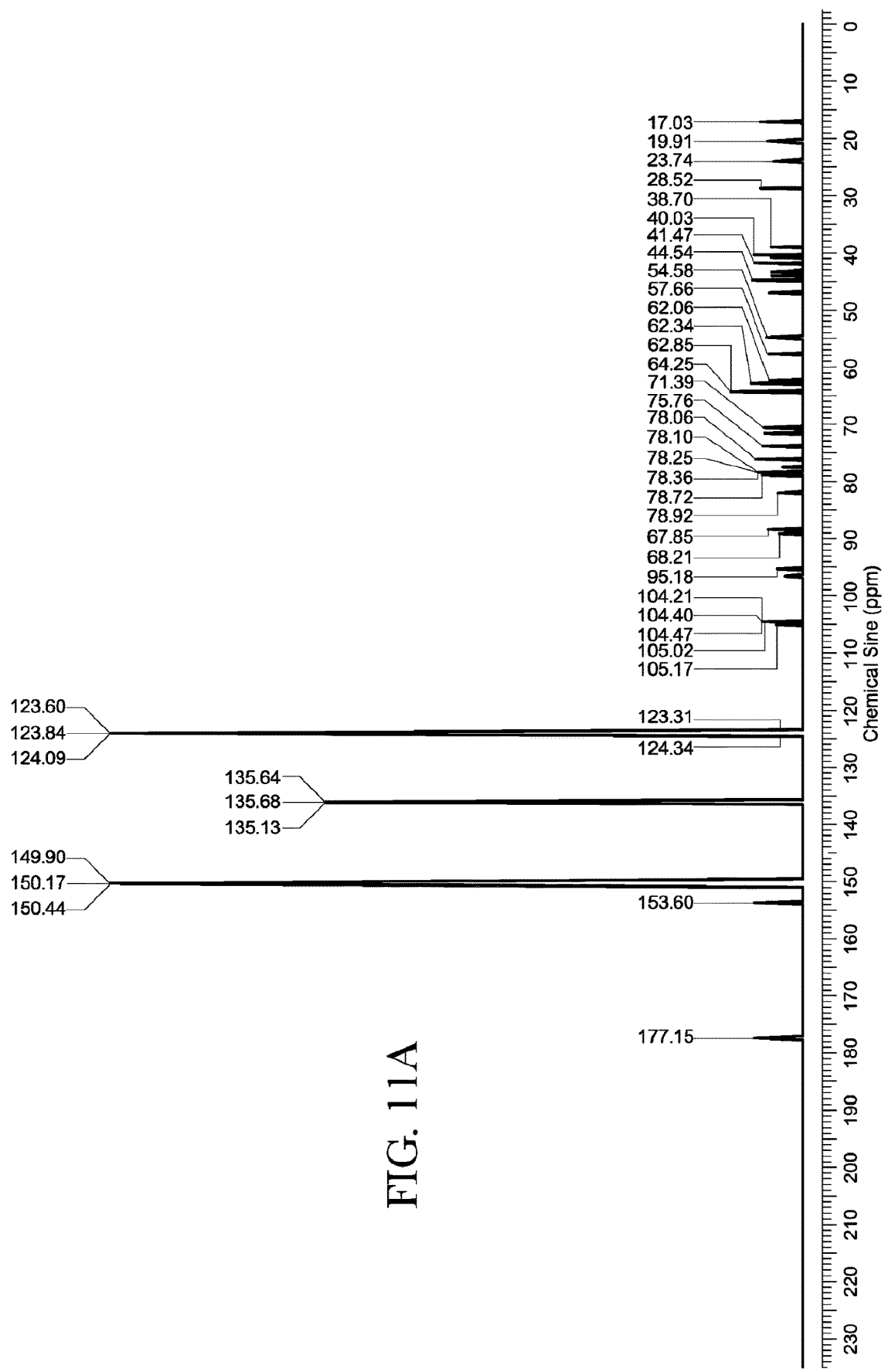
FIG. 11A: illustrates the $^{13}$C NMR spectrum of Reb X (150 MHz, $C_5D_5N$).
Figure 12A:
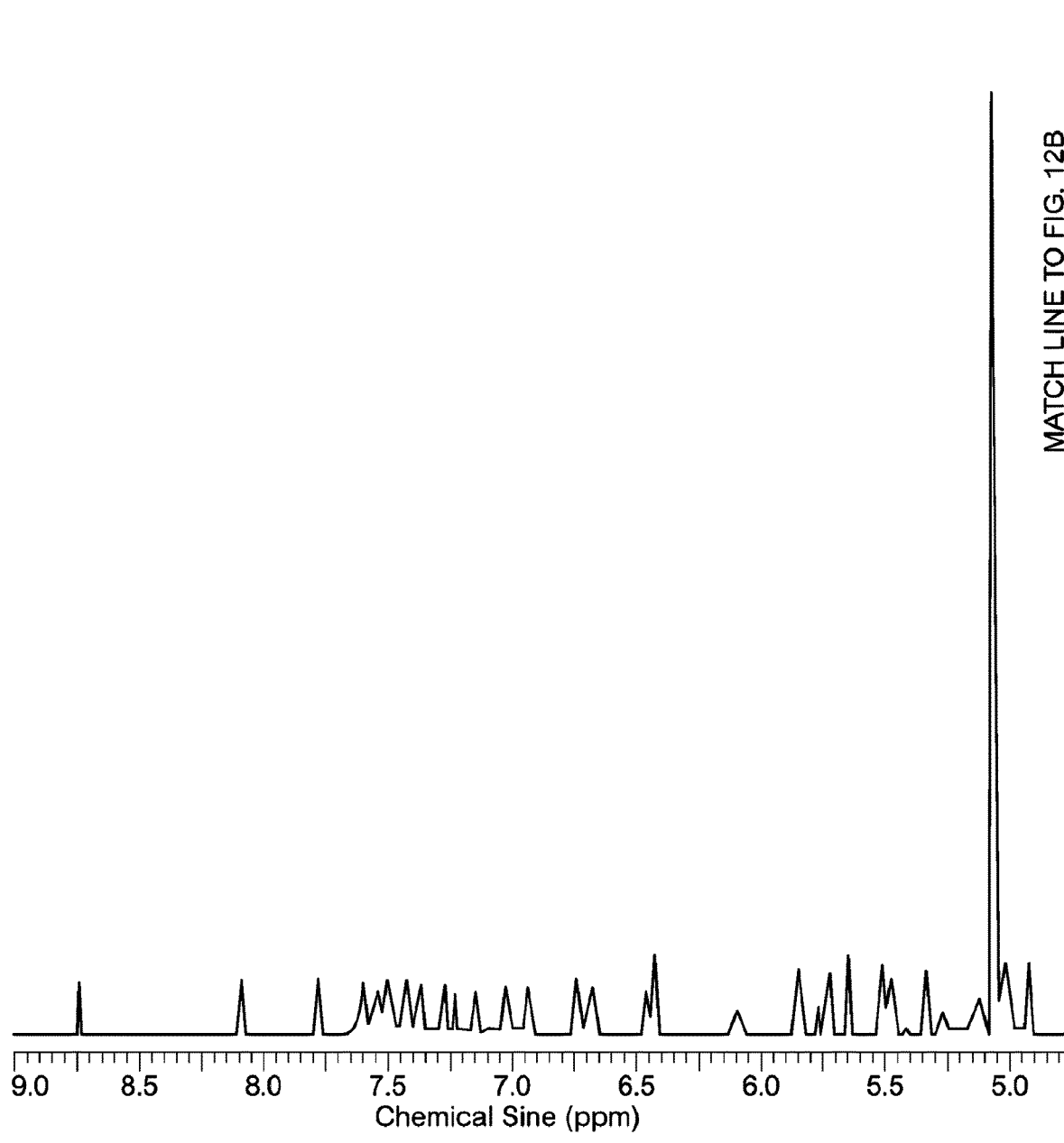
FIGS. 12A and 12B: illustrate the $^1$H NMR spectrum of Reb X (600 MHz, $C_5D_5N$).
Figure 12B:
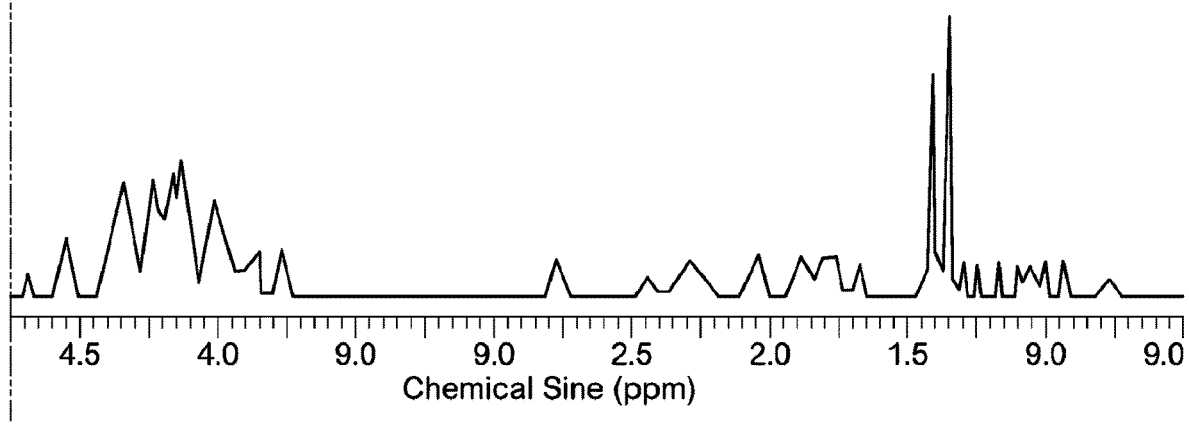

The molecular formula was deduced as $C_{56}H_{90}O_{33}$ on the basis of its positive high resolution (HR) mass spectrum which showed an [M+NH$_4^+$] ion at m/z 1308.5703 together with an [M+Na+] adduct at m/z 1313.5274. This composition was supported by $^{13}$C NMR spectral data (FIGS. 11A and 11B). The $^1$H NMR spectrum (FIGS. 12A and 12B) showed the presence of two methyl singlets at δ 1.32 and 1.38, two olefinic protons as singlets at δ 4.90 and 5.69 of an exocyclic double bond, nine methylene and two methine protons between δ 0.75-2.74 characteristic for the ent-kaurane diterpenoids isolated earlier from the genus *Stevia*.

Figure 13:
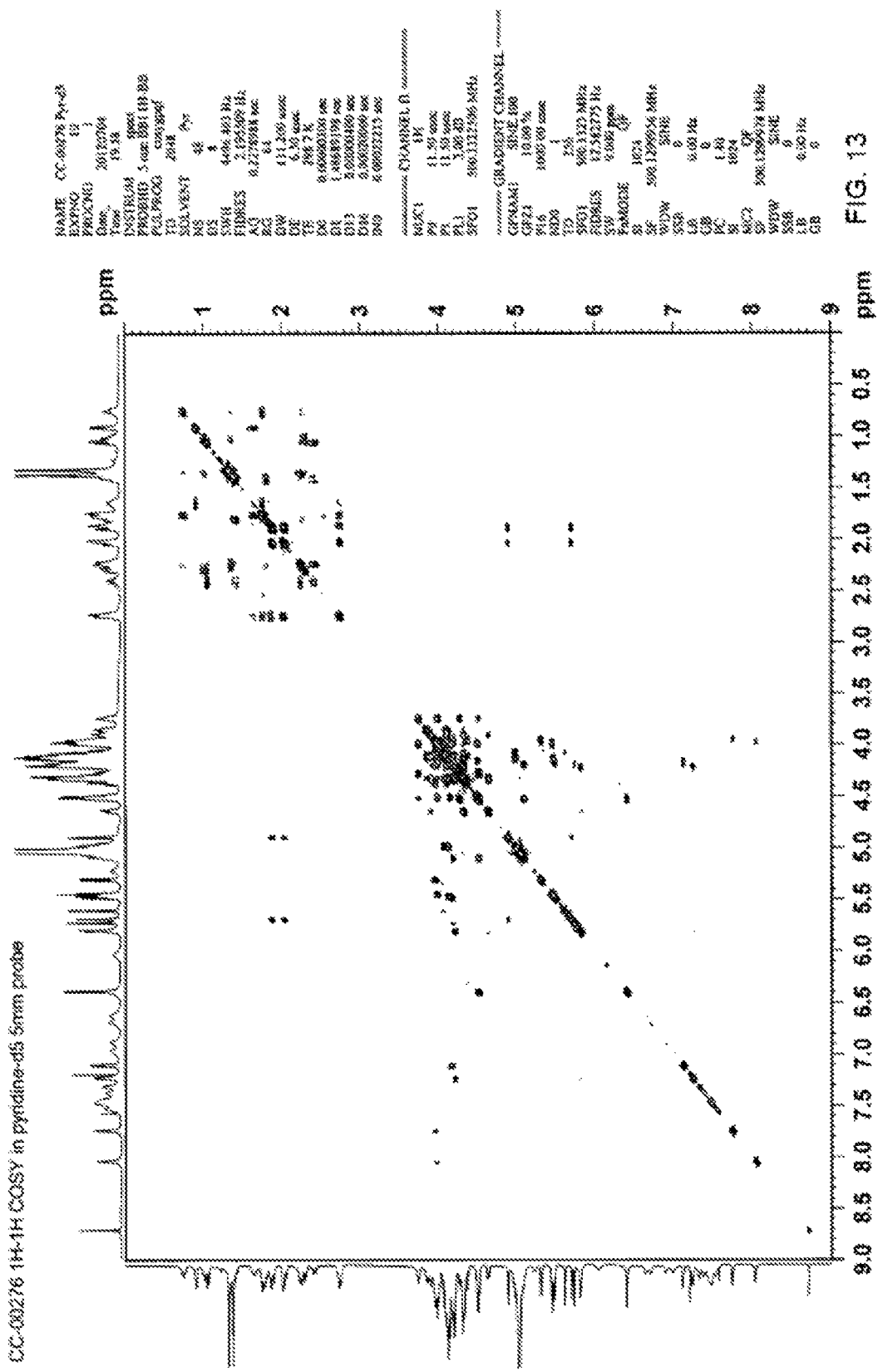
FIG. 13: illustrates the $^1$H-$^1$H COSY spectrum of Reb X (600 MHz, $C_5D_5N$).

The basic skeleton of ent-kaurane diterpenoids was supported by COSY (FIG. 13): H-1/H-2; H-2/H-3; H-5/H-6; H-6/H-7; H-9/H-11; H-11/H-12 correlations.

Figure 14:
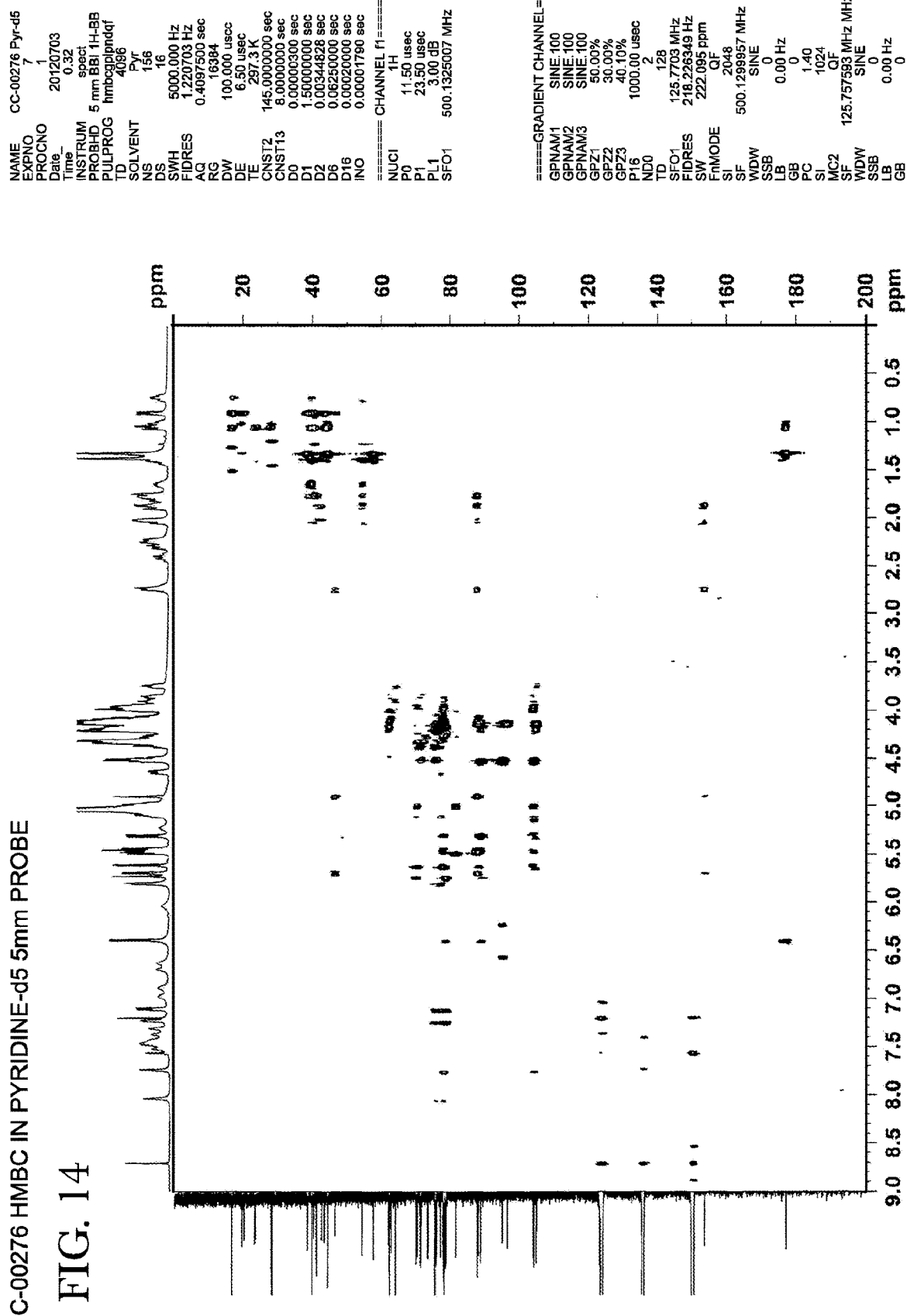
FIG. 14: illustrates the HMBC spectrum of Reb X (600 MHz, $C_5D_5N$).

The basic skeleton of ent-kaurane diterpenoids was also supported by HMBC (FIG. 14): H-1/C-2, C-10; H-3/C-1, C-2, C-4, C-5, C-18, C-19; H-5/C-4, C-6, C-7, C-9, C-10, C-18, C-19, C-20; H-9/C-8, C-10, C-11, C-12, C-14, C-15; H-14/C-8, C-9, C-13, C-15, C-16 and H-17/C-13, C-15, C-16 correlations.

The $^1$H NMR spectrum also showed the presence of anomeric protons resonating at δ 5.31, 5.45, 5.46, 5.48, 5.81, and 6.39; suggesting six sugar units in its structure. Enzymatic hydrolysis furnished an aglycone which was identified as steviol by comparison of co-TLC with standard compound. Acid hydrolysis with 5% $H_2SO_4$ afforded glucose which was identified by direct comparison with authentic samples by TLC. The $^1$H and $^{13}$C NMR values for all protons and carbons were assigned on the basis of COSY, HMQC and HMBC correlations (Table 3).

TABLE 3

$^1$H and $^{13}$C NMR spectral data for Rebaudioside X in $C_5D_5N^{a-c}$.

| Position | $^{13}$C NMR | $^1$H NMR |
|---|---|---|
| 1 | 40.3 | 0.75 t (13.2) |
|  |  | 1.76 m |
| 2 | 19.6 | 1.35 m |
|  |  | 2.24 m |
| 3 | 38.4 | 1.01 m |
|  |  | 2.30 d (13.3) |
| 4 | 44.3 | — |
| 5 | 57.4 | 1.06 d (12.8) |
| 6 | 23.5 | 2.23 m |
|  |  | 2.41 q (13.2) |
| 7 | 42.6 | 1.41 m |
|  |  | 1.80 m |
| 8 | 41.2 | — |
| 9 | 54.3 | 0.91 d (7.7) |
| 10 | 39.7 | — |
| 11 | 20.2 | 1.65 m |
|  |  | 1.75 m |
| 12 | 38.5 | 1.86 m |
|  |  | 2.73 m |
| 13 | 87.6 | — |
| 14 | 43.3 | 2.02 m |
|  |  | 2.74 m |
| 15 | 46.5 | 1.88 d (16.4) |
|  |  | 2.03 m |
| 16 | 153.3 | — |
| 17 | 104.9 | 4.90 s |
|  |  | 5.69 s |
| 18 | 28.2 | 1.32 s |
| 19 | 176.9 | — |
| 20 | 16.8 | 1.38 s |
| 1' | 94.9 | 6.39 d (8.2) |
| 2' | 76.9 | 4.51 t (8.5) |
| 3' | 88.6 | 5.09 t (8.5) |
| 4' | 70.1 | 4.18 m |
| 5' | 78.4 | 4.13 m |
| 6' | 61.8 | 4.20 m |
|  |  | 4.31 m |
| 1" | 96.2 | 5.46 d (7.1) |
| 2" | 81.4 | 4.13 m |
| 3" | 87.9 | 4.98 t (8.5) |
| 4" | 70.4 | 4.07 t (9.6) |
| 5" | 77.7 | 3.94 m |
| 6" | 62.6 | 4.19 m |
|  |  | 4.32 m |
| 1''' | 104.8 | 5.48 d (7.7) |
| 2''' | 75.8 | 4.15 m |
| 3''' | 78.6 | 4.13 m |
| 4''' | 73.2 | 3.98 m |
| 5''' | 77.6 | 3.74 ddd (2.8, 6.4, 9.9) |
| 6''' | 64.0 | 4.27 m |
|  |  | 4.51 m |
| 1'''' | 103.9 | 5.45 d (7.5) |
| 2'''' | 75.6 | 3.98 m |
| 3'''' | 77.8 | 4.50 t (7.8) |
| 4'''' | 71.3 | 4.14 m |
| 5'''' | 78.0 | 3.99 m |
| 6'''' | 62.1 | 4.20 m |
|  |  | 4.32 m |
| 1''''' | 104.2 | 5.81 d (7.2) |
| 2''''' | 75.5 | 4.20 m |
| 3''''' | 78.4 | 4.20 m |
| 4''''' | 73.6 | 4.10 m |
| 5''''' | 77.8 | 3.90 ddd (2.8, 6.4, 9.9) |
| 6''''' | 64.0 | 4.32 m |
|  |  | 4.64 d (10.3) |
| 1'''''' | 104.1 | 5.31 d (8.0) |
| 2'''''' | 75.5 | 3.95 m |
| 3'''''' | 78.0 | 4.37 t (9.1) |
| 4'''''' | 71.1 | 4.10 m |
| 5'''''' | 78.1 | 3.85 ddd (1.7, 6.1, 9.9) |
| 6'''''' | 62.1 | 4.10 m |
|  |  | 4.32 m |

[a] assignments made on the basis of COSY, HMQC and HMBC correlations;
[b] Chemical shift values are in δ (ppm);
[c] Coupling constants are in Hz.

Based on the results from NMR spectral data, it was concluded that there are six glucosyl units. A close comparison of the $^1$H and $^{13}$C NMR spectrum of Reb X with rebaudioside D suggested that Reb X was also a steviol glycoside which had three glucose residues that attached at the C-13 hydroxyl as a 2,3-branched glucotriosyl substituent and another 2,3-branched glucotriosyl moiety in the form of an ester at C-19.

The key COSY and HMBC correlations suggested the placement of the sixth glucosyl moiety at the C-3 position of Sugar I. The large coupling constants observed for the six anomeric protons of the glucose moieties at δ 5.31 (d, J=8.0 Hz), 5.45 (d, J=7.5 Hz), 5.46 (d, J=7.1 Hz), 5.48 (d, J=7.7 Hz), 5.81 (d, J=7.2 Hz), and 6.39 (d, J=8.2 Hz), suggested their β-orientation as reported for steviol glycosides. Based on the results of NMR and mass spectral studies and in comparison with the spectral values of rebaudioside A and rebaudioside D, Reb X was assigned as 13-[(2-O-β-D-glucopyranosyl-3-O-β-D-glucopyranosyl-β-D-glucopyranosyl)oxy]ent kaur-16-en-19-oic acid-[(2-O-β-D-glucopyranosyl-3-O-β-D-glucopyranosyl-β-D-glucopyranosyl) ester].

Example 3

Preparation and Characterization of Form A Rebaudioside X

X-ray amorphous Rebaudioside X was added to a 1:1 mixture of methanol and water to provide a slurry. The slurry was stirred at room temperature overnight. The X-ray diffraction pattern of the Rebaudioside X obtained is shown in FIG. 1. Form A was successfully indexed, indicating that the sample is composed primarily of a single crystalline phase. Prominent peaks are provided below:

TABLE 1

Form A Rebaudioside X Prominent XPRD

| °2Θ | d space (Å) | Intensity (%) |
|---|---|---|
| 3.76 ± 0.20 | 23.489 ± 1.319 | 67 |
| 6.50 ± 0.20 | 13.594 ± 0.431 | 58 |
| 6.62 ± 0.20 | 13.354 ± 0.416 | 89 |
| 6.79 ± 0.20 | 13.025 ± 0.395 | 100 |
| 9.93 ± 0.20 | 8.909 ± 0.183 | 36 |
| 12.33 ± 0.20 | 7.176 ± 0.118 | 40 |
| 12.45 ± 0.20 | 7.109 ± 0.116 | 49 |
| 13.69 ± 0.20 | 6.469 ± 0.095 | 44 |
| 14.06 ± 0.20 | 6.301 ± 0.090 | 50 |
| 15.44 ± 0.20 | 5.738 ± 0.075 | 37 |
| 16.25 ± 0.20 | 5.456 ± 0.068 | 46 |
| 16.80 ± 0.20 | 5.278 ± 0.063 | 66 |
| 20.44 ± 0.20 | 4.345 ± 0.042 | 48 |

Figure 2:
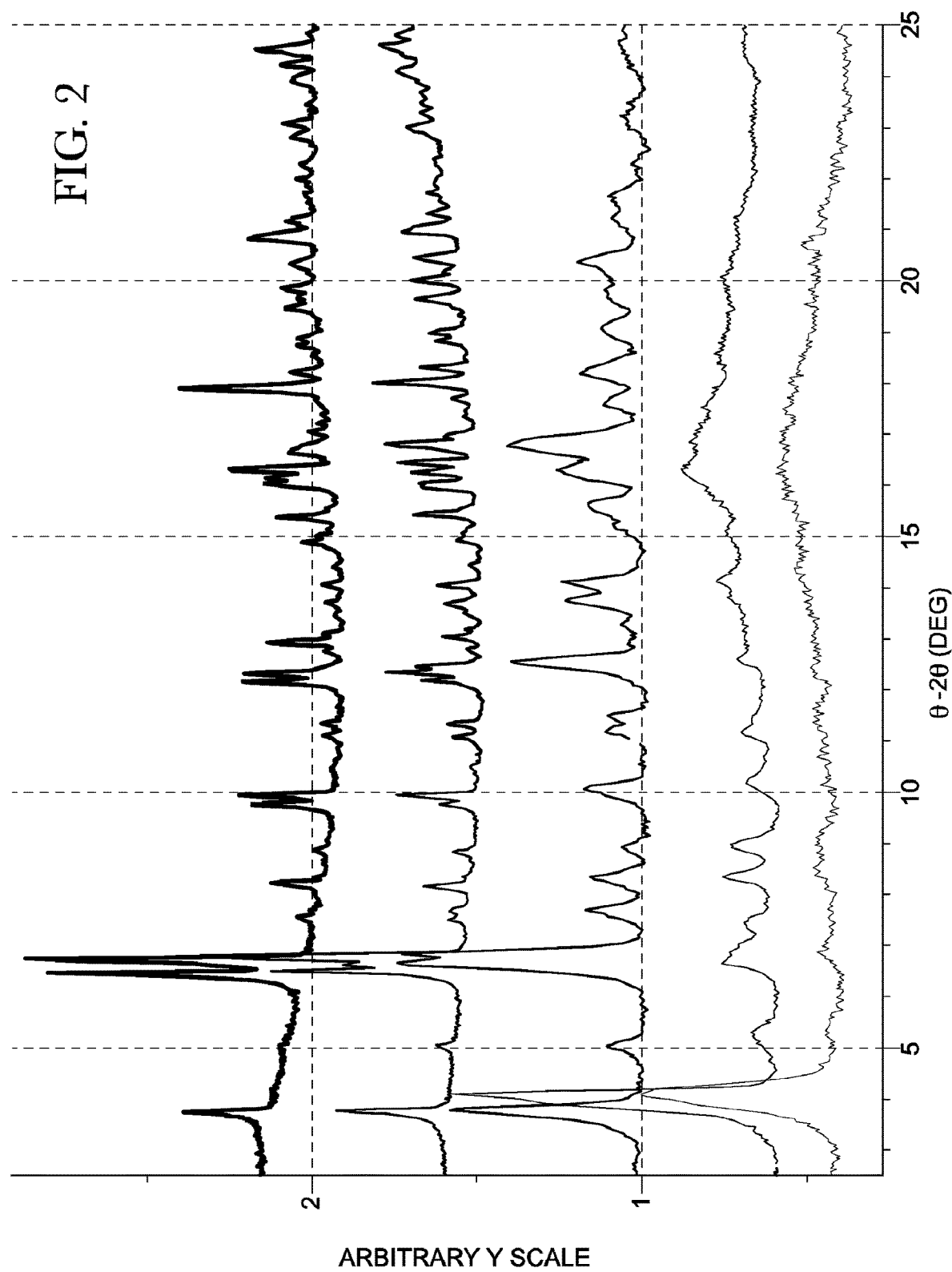
FIG. 2: illustrates the X-ray diffraction pattern of Form A Rebaudioside X collected with Cu-Kα radiation Cu-Kα radiation (the wavelength used to calculate d-spacings was 1.541874 Å, a weighted average of the Cu-$K_{\alpha 1}$ and Cu-$K_{\alpha 2}$ wavelengths). Material for the top trace was prepared via 1:1 isopropanol:water (v/v) held at ambient temperature overnight. Material for the second trace was prepared via 1:1 methanol water (v/v) held at ambient temperature overnight. Material for the third trace was prepared via water slurry at ambient temperature for 3 days. Material for the fourth trace was analyzed after isolation of Rebaudioside X from *Stevia* extract without further preparation. Material for the fifth trace was vacuum dried at ambient temperature for 2 days.

Non-systematic peak shifts between the X-ray diffraction patterns of Form A are observed (FIG. 2) and are likely due to unit cell volume differences and indicate Form A is a variable hydrate/solvate. The unit cell volume may change to accommodate varying X-ray diffraction pattern peak positions are a direct result of the unit cell parameters.

Approximate methanol content was estimated using proton NMR spectroscopy. A NMR spectrum was collected on freshly prepared wet solids isolated by centrifugation. No further drying was applied to the sample analyzed. The spectrum indicates the presence of approximately 16 moles of methanol per one mole of Rebaudioside X (~28% of the solvent).

Approximate water content was estimated by exposing Form A to ambient relative humidity and measurement by coulemetric Karl Fischer analysis using a Mettler Toledo DL239 Karl Fischer titrator with a Stromboli oven attachment. Briefly, two replicates of the sample were placed into the drying oven set at a temperature of approximately 170° C. The drying oven was purged into the titrator vessel with dry nitrogen. The samples were then titrated by means of a generator electrode, which produces iodine by electrochemical oxidation ($2I^- \rightarrow I_2 + 2e^-$). A NIST-traceable water standard (Hydranal Water Standard 10.0) was analyzed to check the operation of the coulometer.

A water content of ~11.4% was determined (average of two experiments) for Form A exposed to relative humidity (~23% RH) for three days, with is consistent with approximately 9 moles of water.

Hot stage microscopy (HSM) was performed using a Linkam hot stage (FTIR 600) mounted on a Leica DM LP microscope equipped with a SPOT Insight™ color digital camera. Temperature calibrations were performed using USP melting point standards. Samples were placed on a cover glass, and a second cover glass was placed on top of the sample. As the stage was heated, each sample was visually observed using a 20× objective with crossed polarizers and a first order red compensator. Images were captured using SPOT software (v. 4.5.9). Analysis was conducted under mineral oil and volatilization (as determined by evolution of gas) was observed at 109.4° C., which supports the observation of desolvation endotherm from DSC. Recrystallization was not observed upon cooling to ambient temperature and re-heating to over 200° C.

Figure 3:
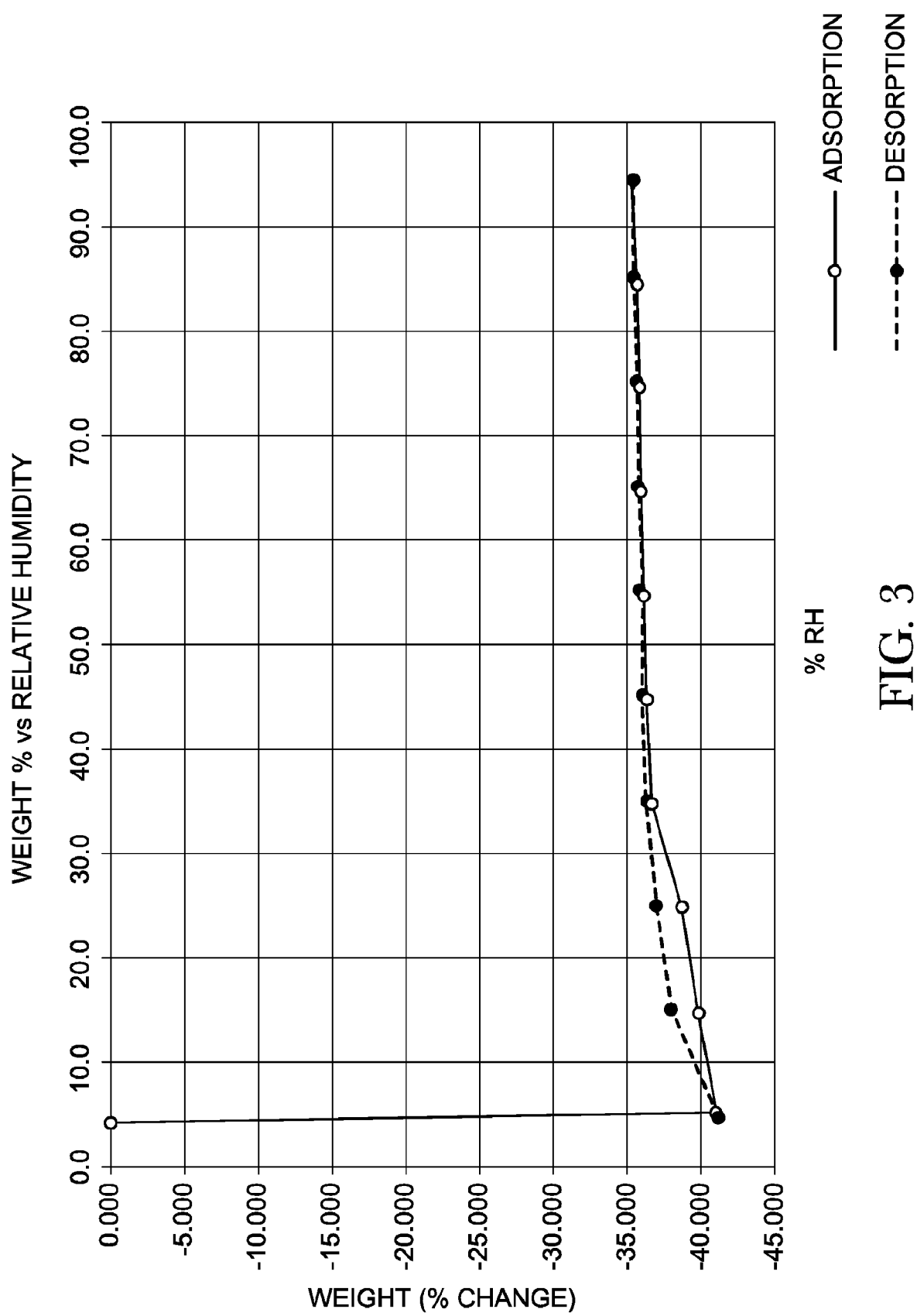
FIG. 3: illustrates the Dynamic Vapor Soprtion (DVS) isotherm of Form A Rebaudioside X.

The Dynamic Vapor Sorption (DVS) DVS data were collected on a VTI SGA-100 Vapor Sorption Analyzer. NaCl and PVP were used as calibration standards. The sample was not dried prior to analysis. Sorption and desorption data were collected over a range from 5 to 95% RH at 10% RH increments under a nitrogen purge. The equilibrium criterion used for analysis was less than 0.0100% weight change in 5 minutes with a maximum equilibration time of 3 hours. Data were not corrected for the initial moisture content of the samples. The isotherm of the material is shown in FIG. 3.

Example 4

Preparation of Amorphous Rebaudioside X Via Water Process

A 100 g sample containing Rebaudioside D (1.18%), Form A Rebaudioside X (97.4%), Rebaudioside A (0.04%)—all percentages being on a percent dry weight basis—and having water solubility of 0.05%, was mixed with 300 g of water and incubated in thermostatted oil bath. The temperature was increased at 1° C. per minute to 121° C. The mixture was maintained at 121° C. for 1 hour and then the temperature was decreased to room temperature (25° C.) at 1° C. per minute to give a concentrated solution of Rebaudioside X.

100 g of the concentrated solution was dried using YC-015 laboratory spray drier (Shanghai Pilotech Instrument & Equipment Co. Ltd., China) operating at 175° C. inlet and 100° C. outlet temperature. 20 g of amorphous Rebaudioside X powder was obtained that had a water solubility greater than 1%. The X-ray diffraction pattern of the material is shown in FIG. 4.

Example 5

Preparation of Amorphous Rebaudioside X Via Ethanol Process 2.5 g Form A Rebaudioside X (97.4% purity, obtained from Pure Circle) in anhydrous absolute ethanol (500 mL) was refluxed for 2 hours under a nitrogen atmosphere then cooled to room temperature. The solvent was then evaporated and dried under vacuum at 40 C for 2.5 days to provide 2.35 g of a white solid. The X-ray diffraction pattern of the resulting amorphous Rebaudioside X is shown in FIG. 4.

Example 6

Characterization of Amorphous Rebaudioside X

Figure 5:
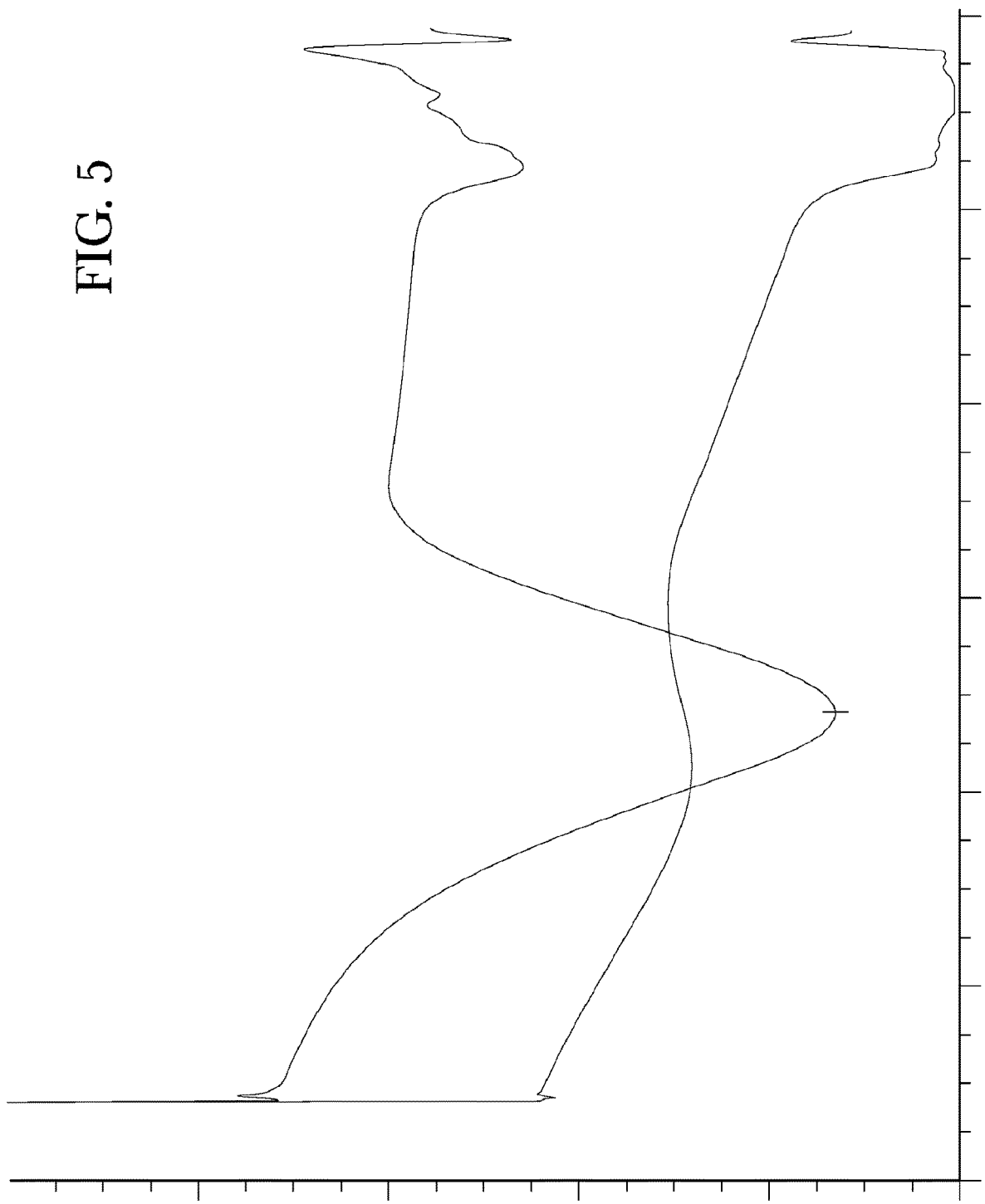
FIG. 5: illustrates the Differential Scanning calorimetry (DSC) thermogram of amorphous Rebaudioside X obtained by heating at 2° C./min.

Modulated DSC analysis performed in an attempt to determine the $T_g$ of the amorphous Rebaudioside X was inconclusive; i.e. no clear glass transition event was observed under instrumental parameters examined. A broad endotherm was observed at approximately 71° C. (peak) from heat flow signal due to the loss of volatiles (FIG. 5) Dark brown material was noticed at the end of the test, suggesting degradation.

Differential Scanning calorimetry (DSC) was conducted on a TA Instruments 2920 differential scanning calorimeter. Temperature calibration was performed using NIST-traceable indium metal. The sample was placed into an aluminum DSC pan, covered with a lid (TOCMP-Tzero crimped pan, manual pinhole), and the weight was accurately recorded. A weighed aluminum pan configured as the sample pan was placed on the reference side of the cell. The method was run starting from −30° C. to 250° C., at 10° C./min.

Figure 6:
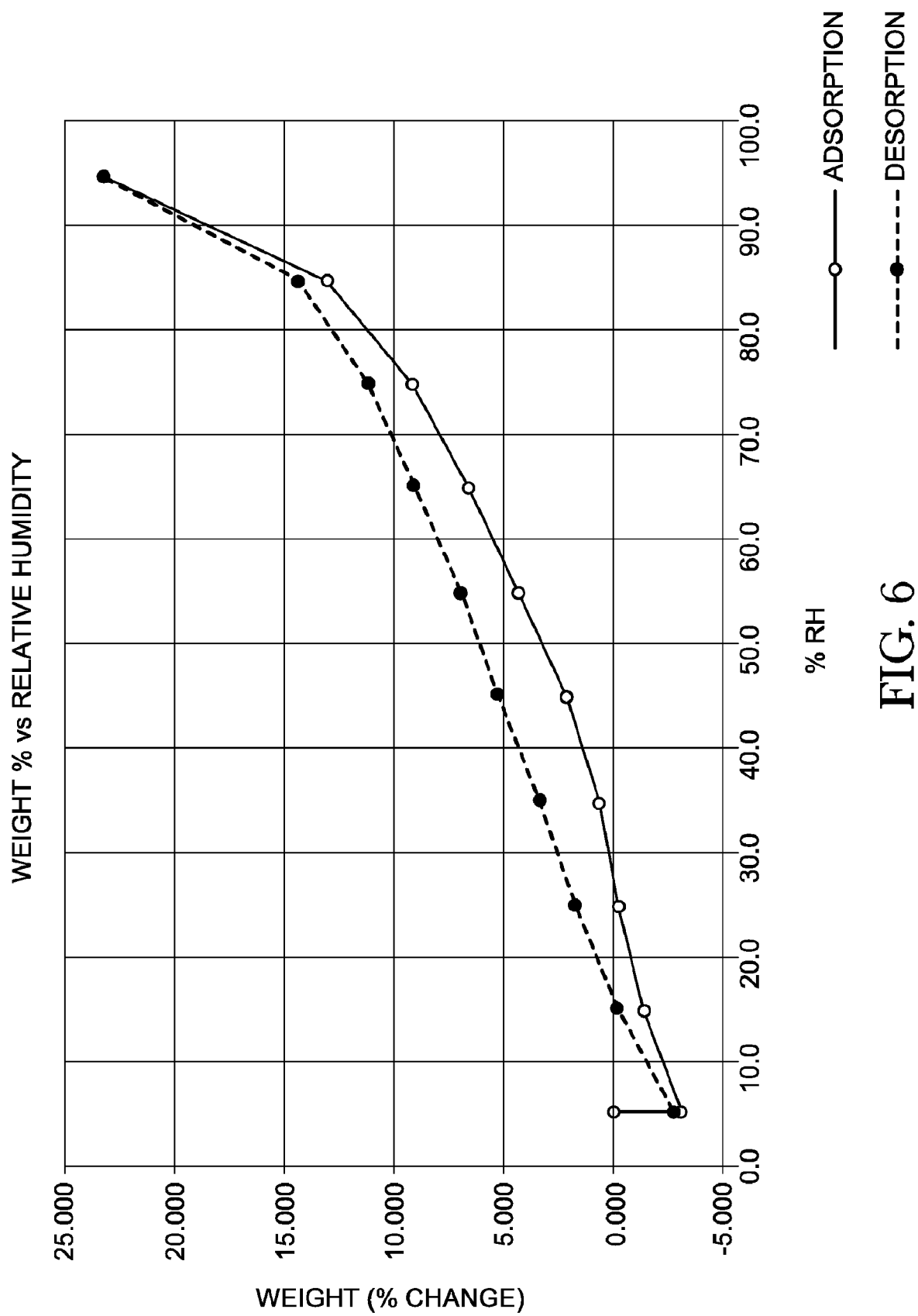
FIG. 6: illustrates the Dynamic Vapor Soprtion (DVS) isotherm of amorphous Rebaudioside X.

The DVS isotherm of amorphous Rebaudioside X is shown in FIG. 6. The material exhibited a 3.1 wt % loss upon equilibration at 5% RH and gained 26.3 wt % with increasing the relative humidity from 5% to 95% RH. The material exhibited evidence of hysteresis with a 26.0 wt % loss upon desorption from 95% to 5% RH. The large weight change suggests that the material is hygroscopic. The solids recovered after DVS is x-ray amorphous, suggesting that crystallization had not occurred during the DVS analysis.

Example 7

Crystallinity of Form A and Amorphous Rebaudioside X

Polarized Light Microscopy (PLM) was performed using a Leica MZ12.5 stereomicroscope. Samples were viewed in situ or on a glass slide (generally covered in mineral oil) with crossed polarizers and a first order red compensator using various objectives ranging from 0.8-10×. Crystallinity is indicated by the observance of birefringence and extinction. The results are shown in Table 5. Polarized Light Microscopy experiments on Form A Rebaudioside X indicate the material is crystalline. Polarized Light Microscopy experiments on amorphous Rebaudioside X indicate the material is non-crystalline.

TABLE 5

| Polarized Light Microscopy | |
|---|---|
| Material | Result |
| Form A | birefringence and extinction |
| Amorphous (water process) | glass, no birefringence |
| Amorphous (ethanol process) | glass, no birefringence |

Example 8

Approximate Water Solubility of Form A and Amorphous Rebaudioside X

The approximate water solubility of Form A and amorphous Rebaudioside X were determined by a solvent addition method in which a weighed sample was treated with aliquots of water. The mixture was generally vortexed and/or sonicated between additions to facilitate dissolution. Complete dissolution of the test material was determined by visual inspection. Solubility was estimated based on the total solvent used to provide complete dissolution. The actual solubility may be greater than the value calculated because of the use of solvent aliquots that were too large or due to a slow rate of dissolution.

TABLE 6

| Approximate Water Solubility of Rebaudioside X Forms | |
|---|---|
| Rebaudioside X Form | Approximate Water Solubility (mg/mL) |
| Form A | 1.4 |
| Amorphous (water process) | >10 |
| Amorphous (ethanol process) | >10 |

As shown in Table 6, the approximate water solubility for amorphous Rebaudioside X—prepared by using either water or ethanol as the solvent—is substantially increased compared to the approximate water solubility of Form A Rebaudioside X.

Example 9

Water Solubility of Amorphous Rebaudioside X

The water solubility of amorphous Rebaudioside X prepared according to Example 4 was compared in various test material/water ratios with or without filtration prior to solubility determination. The results are shown in Table 7. Generally, filtration performed after dissolution of sample assist the duration of clarity of the sample (or delays the precipitation/recrystallization of sample). Based on the benefit of the filtration process, amorphous Reabudioside X can be sieved to less than 200 nm of particle size to improve its solubility profile in aqueous solution.

TABLE 7

| Sample | Rebaudioside X mg/ mL water | Filtered† | Duration of Clarity of Sample |
|---|---|---|---|
| 1 | 250/500 | No | >60 days[a] |
| 2 | 500/500 | No | >60 days[a] |
| 3 | 750/500 | No | >3 h |
| 4 | 1000/500 | No | —[b] |
| 5 | 625/250 | Yes | >1 day |
| 6 | 1750/500 | No | ~3 h |
| 7 | 1750/500 | Yes | >1 day |
| 8 | 1000/100 | Yes | ~2 h |

†0.22 μm membrane filter used using vacuum filtration apparatus. Only ~10 mg of Rebaudioside X from 1 g of Rebaudioside X remained on the filter.
[a]The solution is still clear and the observation is stopped.
[b]Most Rebaudioside X dissolved quickly. However, a small amount of floating particles remained.

Example 10

Determination of Equilibrium Solubility of Rebaudioside X

Samples were analyzed with a Cary 50 UV-Vis dual beam spectrophotometer. The detector was zeroed with a cuvette filled with water prior to sample analysis. Samples were analyzed at room temperature in 1.0 cm quartz cuvette using a scan rate of 600 nm/min in a range of 200-400 nm.

25.8 mg of amorphous Rebaudioside X was added to a 10-mL volumetric flask and dissolved 10 mL with water. This stock solution was diluted to five concentration levels for UV measurement. The UV spectrum of Rebaudioside X was determined at five concentration levels as listed in Table 8:

TABLE 8

| Sample | Stock Solution Volume (mL) | Final Volume (mL) | Concentration (mg/mL) | Absorbance (205 nm) |
|---|---|---|---|---|
| 1 | 1.0 | 500.0 | 0.00479 | 0.01981 |
| 2 | 1.0 | 100.0 | 0.02394 | 0.11903 |
| 3 | 1.0 | 50.0 | 0.04787 | 0.24857 |
| 4 | 1.0 | 10.0 | 0.23937 | 1.22797 |
| 5 | 1.0 | 5.0 | 0.48784 | 2.41871 |

A calibration curve at 205 nm was established (Abs at 205 nm vs. concentration) to provide the equation $y=5.0625x+0.0022$. $R^2$ was 0.9999. This equation was used for the subsequent determination of Rebaudioside X concentrations.

250 mg of amorphous Rebaudioside X was added to an amber vial and 10 mL of water was added. The mixture was stirred at room temperature about 10 minutes to yield a transparent solution with only small amount of solid remaining. The mixture became opaque rapidly. The mixture was placed on a mechanical oscillator set at a speed of 250 and 25° C. At the sampling time point of 1, 16, 24, 48, 72, 96, and 192 hours, an aliquot of the slurry was transferred to a centrifuge tube and separated at a speed of 16K rcf for 15 minutes. 200 µL of the clear supernatant was transferred to a 50-mL volumetric flask, 10 mL of water was added and mixed well before UV analysis. The results are summarized in Table 9.

TABLE 9

| Sample | Sampling Time (hrs) | Original Sample Volume (mL) | Test Sample Volume (mL) | Test Sample Abs (205 nm) | Test Sample Concentration (mg/mL) | Original Sample Concentration (mg/mL) |
|---|---|---|---|---|---|---|
| 1 | 1 | 0.2 | 50.0 | 0.11961 | 0.02319 | 5.8 |
| 2 | 16 | 0.2 | 10.2 | 0.26601 | 0.05211 | 2.7 |
| 3 | 24 | 0.2 | 10.2 | 0.25924 | 0.05077 | 2.6 |
| 4 | 48 | 0.2 | 10.2 | 0.24951 | 0.04885 | 2.5 |
| 5 | 72 | 0.2 | 10.2 | 0.27681 | 0.05424 | 2.8 |
| 6 | 96 | 0.2 | 10.2 | 0.27687 | 0.05426 | 2.8 |
| 7 | 192 | 0.2 | 10.2 | 0.25929 | 0.05078 | 2.6 |

Average Sample Concentration = 2.6

Equilibrium was established within 16 hours and equilibrium solubility was determined to be 2.6 mg/mL.)(RFD pattern of the solids recovered after 8 days solubility testing was consistent with Form A, indicating conversion.

Example 11

Preparation and Characterization of Form B Rebaudioside X

Amorphous Rebaudioside X (151.1 mg) was combined with ethanol (3 mL) to give a slurry. The slurry was stirred at approximately 40° C. for 5 days, resulting in a white suspension. The solid was isolated by centrifugation using a centrifuge tube equipped with a filter. White damp solids were air dried for approximately 2 hours to provide Form B Rebaudioside X. The X-ray diffraction pattern is shown in FIGS. 7A and 7B. Form B was successfully indexed, indicating that the sample is composed primarily of a single crystalline phase. Non-systematic peak shifts between the X-ray diffraction patterns of Form B are observed and are likely due to unit cell volume differences and indicate Form B is a variable hydrate/solvate. The unit cell volume may change to accommodate varying X-ray diffraction pattern peak positions are a direct result of the unit cell parameters. The angular positions (two theta) of the prominent X-ray diffraction peaks are as follows:

TABLE 2

| Form B Rebaudioside X Prominent XPRD | | |
|---|---|---|
| °2Θ | d space (Å) | Intensity (%) |
| 4.20 ± 0.20 | 21.058 ± 1.053 | 100 |
| 5.17 ± 0.20 | 17.108 ± 0.689 | 41 |
| 6.47 ± 0.20 | 13.664 ± 0.435 | 78 |
| 7.40 ± 0.20 | 11.939 ± 0.331 | 54 |
| 7.92 ± 0.20 | 11.159 ± 0.289 | 99 |
| 13.40 ± 0.20 | 6.606 ± 0.100 | 70 |
| 14.46 ± 0.20 | 6.127 ± 0.085 | 57 |
| 16.08 ± 0.20 | 5.513 ± 0.069 | 65 |
| 17.48 ± 0.20 | 5.073 ± 0.058 | 91 |
| 18.15 ± 0.20 | 4.888 ± 0.054 | 71 |

Example 10

Conversion of Material E Rebaudioside X to Form A Rebaudioside X

Material E Rebaudioside X was combined with water (6 mL) to give a slurry. The slurry was agitated on a shaker block at approximately 60° C. for 6 days. The resulting solids were isolated by centrifugation for 5 min using a centrifuge tube equipped with a PVDF membrane filter to provide Form A Rebaudioside X.

Material E Rebaudioside X (58.5 mg) was combined with water (5 mL). The mixture was then stirred at 87° C. to obtain a clear solution. The solution was cool slowly to ambient temperature by switching the heat off and left overnight. The resulting solids were isolated by centrifugation utilizing centrifuge tube equipped with a PVDF membrane filter to provide Form A Rebaudioside X.

Figure 8:
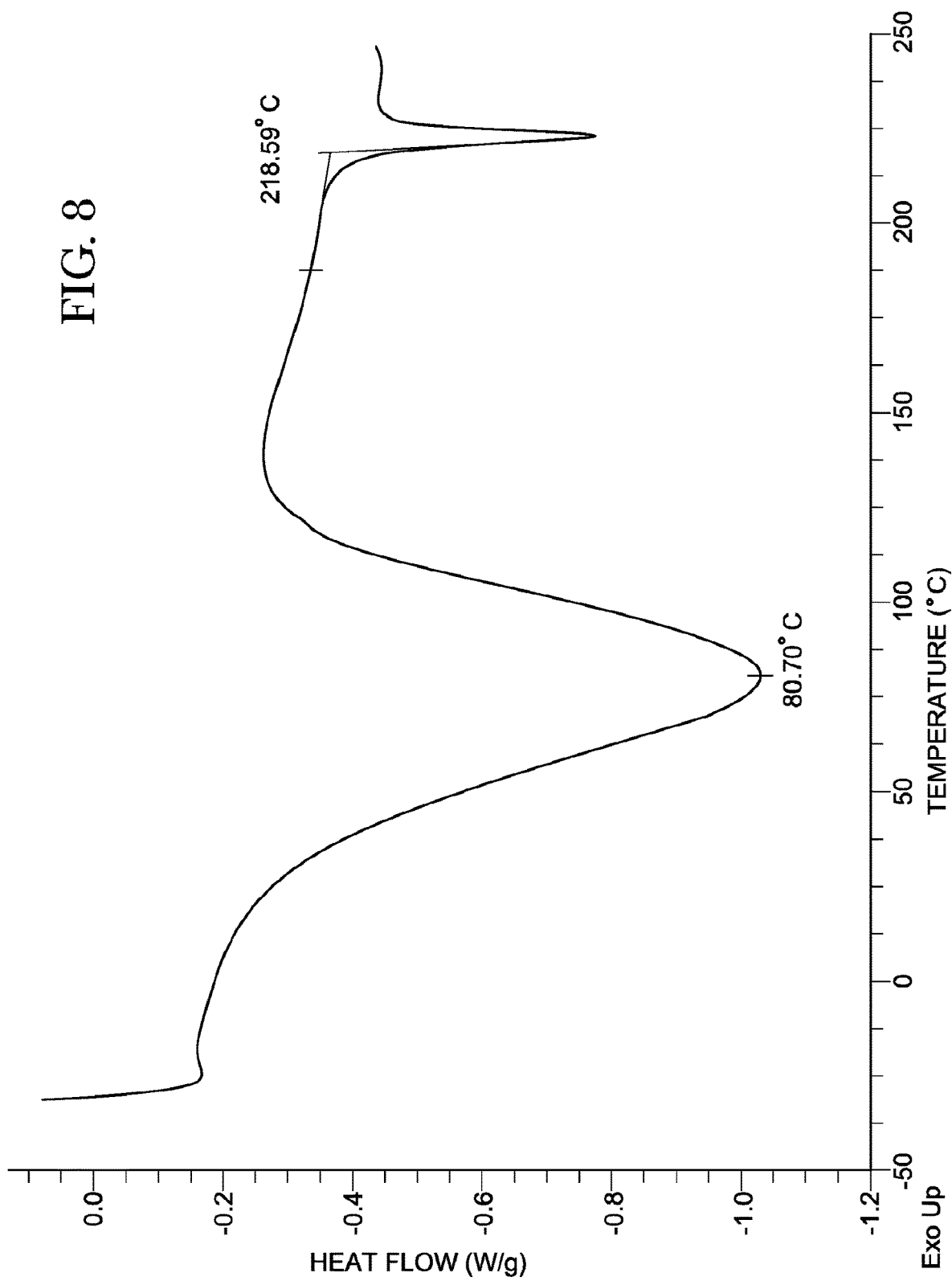
FIG. 8: illustrates Differential Scanning calorimetry (DSC) thermogram of Material E.
Figure 9:
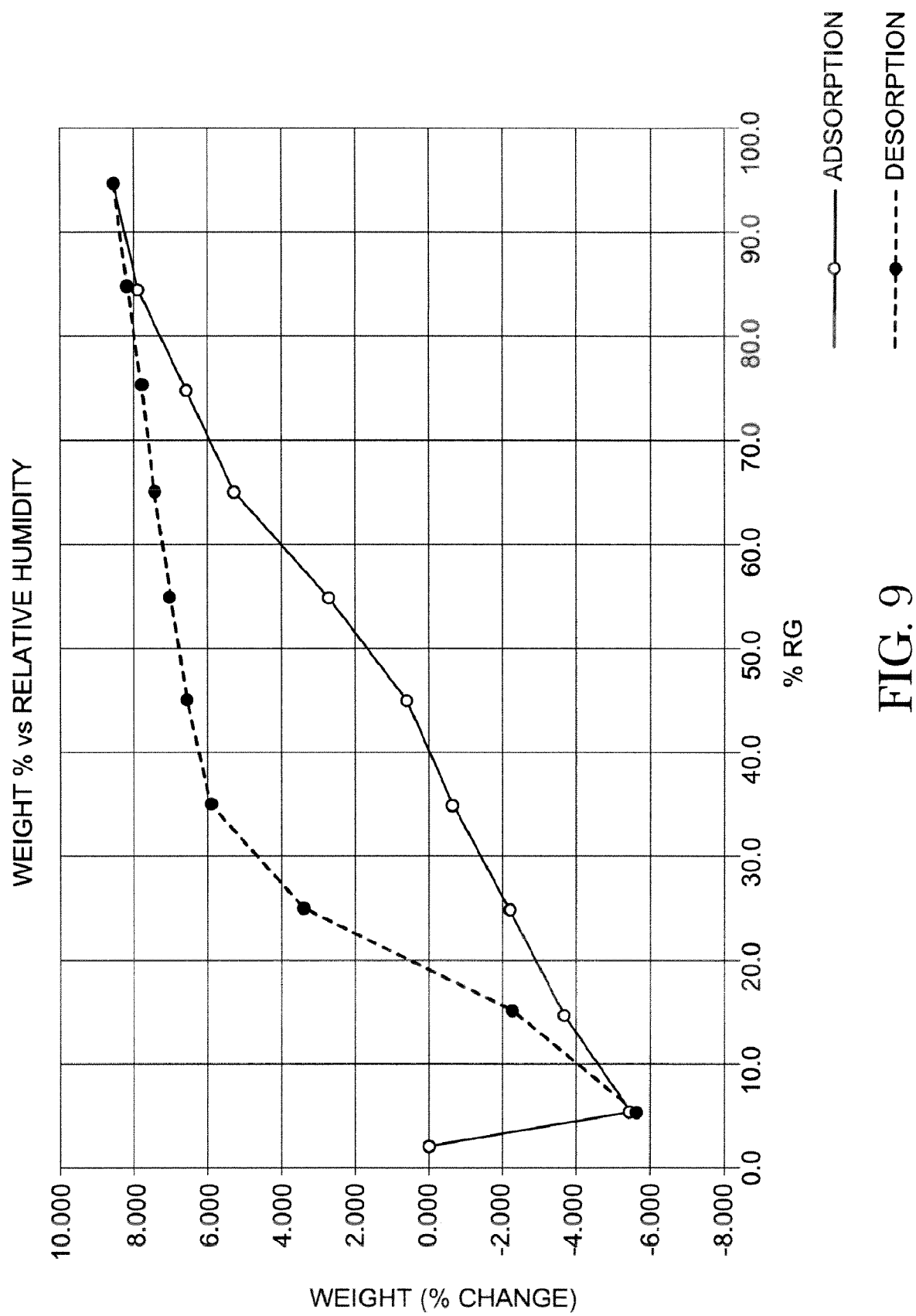
FIG. 9: illustrates the Dynamic Vapor Sorption (DVS) thermogram of Material E.

The DSC of Material E displays a broad endotherm at approximately 81° C. (peak), likely due to the loss of volatiles (FIG. 8). An endotherm was observed at ~219° C. (onset), attributable to melting, based on Hot-Stage Microscopy (HSM) observations.

Example 13

Rebaudioside X Complexes

1:4 mixture of Rebaudioside X and γ-cyclodextrin Rebaudioside X (1.0 g) and γ-cyclodextrin (4.0 g) were added to water (100 mL) and heated between 100° C. and 120° C. until all materials were dissolved and the mixture was clear by visual inspection. The mixture was cooled to room temperature and freeze-dried for two days to provide a white solid (4.28 g, 86% yield).

1:2 Mixture of Rebaudioside X and γ-Cyclodextrin
Rebaudioside X (2.0 g) and γ-cyclodextrin (4.0 g) were added to water (100 mL) and heated between 100° C. and 120° C. until all materials were dissolved and the mixture was clear by visual inspection. The mixture was cooled to room temperature and freeze-dried for two days to provide a white solid (5.27 g, 88% yield).

1:1 Mixture of Rebaudioside X and γ-Cyclodextrin
Rebaudioside X (2.0 g) and γ-cyclodextrin (2.0 g) were added to water (100 mL) and heated between 100° C. and 120° C. until all materials were dissolved and the mixture was clear by visual inspection. The mixture was cooled to room temperature and freeze-dried for two days to provide a white solid (3.37 g, 84%).

1:1 Mixture of Rebaudioside X and Maltodextrin
Rebaudioside X (1.0 g) and maltodextrin (1.0 g) were added to water (100 mL) and heated between 100° C. and 120° C. until all materials were dissolved and the mixture was clear by visual inspection. The mixture was cooled to room temperature and freeze-dried for two days to provide a white solid.

1:1 Mixture of Rebaudioside X and Erythritol

Rebaudioside X (1.0 g) and erythritol (1.0 g) were added to water (100 mL) and heated between 100° C. and 120° C. until all materials were dissolved and the mixture was clear by visual inspection. The mixture was cooled to room temperature and freeze-dried for two days to provide a white solid (1.87 g, 93%).

The approximate solubility of the complexes was measured by a solvent addition method in which a weighed sample was treated with aliquots of water. The mixture was generally vortexed and/or sonicated between additions to facilitate dissolution. Complete dissolution of the test material was determined by visual inspection. Solubility was estimated based on the total solvent used to provide complete dissolution. The actual solubility may be greater than the value calculated because of the use of solvent aliquots that were too large or due to a slow rate of dissolution. The results are provided in Table 10.

TABLE 10

| Rebaudioside X Complex | Approximate Water Solubility (mg/mL) |
|---|---|
| Rebaudioside X:γ-cyclodextrin (1:4) | >250 |
| Rebaudioside X:γ-cyclodextrin (1:2) | >150 |
| Rebaudioside X:γ-cyclodextrin (1:1) | >75 |
| Rebaudioside X:maltodextrin (1:1) | >100 |
| Rebaudioside X:erythritol (1:1) | >100 |

Discussion

The approximate water solubility of all of the Rebaudioside X complexes was greater than the approximate solubility of Form A Rebaudioside X alone (14 mg/mL). Within the complexes, the 1:2 and 1:4 complexes of Rebaudioside X and γ-cyclodextrin provided the greatest water solubility. The 1:1 complex of Rebaudioside X and maltodextrin and the 1:1 complex of Rebaudioside X and erythritol both had water solubilities >100 mg/mL. The 1:1 Rebaudioside X and cyclodextrin complex had a water solubility of >75 mg/mL.

What Is Claimed Is:

1. A method for preparing amorphous Rebaudioside X comprising:
   (i) heating a mixture consisting of water and a steviol glycoside mixture comprising Rebaudioside X in an amount greater than about 80% by weight on a dry basis, wherein the Rebaudioside X is in substantially pure crystalline form, to a temperature between about 100° C. to about 130° C.;
   (ii) cooling the mixture; and
   (iii) removing the water from the mixture to provide a steviol glycoside mixture comprising Rebaudioside X in an amount greater than about 80% by weight on a dry basis, wherein the Rebaudioside X is in substantially pure amorphous form.

2. The method of claim 1, wherein the Rebaudioside X in (i) is Form A Rebaudioside X.

3. The method of claim 1, wherein the mixture is heated to a temperature from about 120° C. to about 125° C.

4. The method of claim 1, wherein the mixture in (ii) is cooled to room temperature such that crash precipitation does not occur.

5. The method of claim 4, wherein the mixture is cooled at a rate of about 1° C. per minute.

6. The method of claim 1, wherein the water is removed by a process selected from the group consisting of decantation, centrifugation, filtration, evaporation, vacuum, spray-drying and a combination thereof.

7. The method of claim 6, wherein the water is removed by spray-drying.

8. The method of claim 1, wherein the amorphous Rebaudioside X has a solubility of about 0.3% or greater.

9. The method of claim 1, wherein the amorphous Rebaudioside X has a solubility of about 1.0% or greater.

10. A method for preparing amorphous Rebaudioside X comprising:
    (i) heating a mixture consisting of ethanol and a steviol glycoside mixture comprising Rebaudioside X in an amount greater than about 80% by weight on a dry basis, wherein the Rebaudioside X is in substantially pure crystalline form, to a temperature between about 70° C. to about 120° C.;
    (ii) cooling the mixture; and
    (iii) removing the ethanol from the mixture to provide a steviol glycoside mixture comprising Rebaudioside X in an amount greater than about 80% by weight on a dry basis wherein the Rebaudioside X is in substantially pure amorphous form.

11. The method of claim 10, wherein the Rebaudioside X in (i) is Form A Rebaudioside X.

12. The method of claim 10, wherein the mixture is heated to a temperature between about 80° C. and about 85° C.

13. The method of claim 10, wherein the mixture in (ii) is cooled to about room temperature such that crash precipitation does not occur.

14. The method of claim 10, wherein the ethanol is removed by a process selected from the group consisting of decantation, centrifugation, filtration, evaporation, vacuum, spray-drying and a combination thereof.

15. The method of claim 14, wherein the ethanol is removed by vacuum.

16. The method of claim 10, wherein the amorphous Rebaudioside X has a solubility of about 0.3% or greater.

17. The method of claim 10, wherein the amorphous Rebaudioside X has a solubility of about 1.0% or greater.

* * * * *